United States Patent
Zhu et al.

(10) Patent No.: US 8,543,203 B2
(45) Date of Patent: *Sep. 24, 2013

(54) ENDOCARDIAL PACING DEVICES AND METHODS USEFUL FOR RESYNCHRONIZATION AND DEFIBRILLATION

(75) Inventors: Qingsheng Zhu, Wexford, PA (US); Daniel Felipe Ortega, Buenos Aires (AR)

(73) Assignee: Cardiac Pacemakers, Inc., St. Paul, MN (US)

( * ) Notice: Subject to any disclaimer, the term of this patent is extended or adjusted under 35 U.S.C. 154(b) by 82 days.

This patent is subject to a terminal disclaimer.

(21) Appl. No.: 13/211,937

(22) Filed: Aug. 17, 2011

(65) Prior Publication Data
US 2012/0041500 A1 Feb. 16, 2012

Related U.S. Application Data

(63) Continuation of application No. 12/147,425, filed on Jun. 26, 2008, now Pat. No. 8,005,544, which is a continuation-in-part of application No. 11/300,611, filed on Dec. 13, 2005, now Pat. No. 7,512,440, and a continuation-in-part of application No. 11/300,242, filed on Dec. 13, 2005, now Pat. No. 8,346,358.

(60) Provisional application No. 60/947,336, filed on Jun. 29, 2007, provisional application No. 60/947,308, filed on Jun. 29, 2007.

(30) Foreign Application Priority Data
Dec. 20, 2004 (AR) .............................. 2004/0104782

(51) Int. Cl.
*A61N 1/362* (2006.01)

(52) U.S. Cl.
USPC .............................................................. 607/9

(58) Field of Classification Search
USPC ............................................ 607/2, 4, 5, 9, 25
See application file for complete search history.

(56) References Cited

U.S. PATENT DOCUMENTS
3,614,955 A 10/1971 Mirowski
3,804,098 A 4/1974 Friedman
(Continued)

FOREIGN PATENT DOCUMENTS
DE 2827595 A1 4/1979
DE 3712082 A1 10/1988
(Continued)

OTHER PUBLICATIONS
"U.S. Appl. No. 11/300,242, Notice of Allowance mailed Aug. 24, 2012", 7 pgs.
(Continued)

*Primary Examiner* — Brian T Gedeon
(74) *Attorney, Agent, or Firm* — Schwegman Lundberg & Woessner, P.A.

(57) ABSTRACT

According to one aspect, various methods and apparatus are used for treating a condition of a patient's heart, and for monitoring cardiac operation. In one approach consistent therewith, an electrode arrangement is placed in a right ventricle of the heart. The electrode arrangement is used to capture the myocardium for re-synchronization of the left and right ventricles by providing first and second signal components having opposite polarity on respective electrodes. The electrode arrangement is connected to an implantable CRM device that has the capability of pacing/sensing atrium, pacing/sensing ventricles, and deliver defibrillation therapy from the right side of the heart. The CRM device captures ventricular contractions to treat conduction abnormalities in one or more of the ventricles.

21 Claims, 29 Drawing Sheets

(56) References Cited

U.S. PATENT DOCUMENTS

| | | |
|---|---|---|
| 3,866,615 A | 2/1975 | Hewson |
| 3,911,928 A | 10/1975 | Lagergren |
| 3,942,536 A | 3/1976 | Mirowski et al. |
| 3,949,757 A | 4/1976 | Sabel |
| 3,995,623 A | 12/1976 | Blake et al. |
| 4,026,303 A | 5/1977 | Babotai |
| 4,030,508 A | 6/1977 | Thalen |
| 4,057,067 A | 11/1977 | Lajos |
| 4,106,512 A | 8/1978 | Bisping |
| 4,136,703 A | 1/1979 | Wittkampf |
| 4,154,247 A | 5/1979 | O'Neill |
| 4,217,913 A | 8/1980 | Dutcher |
| 4,258,725 A | 3/1981 | O'Neill |
| 4,278,093 A | 7/1981 | Lafortune et al. |
| 4,282,885 A | 8/1981 | Bisping |
| 4,289,134 A | 9/1981 | Bernstein |
| 4,289,144 A | 9/1981 | Gilman |
| 4,311,153 A | 1/1982 | Smits |
| 4,332,259 A | 6/1982 | McCorkle, Jr. |
| 4,365,639 A | 12/1982 | Goldreyer |
| 4,393,883 A | 7/1983 | Smyth et al. |
| 4,402,329 A | 9/1983 | Williams |
| 4,437,474 A | 3/1984 | Peers-Trevarton |
| 4,458,677 A | 7/1984 | McCorkle, Jr. |
| 4,458,695 A | 7/1984 | Peers-Trevarton |
| 4,463,765 A | 8/1984 | Gold |
| 4,469,104 A | 9/1984 | Peers-Trevarton |
| 4,497,326 A | 2/1985 | Curry |
| 4,540,236 A | 9/1985 | Peers-Trevarton |
| 4,543,956 A | 10/1985 | Herscovici |
| 4,549,548 A | 10/1985 | Wittkampf et al. |
| 4,559,951 A | 12/1985 | Dahl et al. |
| 4,567,901 A | 2/1986 | Harris |
| 4,570,642 A | 2/1986 | Kane et al. |
| 4,577,643 A | 3/1986 | Beranek |
| 4,589,420 A | 5/1986 | Adams et al. |
| 4,602,645 A | 7/1986 | Barrington et al. |
| 4,603,705 A | 8/1986 | Speicher et al. |
| 4,624,265 A | 11/1986 | Grassi |
| 4,624,266 A | 11/1986 | Kane |
| 4,627,439 A | 12/1986 | Harris |
| 4,630,204 A | 12/1986 | Mortara |
| 4,633,880 A | 1/1987 | Osypka et al. |
| 4,641,649 A | 2/1987 | Walinsky et al. |
| 4,643,201 A | 2/1987 | Stokes |
| 4,646,755 A | 3/1987 | Kane |
| 4,649,937 A | 3/1987 | DeHaan et al. |
| 4,649,938 A | 3/1987 | McArthur |
| 4,664,113 A | 5/1987 | Frisbie et al. |
| 4,667,686 A | 5/1987 | Peers-Travarton |
| H356 H | 11/1987 | Stokes et al. |
| 4,721,115 A | 1/1988 | Owens |
| 4,751,931 A | 6/1988 | Briller et al. |
| 4,784,161 A | 11/1988 | Skalsky et al. |
| 4,785,815 A | 11/1988 | Cohen |
| 4,799,486 A | 1/1989 | DuFault |
| 4,799,493 A | 1/1989 | DuFault |
| 4,819,647 A | 4/1989 | Byers et al. |
| 4,819,661 A | 4/1989 | Heil, Jr. et al. |
| 4,819,662 A | 4/1989 | Heil, Jr. et al. |
| 4,876,109 A | 10/1989 | Mayer et al. |
| 4,886,074 A | 12/1989 | Bisping |
| 4,892,102 A | 1/1990 | Astrinsky |
| 4,895,152 A | 1/1990 | Callaghan et al. |
| 4,922,607 A | 5/1990 | Doan et al. |
| 4,922,927 A | 5/1990 | Fine et al. |
| 4,924,881 A | 5/1990 | Brewer |
| 4,953,564 A | 9/1990 | Berthelsen |
| 4,967,766 A | 11/1990 | Bradshaw |
| 4,972,848 A | 11/1990 | DiDomenico et al. |
| 4,994,078 A | 2/1991 | Jarvik |
| 5,002,067 A | 3/1991 | Berthelsen et al. |
| 5,007,864 A | 4/1991 | Stutz, Jr. |
| 5,016,646 A | 5/1991 | Gotthardt et al. |
| 5,050,601 A | 9/1991 | Kupersmith et al. |
| 5,056,516 A | 10/1991 | Spehr |
| 5,063,932 A | 11/1991 | Dahl et al. |
| 5,076,285 A | 12/1991 | Hess et al. |
| 5,083,564 A | 1/1992 | Scherlag |
| 5,092,879 A | 3/1992 | Jarvik |
| 5,129,404 A | 7/1992 | Spehr et al. |
| 5,144,960 A | 9/1992 | Mehra et al. |
| 5,152,299 A | 10/1992 | Soukup |
| 5,174,289 A | 12/1992 | Cohen |
| 5,179,962 A | 1/1993 | Dutcher et al. |
| 5,181,511 A | 1/1993 | Nickolls et al. |
| 5,223,226 A | 6/1993 | Wittmar et al. |
| 5,242,430 A | 9/1993 | Arenas et al. |
| 5,255,693 A | 10/1993 | Dutcher et al. |
| 5,259,394 A | 11/1993 | Bens |
| 5,259,395 A | 11/1993 | Li |
| 5,267,560 A | 12/1993 | Cohen |
| 5,275,620 A | 1/1994 | Darby et al. |
| 5,282,845 A | 2/1994 | Bush et al. |
| 5,299,569 A | 4/1994 | Wernicke et al. |
| 5,300,108 A | 4/1994 | Rebell et al. |
| 5,304,219 A | 4/1994 | Chernoff et al. |
| 5,306,292 A | 4/1994 | Lindegren |
| 5,313,953 A | 5/1994 | Yomtov et al. |
| 5,320,642 A | 6/1994 | Scherlag |
| 5,324,327 A | 6/1994 | Cohen |
| 5,336,252 A | 8/1994 | Cohen |
| 5,342,414 A | 8/1994 | Mehra |
| 5,344,439 A | 9/1994 | Otten |
| 5,358,516 A | 10/1994 | Myers et al. |
| 5,366,496 A | 11/1994 | Dahl et al. |
| 5,370,665 A | 12/1994 | Hudrlik |
| 5,374,286 A | 12/1994 | Morris |
| 5,381,790 A | 1/1995 | Kanesaka |
| 5,393,929 A | 2/1995 | Yagihashi |
| 5,405,373 A | 4/1995 | Petersson et al. |
| 5,411,544 A | 5/1995 | Mar et al. |
| 5,425,755 A | 6/1995 | Doan |
| 5,433,735 A | 7/1995 | Zanakis et al. |
| 5,439,391 A | 8/1995 | McEtchin et al. |
| 5,447,533 A | 9/1995 | Vachon et al. |
| 5,447,534 A | 9/1995 | Jammet |
| 5,456,706 A | 10/1995 | Pless et al. |
| 5,456,708 A | 10/1995 | Doan et al. |
| 5,466,253 A | 11/1995 | Doan |
| 5,476,497 A | 12/1995 | Mower et al. |
| 5,476,499 A | 12/1995 | Hirschberg |
| 5,476,501 A | 12/1995 | Stewart et al. |
| 5,476,502 A | 12/1995 | Rubin |
| 5,492,119 A | 2/1996 | Abrams |
| 5,500,008 A | 3/1996 | Fain |
| 5,514,172 A | 5/1996 | Mueller |
| 5,515,848 A | 5/1996 | Corbett, III et al. |
| 5,522,874 A | 6/1996 | Gates |
| 5,524,338 A | 6/1996 | Martyniuk et al. |
| 5,527,344 A | 6/1996 | Arzbaecher et al. |
| 5,531,780 A | 7/1996 | Vachon |
| 5,545,201 A | 8/1996 | Helland et al. |
| 5,554,178 A | 9/1996 | Dahl et al. |
| 5,571,163 A | 11/1996 | Helland |
| 5,578,068 A | 11/1996 | Laske et al. |
| 5,593,405 A | 1/1997 | Osypka |
| 5,593,433 A | 1/1997 | Spehr et al. |
| 5,609,158 A | 3/1997 | Chan |
| 5,628,778 A | 5/1997 | Kruse et al. |
| 5,628,779 A | 5/1997 | Bornzin et al. |
| 5,634,829 A | 6/1997 | Kerul |
| 5,634,899 A | 6/1997 | Shapland et al. |
| 5,674,272 A | 10/1997 | Bush et al. |
| 5,674,274 A | 10/1997 | Morgan et al. |
| 5,681,013 A | 10/1997 | Rudolph |
| 5,683,447 A | 11/1997 | Bush et al. |
| 5,702,427 A | 12/1997 | Ecker et al. |
| 5,709,753 A | 1/1998 | Olson et al. |
| 5,716,390 A | 2/1998 | Li |
| 5,718,720 A | 2/1998 | Prutchi et al. |
| 5,720,099 A | 2/1998 | Parker et al. |
| 5,728,140 A | 3/1998 | Salo et al. |
| 5,733,323 A | 3/1998 | Buck et al. |

| Patent No. | Kind | Date | Inventor(s) |
|---|---|---|---|
| 5,755,766 | A | 5/1998 | Chastain et al. |
| 5,769,881 | A | 6/1998 | Schroeppel et al. |
| 5,772,693 | A | 6/1998 | Brownlee |
| 5,782,898 | A | 7/1998 | Dahl et al. |
| 5,800,464 | A | 9/1998 | Kieval |
| 5,800,465 | A | 9/1998 | Thompson et al. |
| 5,807,306 | A | 9/1998 | Shapland et al. |
| 5,810,887 | A | 9/1998 | Accorti, Jr. et al. |
| 5,814,077 | A | 9/1998 | Sholder et al. |
| 5,814,079 | A | 9/1998 | Kieval |
| 5,851,227 | A | 12/1998 | Spehr |
| 5,871,506 | A | 2/1999 | Mower |
| 5,871,529 | A | 2/1999 | Bartig et al. |
| 5,871,531 | A | 2/1999 | Struble |
| 5,876,399 | A | 3/1999 | Chia et al. |
| 5,876,431 | A | 3/1999 | Spehr et al. |
| 5,916,214 | A | 6/1999 | Cosio et al. |
| 5,925,045 | A | 7/1999 | Reimels et al. |
| 5,936,159 | A | 8/1999 | Cross, Jr. et al. |
| 5,941,868 | A | 8/1999 | Kaplan |
| 5,944,710 | A | 8/1999 | Dev et al. |
| 5,964,795 | A | 10/1999 | McVenes et al. |
| 5,972,416 | A | 10/1999 | Reimels et al. |
| 5,995,871 | A | 11/1999 | Knisley |
| 6,006,139 | A | 12/1999 | Kruse et al. |
| 6,007,476 | A | 12/1999 | Wascher et al. |
| 6,024,739 | A | 2/2000 | Ponzi et al. |
| 6,059,726 | A | 5/2000 | Lee et al. |
| 6,070,104 | A | 5/2000 | Hine et al. |
| 6,086,582 | A | 7/2000 | Altman et al. |
| 6,096,069 | A | 8/2000 | Bischoff |
| 6,123,084 | A | 9/2000 | Jandak et al. |
| 6,141,588 | A | 10/2000 | Cox et al. |
| 6,141,594 | A | 10/2000 | Flynn et al. |
| 6,161,029 | A | 12/2000 | Spreigl et al. |
| 6,165,164 | A | 12/2000 | Hill et al. |
| 6,212,434 | B1 | 4/2001 | Scheiner et al. |
| 6,219,581 | B1 | 4/2001 | Schaldach et al. |
| 6,230,061 | B1 | 5/2001 | Hartung |
| 6,236,887 | B1 | 5/2001 | Ben-Haim et al. |
| 6,254,573 | B1 | 7/2001 | Haim et al. |
| 6,256,541 | B1 | 7/2001 | Heil et al. |
| 6,267,778 | B1 | 7/2001 | Cohen |
| 6,309,370 | B1 | 10/2001 | Haim et al. |
| 6,341,235 | B1 | 1/2002 | Mower |
| 6,345,204 | B1 | 2/2002 | Scheiner et al. |
| 6,358,247 | B1 | 3/2002 | Altman et al. |
| 6,363,286 | B1 | 3/2002 | Zhu et al. |
| 6,416,510 | B1 | 7/2002 | Altman et al. |
| 6,430,441 | B1 | 8/2002 | Levine |
| 6,463,334 | B1 | 10/2002 | Flynn et al. |
| 6,468,263 | B1 | 10/2002 | Fischell et al. |
| 6,471,697 | B1 | 10/2002 | Lesh |
| 6,484,057 | B2 | 11/2002 | Ideker et al. |
| 6,505,082 | B1 | 1/2003 | Scheiner et al. |
| 6,535,766 | B1 | 3/2003 | Thompson et al. |
| 6,540,725 | B1 | 4/2003 | Ponzi |
| 6,542,775 | B2 | 4/2003 | Ding et al. |
| 6,544,270 | B1 | 4/2003 | Zhang |
| 6,547,787 | B1 | 4/2003 | Altman et al. |
| 6,556,874 | B2 | 4/2003 | Audoglio |
| 6,560,489 | B2 | 5/2003 | Hauck |
| 6,575,931 | B1 | 6/2003 | Ponzi |
| 6,585,716 | B2 | 7/2003 | Altman |
| 6,606,517 | B1 | 8/2003 | Park et al. |
| 6,609,027 | B2 | 8/2003 | Kroll et al. |
| 6,623,473 | B1 | 9/2003 | Ponzi |
| 6,623,474 | B1 | 9/2003 | Ponzi |
| 6,643,546 | B2 | 11/2003 | Mathis et al. |
| 6,650,940 | B1 | 11/2003 | Zhu et al. |
| 6,702,744 | B2 | 3/2004 | Mandrusov et al. |
| 6,702,777 | B2 | 3/2004 | Haim et al. |
| 6,718,206 | B2 | 4/2004 | Casavant |
| 6,766,190 | B2 | 7/2004 | Ferek-Petric |
| 6,768,923 | B2 | 7/2004 | Ding et al. |
| 6,801,807 | B2 | 10/2004 | Abrahamson |
| 6,804,555 | B2 | 10/2004 | Warkentin |
| 6,810,286 | B2 | 10/2004 | Donovan et al. |
| 6,855,124 | B1 | 2/2005 | Gonzalez et al. |
| 6,901,289 | B2 | 5/2005 | Dahl et al. |
| 6,905,476 | B2 | 6/2005 | Ponzi |
| 6,907,285 | B2 | 6/2005 | Denker et al. |
| 6,909,920 | B2 | 6/2005 | Lokhoff et al. |
| 6,915,169 | B2 | 7/2005 | Flynn et al. |
| 6,931,286 | B2 | 8/2005 | Sigg et al. |
| 6,937,897 | B2 | 8/2005 | Min et al. |
| 7,027,876 | B2 | 4/2006 | Casavant et al. |
| 7,039,462 | B2 | 5/2006 | Pastore et al. |
| 7,096,051 | B1 | 8/2006 | Alder |
| 7,113,825 | B2 | 9/2006 | Pastore et al. |
| 7,130,682 | B2 | 10/2006 | Stahmann et al. |
| 7,187,970 | B2 | 3/2007 | Shemer et al. |
| 7,245,973 | B2 | 7/2007 | Liu et al. |
| 7,257,443 | B2 | 8/2007 | Pastore et al. |
| 7,280,872 | B1 | 10/2007 | Mosesov et al. |
| 7,317,950 | B2 | 1/2008 | Lee |
| 7,319,900 | B2 | 1/2008 | Kim et al. |
| 7,359,837 | B2 | 4/2008 | Drew |
| 7,392,095 | B2 | 6/2008 | Flynn et al. |
| 7,395,042 | B2 | 7/2008 | Alder |
| 7,400,931 | B2 | 7/2008 | Mandrusov et al. |
| 7,460,914 | B2 | 12/2008 | Mandrusov et al. |
| 7,509,170 | B2 | 3/2009 | Zhang et al. |
| 7,512,440 | B2 | 3/2009 | Ortega et al. |
| 7,529,584 | B2 | 5/2009 | Laske et al. |
| 7,792,580 | B2 | 9/2010 | Borowitz et al. |
| 7,817,784 | B2 | 10/2010 | Wang et al. |
| 8,005,544 | B2 | 8/2011 | Zhu et al. |
| 8,010,191 | B2 | 8/2011 | Zhu et al. |
| 8,010,192 | B2 | 8/2011 | Zhu et al. |
| 8,014,861 | B2 | 9/2011 | Zhu et al. |
| 8,050,756 | B2 | 11/2011 | Zhu et al. |
| 8,078,287 | B2 | 12/2011 | Liu et al. |
| 8,285,376 | B2 | 10/2012 | Ortega et al. |
| 8,290,586 | B2 | 10/2012 | Zhu et al. |
| 8,326,423 | B2 | 12/2012 | Zhu et al. |
| 8,423,139 | B2 | 4/2013 | Zhu et al. |
| 8,428,715 | B2 | 4/2013 | Ortega et al. |
| 2001/0031986 | A1 | 10/2001 | Hauck |
| 2001/0044619 | A1 | 11/2001 | Altman |
| 2002/0010492 | A1 | 1/2002 | Donovan et al. |
| 2002/0016615 | A1 | 2/2002 | Dev et al. |
| 2002/0022863 | A1 | 2/2002 | Hauck |
| 2002/0026228 | A1 | 2/2002 | Schauerte |
| 2002/0049478 | A1 | 4/2002 | Ding et al. |
| 2002/0058981 | A1 | 5/2002 | Zhu et al. |
| 2002/0099413 | A1 | 7/2002 | Mower |
| 2002/0120318 | A1 | 8/2002 | Kroll et al. |
| 2002/0169484 | A1 | 11/2002 | Mathis et al. |
| 2002/0183720 | A1 | 12/2002 | Hill et al. |
| 2002/0193836 | A1 | 12/2002 | Schmidt |
| 2002/0198583 | A1 | 12/2002 | Rock et al. |
| 2003/0009145 | A1 | 1/2003 | Struijker-Boudier et al. |
| 2003/0032938 | A1 | 2/2003 | Altman |
| 2003/0069625 | A1 | 4/2003 | Ley et al. |
| 2003/0078625 | A1 | 4/2003 | Casavant |
| 2003/0083711 | A1 | 5/2003 | Yonce et al. |
| 2003/0093104 | A1 | 5/2003 | Bonner et al. |
| 2003/0105492 | A1 | 6/2003 | Ding et al. |
| 2003/0105496 | A1 | 6/2003 | Yu et al. |
| 2003/0109914 | A1 | 6/2003 | Westlund et al. |
| 2003/0113303 | A1 | 6/2003 | Schwartz |
| 2003/0125615 | A1 | 7/2003 | Schwartz |
| 2003/0129750 | A1 | 7/2003 | Schwartz |
| 2003/0163184 | A1 | 8/2003 | Scheiner et al. |
| 2003/0171723 | A1 | 9/2003 | Ponzi |
| 2003/0195470 | A1 | 10/2003 | Ponzi |
| 2004/0006265 | A1 | 1/2004 | Alhussiny |
| 2004/0064176 | A1 | 4/2004 | Min et al. |
| 2004/0104782 | A1 | 6/2004 | Ruffieux |
| 2004/0106958 | A1 | 6/2004 | Mathis et al. |
| 2004/0122484 | A1 | 6/2004 | Hatlestad et al. |
| 2004/0153127 | A1 | 8/2004 | Gordon et al. |
| 2004/0186546 | A1 | 9/2004 | Mandrusov et al. |
| 2004/0213770 | A1 | 10/2004 | Seward et al. |
| 2004/0214182 | A1 | 10/2004 | Sharma et al. |
| 2004/0215240 | A1 | 10/2004 | Lovett et al. |
| 2004/0215249 | A1 | 10/2004 | Corbucci |

| | | | |
|---|---|---|---|
| 2004/0215251 A1 | 10/2004 | Sharma et al. |
| 2004/0260374 A1 | 12/2004 | Zhang et al. |
| 2005/0049516 A1 | 3/2005 | Ideker |
| 2005/0075677 A1 | 4/2005 | Ganion et al. |
| 2005/0125041 A1 | 6/2005 | Min et al. |
| 2005/0136385 A1 | 6/2005 | Mann et al. |
| 2005/0137671 A1 | 6/2005 | Liu et al. |
| 2005/0152516 A1 | 7/2005 | Wang et al. |
| 2005/0159725 A1 | 7/2005 | Tockman et al. |
| 2005/0203580 A1 | 9/2005 | Prentice et al. |
| 2005/0267557 A1 | 12/2005 | Flynn et al. |
| 2005/0277993 A1 | 12/2005 | Mower |
| 2006/0030810 A1 | 2/2006 | Mandrusov et al. |
| 2006/0064027 A1 | 3/2006 | Borowitz et al. |
| 2006/0104596 A1 | 5/2006 | Askins et al. |
| 2006/0116596 A1 | 6/2006 | Zhou et al. |
| 2006/0136001 A1 | 6/2006 | Ortega et al. |
| 2006/0142812 A1 | 6/2006 | Ortega et al. |
| 2006/0224197 A1 | 10/2006 | Havel et al. |
| 2006/0224224 A1 | 10/2006 | Muhlenberg et al. |
| 2007/0027488 A1 | 2/2007 | Kaiser et al. |
| 2007/0060961 A1 | 3/2007 | Echt et al. |
| 2007/0093872 A1 | 4/2007 | Chirife et al. |
| 2007/0093874 A1 | 4/2007 | Chirife et al. |
| 2007/0129764 A1 | 6/2007 | Burnes |
| 2007/0208387 A1 | 9/2007 | Mower |
| 2007/0232949 A1 | 10/2007 | Saksena |
| 2007/0233216 A1 | 10/2007 | Liu et al. |
| 2007/0239219 A1 | 10/2007 | Salo et al. |
| 2008/0262587 A1 | 10/2008 | Flynn et al. |
| 2008/0319496 A1 | 12/2008 | Zhu et al. |
| 2008/0319499 A1 | 12/2008 | Zhu et al. |
| 2008/0319500 A1 | 12/2008 | Zhu et al. |
| 2008/0319501 A1 | 12/2008 | Zhu et al. |
| 2009/0005830 A1 | 1/2009 | Zhu et al. |
| 2009/0005832 A1 | 1/2009 | Zhu et al. |
| 2009/0005846 A1 | 1/2009 | Zhu et al. |
| 2009/0054942 A1 | 2/2009 | Zhu et al. |
| 2009/0093859 A1 | 4/2009 | Ortega et al. |
| 2009/0093861 A1 | 4/2009 | Ortega et al. |
| 2009/0099619 A1 | 4/2009 | Lessmeier et al. |
| 2009/0105778 A1 | 4/2009 | Lee et al. |
| 2009/0259272 A1 | 10/2009 | Reddy et al. |
| 2010/0042176 A1 | 2/2010 | Snell |
| 2010/0318147 A1 | 12/2010 | Forslund et al. |
| 2011/0264158 A1 | 10/2011 | Dong et al. |
| 2011/0264168 A1 | 10/2011 | Dadd et al. |
| 2011/0307026 A1 | 12/2011 | Zhu et al. |
| 2011/0319956 A1 | 12/2011 | Zhu et al. |
| 2012/0041503 A1 | 2/2012 | Zhu et al. |
| 2012/0053651 A1 | 3/2012 | Zhu et al. |
| 2012/0101539 A1 | 4/2012 | Zhu et al. |
| 2012/0239106 A1 | 9/2012 | Maskara et al. |
| 2013/0041423 A1 | 2/2013 | Zhu et al. |

FOREIGN PATENT DOCUMENTS

| | | |
|---|---|---|
| EP | 0042551 A1 | 12/1981 |
| EP | 0057877 A1 | 8/1982 |
| EP | 0282047 A2 | 9/1988 |
| EP | 0321764 A1 | 6/1989 |
| EP | 0452278 A2 | 10/1991 |
| EP | 0573275 A2 | 12/1993 |
| EP | 0591053 A1 | 4/1994 |
| EP | 0612538 A2 | 8/1994 |
| EP | 0620024 A1 | 10/1994 |
| EP | 0672431 A2 | 9/1995 |
| EP | 0709111 A2 | 5/1996 |
| EP | 1234597 A2 | 8/2002 |
| FR | 2465489 | 3/1981 |
| FR | 2575925 A1 | 7/1986 |
| FR | 2757773 A1 | 7/1998 |
| GB | 2240721 | 8/1991 |
| JP | 5501211 A | 3/1993 |
| JP | 10052507 | 2/1998 |
| JP | 2008539894 A | 11/2008 |
| WO | WO-92/20401 A1 | 11/1992 |
| WO | WO-94/22525 A1 | 10/1994 |
| WO | WO-96/15665 A2 | 5/1996 |
| WO | WO-97/40883 A1 | 11/1997 |
| WO | WO-00/74773 A1 | 12/2000 |
| WO | WO-03035170 A1 | 5/2003 |
| WO | WO-2005/011475 A2 | 2/2005 |
| WO | WO-2006068880 A1 | 6/2006 |
| WO | WO-2008/063498 A1 | 5/2008 |
| WO | WO-2009/006327 A1 | 1/2009 |
| WO | WO-2009/006339 A1 | 1/2009 |
| WO | WO-2009006321 A2 | 1/2009 |
| WO | WO-2009006325 A1 | 1/2009 |
| WO | WO-2009006331 A1 | 1/2009 |
| WO | WO-2009/078751 A1 | 6/2009 |
| WO | WO-2010042910 A1 | 4/2010 |
| WO | WO-2010/071849 A2 | 6/2010 |
| WO | WO-2011/139691 A1 | 11/2011 |
| WO | WO-2012/125273 A2 | 9/2012 |

OTHER PUBLICATIONS

"U.S. Appl. No. 12/147,317, Notice of Allowance mailed Jul. 2, 2012", 7 pgs.

"U.S. Appl. No. 12/147,376, Notice of Allowance mailed Aug. 30, 2012", 7 pgs.

"U.S. Appl. No. 12/249,454, Non Final Office Action mailed Sep. 4, 2012", 8 pgs.

"U.S. Appl. No. 12/249,479, Non Final Office Action mailed Sep. 4, 2012", 7 pgs.

"U.S. Appl. No. 13/094,416, Restriction Requirement mailed Aug. 16, 2012", 5 pgs.

"U.S. Appl. No. 13/094,416, Response filed Sep. 17, 2012 to Restriction Requirement mailed Aug. 16, 2012", 8 pgs.

Arcot-Krishnamurthy, S., et al., "Timing for HIS-Bundle Pacing", U.S. Appl. No. 13/277,617, filed Oct. 20, 2011, 40 pgs.

"U.S. Appl. No. 10/004,695, Response filed Mar. 9, 2004 to Non-Final Office Action mailed Dec. 22, 2003", 8 pgs.

"U.S. Appl. No. 11/300,242, Non Final Office Action mailed May 12, 2011", 9 pgs.

"U.S. Appl. No. 11/300,242, Notice of Allowance mailed Jan. 24, 2012", 5 pgs.

"U.S. Appl. No. 11/300,242, Notice of Allowance mailed May 8, 2012", 6 pgs.

"U.S. Appl. No. 11/300,242, Response filed Sep. 12, 2011 to Non Final Office Action mailed May 12, 2011", 8 pgs.

"U.S. Appl. No. 12/147,293, Notice of Allowance mailed Apr. 8, 2011", 12 pgs.

"U.S. Appl. No. 12/147,317, Response filed Apr. 11, 2012 to Final Office Action mailed Oct. 12, 2011", 8 pgs.

"U.S. Appl. No. 12/147,317, Examiner Interview Summary mailed Mar. 15, 2011", 3 pgs.

"U.S. Appl. No. 12/147,317, Final Office Action mailed Oct. 12, 2011", 6 pgs.

"U.S. Appl. No. 12/147,317, Response filed Jun. 27, 2011 to Non Final Office Action mailed Dec. 28, 2010", 11 pgs.

"U.S. Appl. No. 12/147,356, Notice of Allowance mailed Jun. 30, 2011", 15 pgs.

"U.S. Appl. No. 12/147,369, Notice of Allowance mailed Apr. 21, 2011", 7 pgs.

"U.S. Appl. No. 12/147,376, Response filed Feb. 29, 2012 to Non Final Office Action mailed Oct. 3, 2011", 6 pgs.

"U.S. Appl. No. 12/147,376, Final Office Action mailed Apr. 20, 2011", 11 pgs.

"U.S. Appl. No. 12/147,376, Non Final Office Action mailed Oct. 3, 2011", 8 pgs.

"U.S. Appl. No. 12/147,376, Notice of Allowance mailed Mar. 19, 2012", 7 pgs.

"U.S. Appl. No. 12/147,376, Response filed Aug. 22, 2011 to Final Office Action mailed Apr. 20, 2011", 8 pgs.

"U.S. Appl. No. 12/249,454, Examiner Interview Summary mailed Feb. 22, 2012", 3 pgs.

"U.S. Appl. No. 12/249,454, Final Office Action mailed Nov. 23, 2011", 8 pgs.

"U.S. Appl. No. 12/249,454, Non Final Office Action mailed Apr. 6, 2011", 8 pgs.

"U.S. Appl. No. 12/249,454, Response filed Apr. 2, 2012 to Final Office Action mailed Nov. 23, 2011", 12 pgs.

"U.S. Appl. No. 12/249,454, Response filed Aug. 30, 2011 to Non Final Office Action mailed Apr. 6, 2011", 14 pgs.

"U.S. Appl. No. 12/249,479, Final Office Action mailed Dec. 2, 2011", 8 pgs.

"U.S. Appl. No. 12/249,479, Non Final Office Action mailed Apr. 5, 2011", 10 pgs.

"U.S. Appl. No. 12/249,479, Response filed Apr. 2, 2012 to Final Office Action mailed Dec. 2, 2011", 9 pgs.

"U.S. Appl. No. 12/249,479, Response filed Aug. 30, 2011 to Non Final Office Action mailed Apr. 5, 2011", 12 pgs.

"U.S. Appl. No. 12/249,508, Notice of Allowance mailed Feb. 14, 2012", 7 pgs.

"U.S. Appl. No. 12/249,508, Notice of Allowance mailed Jun. 12, 2012", 7 pgs.

"U.S. Appl. No. 12/249,508, Notice of Allowance mailed Oct. 5, 2011", 9 pgs.

"U.S. Appl. No. 12/249,508, Response filed Aug. 30, 2011 to Restriction Requirement mailed Jun. 30, 2011", 8 pgs.

"U.S. Appl. No. 12/249,508, Restriction Requirement mailed Jun. 30, 2011", 6 pgs.

"U.S. Appl. No. 12/412,608, Final Office Action mailed Nov. 21, 2011", 6 pgs.

"U.S. Appl. No. 12/412,608, Non Final Office Action mailed May 26, 2011", 8 pgs.

"U.S. Appl. No. 12/412,608, Notice of Allowance mailed Jun. 6, 2012", 7 pgs.

"U.S. Appl. No. 12/412,608, Response filed Apr. 18, 2012 to Final Office Action mailed Nov. 21, 2011", 7 pgs.

"U.S. Appl. No. 12/412,608, Response filed Sep. 26, 2011 to Non Final Office Action mailed May 26, 2011", 9 pgs.

"Coating Process for Composite Implants", *Medical Materials Update*, vol. 1, No. 12, (Jan. 1995), 3 pgs.

"European Application Serial No. 05849548.2, Response filed Jun. 29, 2011 to Office Action mailed Dec. 20, 2010", 9 pgs.

"European Application Serial No. 08772198.1, Response filed Mar. 31, 2011 to Communication mailed Sep. 30, 2010", 11 pgs.

"European Application Serial No. 08781107.1, Response filed Jun. 14, 2011 to Communication mailed Dec. 14, 2010", 10 pgs.

"European Application Serial No. 08796045.6, Office Action mailed Jan. 4, 2012", 4 pgs.

"European Application Serial No. 08796045.6, Response filed Apr. 15, 2011 to Communication dated Oct. 8, 2010", 10 pgs.

"European Application No. 08796045.6, Response filed May 14, 2012 to Office Action mailed Jan. 4, 2012", 8 pgs.

"Implant Attaches to Bone by Chemical Bond", *Medical Materials Update*, vol. 4, No. 7, (Aug. 1997), 2 pgs.

"International Application Serial No. PCT/US2009/060293, International Preliminary Report on Patentability mailed Apr. 12, 2011", 10 pgs.

"International Application Serial No. PCT/US2009/068859, International Search Report mailed Jul. 5, 2010", 7 pgs.

"International Application Serial No. PCT/US2009/068859, Invitation to Pay Addition Fee mailed Apr. 15, 2010", 6 pgs.

"International Application Serial No. PCT/US2009/068859, Written Opinion mailed Jul. 5, 2010", 12 pgs.

"International Application Serial No. PCT/US2011/033944, International Search Report mailed Sep. 8, 2011", 5 pgs.

"International Application Serial No. PCT/US2011/033944, Written Opinion mailed Sep. 8, 2011", 9 pgs.

"Japanese Application Serial No. 2007-548289, Final Office Action dated Aug. 2, 2011", (w/ English Translation), 5 pgs.

"Japanese Application Serial No. 2007-548289, Office Action mailed Mar. 6, 2012", (w/ English Translation), 3 pgs.

"Japanese Application Serial No. 2007-548289, Response filed May 20, 2011 to Office Action mailed Nov. 24, 2010", (w/ English Translation of Amended Claims), 9 pgs.

"Japanese Application Serial No. 2007-548289, Response filed Jun. 4, 2012 to Office Action mailed Mar. 6, 2012", 3 pgs.

"Japanese Application Serial No. 2007-548289, Response filed Oct. 26, 2011 to Office Action mailed Aug. 3, 2011", (w/ English Translation of Amended Claims), 10 pgs.

"Victrex's PEEK Used for Dialysis Machines", *Medical Material's Update*, vol. 3, No. 3, (Apr. 1996), pp. 1-2.

Al-Khadra, A., et al., "The Role of Electroporation in Difibrillation", *Circulation Research*, 87(9), (Oct. 2000), 797-804.

Avitall, B., et al., "Iontophoretic Transmyocardial Drug Delivery. A Novel Approach to Antiarrhythmic Drug Therapy", *Circulation*, 85(4), (1992), 1582-1593.

Barton, A. J., et al., "Bacterial Adhesion to Orthopedic Implant Polymers", *J. Biomed. Mat. Res.*, 30(3), (Mar. 1996), 403-410.

Chiu, L., et al., "Method for One-Click Deployment and or Configuration of Real-Time Software System Modifications", U.S. Appl. No. 60/558,921, filed Apr. 2, 2004, 8 pgs.

Deshmukh, P., et al., "Permanent, Direct His-Bundle Pacing: A Novel Approach to Cardiac Pacing in Patients With Normal His-Purkinje Activation", *Circulation*, 101(8), (Feb. 29, 2000), 869-877.

Dong, Y., et al., "His-Bundle Capture Verification and Monitoring", U.S. Appl. No. 61/328,248, filed Apr. 27, 2010, 40 pgs.

Flynn, David M. et al., "Extendable and Retractable Lead Having a Snap-Fit Terminal Connector", U.S. Appl. No. 11/173,664, filed Jul. 1, 2005, 53 pgs.

Genc, S., et al., "Methodology for Locking Feature Selection in Integral Snap-Fit Assembly", *Proceedings of DETC '97, 1997 ASME Engineering Technical Conferences*, (Sep. 1997), 1-11.

Ha S. W., et al., "Plasma-Sprayed Hydroxylapatite Coating on Carbon Fibre Reinforced Thermoplastic Composite Materials", *J. Mater. Sci. Mater. Med.*, vol. 5, No. 6-7, (1994), 481-484.

Ingle, F., et al., "Lead Motion Sensing Via Cable Microphonics", U.S. Appl. No. 61/359,430, filed Jun. 29, 2010, 52 pgs.

Jockisch, K. A., et al., "Biological Response to Chopped-Carbon-Fiber-Reinforced Peek", *J. Biomed. Mater. Res.*, vol. 26, No. 2, (1992), 133-146.

Kanno, S., et al., "Establishment of a simple and practical procedure applicable to therapeutic angiogenesis", *Circulation*, 99(20), (May 25, 1999), 2682-2687.

Kaye, D. M., et al., "Frequency-dependent activation of a constitutive nitric oxide synthase and regulation of contractile function in adult rat ventricular myocytes", *Circulation Research*, 78(2), (Feb. 1996), 217-224.

Knapp, C. P, et al., "Snap Fit Terminal Connector", U.S. Appl. No. 09/184,226, filed Nov. 2, 1998, 39 pgs.

Labhasetwar, V., et al., "Iontophoresis for Modulation of Cardiac Drug Delivery in Dogs", *Proc. Natl. Acad. Sci. USA*, 92(7), (Mar. 28, 1995), 2612-2616.

Lin, T. W., at al., "Glass Peek Composite Promotes Proliferation and Osteocalcin of Human Osteoblastic Cells", *J. Biomed. Mater. Res.*, vol. 36, No. 2, (1997), 137-144.

MacNair, R., et al., "The Response of Primary Rat and Human Osteoblasts and an Immortalized Rat Osteoblast Cell Line to Orthopaedic Materials: Comparative Sensitivity of Several Toxicity Indices", *J. Mater. Sci. Mater. Med.*, vol. 8, No. 2, (1997), 105-111.

Mansourati, J., et al., "Left ventricular-based pacing in patients with chronic heart failure: comparison of acute hemodynamic benefits according to underlying heart disease", *Eur J Heart Fail.*, 2(2), (Jun. 2000), 195-199.

Meyer, M. R., et al., "Long-Term Durability of the Interface in FRP Composites After Exposure to Simulated Physiologic Saline Environments", *J. Biomed. Mater. Res.*, 28(10), (1994), 1221-1231.

Morrison, C., et al., "In Vitro Biocompatibility Testing of Polymers for Orthopaedic Implants Using Cultured Fibroblasts and Osteoblasts", *Biomaterials*, vol. 16, No. 13, (1995), pp. 987-992.

Qu, J, et al., "HCN2 overexpression in newborn and adult ventricular myocytes: distinct effects on gating and excitability", *Circ. Res.*, vol. 89(1), (Jul. 6, 2001), e8-e14.

Qu, J, et al., "Sympathetic innervation alters activations of pacemaker current (If) in rat ventricle", *J. Physiol.* 526 Pt 3, (Aug. 1, 2000), 561-569.

Shi, W, et al., "Distribution and prevalence of hyperpolarization-activated cation channel (HCN) mRNA expression in cardiac tissues", *Circ. Res.*, vol. 85(1), (Jul. 9, 1999), e1-6.

Soyer, J., et al., "Experimental Characterisation of a Carbon/PEEK Hip Prothesis in Fatigue", *Chirurgie*, 121, (1996), 658-663.

Takatsuki, et al., "Clinical Implications of "pure" Hisian pacing in addition to para-Hisian pacing for the diagnosis of supraventricular tachycardia", *Heart Rhythm* 3 (12), (Dec. 8, 2006), 1412-1418.

Wang, S. C.-J., et al., "Improved Method and System for Managing Voice Prompt Recordings Prior to Deployment", U.S. Appl. No. 60/532,271, filed Dec. 23, 2003, 12 pgs.

Wenz, L. M., et al., "In Vitro Biocompatibility of Polyetheretherketone and Polysulfone Composites", *J. Biomed. Mater. Res.*, vol. 26, No. 2, (1990), 207-215.

Yu, H., et al., "MinK-related peptide 1: A beta subunit for the HCN ion channel subunit family enhances expression and speeds activation", *Circ. Res.*, 88(12), (Jun. 22, 2001), e84-7.

Zanon, F., et al., "A Feasible Approach for Direct His-Bundle Pacing Using a New Steerable Catheter to Facilitate Precise Lead Placement", *Journal of Cardiovascular Electrophysiology*, 17(1), (Jan. 2006), 29-33.

Zhu, Q., et al., "Methods, Devices and Systems for Cardiac Pacing Therapies Using Intrinsic Activity", U.S. Appl. No. 61/139,117, filed Dec. 19, 2008, 22 pgs.

"U.S. Appl. No. 10/004,695, Non-Final Office Action mailed Dec. 22, 2003", 6 pgs.

"U.S. Appl. No. 10/004,695, Notice of Allowance mailed Apr. 13, 2004", 7 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Notice of Allowance mailed Mar. 12, 2007", 4 pgs.

"U.S. Appl. No. 10/745,302, Response filed Jun. 26, 2006 to Non Final Office Action mailed Mar. 14, 2006", 16 pgs.

"U.S. Appl. No. 10/745,302, Response filed Sep. 12, 2005 to Restriction Requirement mailed Aug. 12, 2005", 6 pgs.

"U.S. Appl. No. 10/745,302, Response filed Dec. 14, 2006 to Non Final Office Action mailed Sep. 14, 2006", 13 pgs.

"U.S. Appl. No. 10/745,302, Response filed Dec. 23, 2005 to Non Final Office Action mailed Sep. 23, 2005", 15 pgs.

"U.S. Appl. No. 10/745,302, Restriction Requirement mailed Aug. 12, 2005", 7 pgs.

"U.S. Appl. No. 11/300,242, Final Office Action mailed Aug. 4, 2009", 9 pgs.

"U.S. Appl. No. 11/300,242, Non-Final Office Action mailed Mar. 27, 2008", 8 pgs.

"U.S. Appl. No. 11/300,242, Response filed Feb. 4, 2010 to Final Office Action mailed Aug. 4, 2009", 11 pgs.

"U.S. Appl. No. 11/300,242, Response filed Apr. 2, 2009 to Restriction Requirement mailed Dec. 15, 2008", 8 pgs.

"U.S. Appl. No. 11/300,242, Response filed Sep. 26, 2008 to Non-Final Office Action mailed Mar. 27, 2008", 10 pgs.

"U.S. Appl. No. 11/300,242, Restriction Requirement mailed Dec. 15, 2008", 10 pgs.

"U.S. Appl. No. 11/300,611, 312 Amendment filed Feb. 9, 2009", 9 pgs.

"U.S. Appl. No. 11/300,611, Non-Final Office Action mailed Mar. 20, 2008", 7 pgs.

"U.S. Appl. No. 11/300,611, Notice of Allowance mailed Jan. 26, 2009", 7 pgs.

"U.S. Appl. No. 11/300,611, PTO Response to 312 Amendment mailed Feb. 26, 2009", 3 pgs.

"U.S. Appl. No. 11/300,611, Response filed Sep. 22, 2008 to Non-Final Office Action mailed Mar. 20, 2008", 12 pgs.

"U.S. Appl. No. 12/147,293, Response filed Feb. 8, 2011 to Restriction Requirement mailed Oct. 8, 2010", 9 pgs.

"U.S. Appl. No. 12/147,293, Restriction Requirement mailed Oct. 8, 2010", 12 pgs.

"U.S. Appl. No. 12/147,317, Non-Final Office Action mailed Dec. 28, 2010", 7 pgs.

"U.S. Appl. No. 12/147,339, Notice of Allowance mailed Mar. 30, 2011", 9 pgs.

"U.S. Appl. No. 12/147,339, Notice of Allowance mailed Dec. 22, 2010", 8 pgs.

"U.S. Appl. No. 12/147,339, Response filed Oct. 20, 2010 to Restriction Requirement mailed Oct. 8, 2010", 7 pgs.

"U.S. Appl. No. 12/147,339, Restriction Requirement mailed Oct. 8, 2010", 7 pgs.

"U.S. Appl. No. 12/147,356, Notice of Allowance mailed Feb. 10, 2011", 17 pgs.

"U.S. Appl. No. 12/147,356, Response filed Nov. 10, 2010 to Restriction Requirement mailed Oct. 12, 2010", 9 pgs.

"U.S. Appl. No. 12/147,356, Restriction Requirement mailed Oct. 12, 2010", 7 pgs.

"U.S. Appl. No. 12/147,369, Non-Final Office Action mailed Sep. 10, 2010", 10 pgs.

"U.S. Appl. No. 12/147,369, Response filed Feb. 10, 2011 to Non Final Office Action mailed Sep. 10, 2010", 7 pgs.

"U.S. Appl. No. 12/147,376, Non-Final Office Action mailed Sep. 15, 2010", 9 pgs.

"U.S. Appl. No. 12/147,376, Response filed Feb. 15, 2011 to Non Final Office Action mailed Sep. 15, 2010", 9 pgs.

"U.S. Appl. No. 12/147,425, Non-Final Office Action mailed Sep. 15, 2010", 10 pgs.

"U.S. Appl. No. 12/147,425, Notice of Allowance mailed Apr. 19, 2011", 8 pgs.

"U.S. Appl. No. 12/147,425, Response filed Feb. 15, 2011 to Non Final Office Action mailed Sep. 15, 2010", 8 pgs.

"Atrostim Phrenic Nerve Stimulator", Product Brochure, AtroTech Oy, P.O. Box 28, FIN-33721 Tampere, Finland, (Jun. 2004), 2 pgs.

"Australian Application Serial No. 2005319498, First Examiner Report mailed May 27, 2010", 3 pgs.

"Australian Application Serial No. 2005319498, Response filed Feb. 21, 2011 to First Examiner Report mailed May 27, 2010", 11 pgs.

"European Application Serial No. 05849548.2, Communication and Supplementary Partial European Search Report mailed Feb. 29, 2008", 8 pgs.

"European Application Serial No. 05849548.2, Communication mailed Jun. 9, 2009", 3 pgs.

"European Application Serial No. 05849548.2, Office Action mailed Dec. 20, 2010", 4 pgs.

"European Application Serial No. 05849548.2, Response filed Dec. 16, 2009 to Communication mailed Jun. 9, 2009", 10 pgs.

"European Application Serial No. 08772198.1, Office Action mailed Sep. 13, 2010", 6 pgs.

"European Application Serial No. 08781107.1, Invitation Pursuant to Rule 63(1) EPC mailed Jul. 13, 2010", 3 pgs.

"European Application Serial No. 08781107.1, Communication dated Feb. 9, 2010", 2 pgs.

"European Application Serial No. 08781107.1, Extended European Search Report mailed Nov. 25, 2010", 6 pgs.

"European Application Serial No. 08781107.1, Response filed Mar. 5, 2010 to Communication dated Feb. 9, 2010", 2 pgs.

"European Application Serial No. 08781107.1, Response filed Sep. 22, 2010 to the Invitation to Rule 63(1)", 11 pgs.

"European Application Serial No. 08796045.6, European Search Report mailed Sep. 21, 2010", 6 pgs.

"International Application Serial No. PCT/US05/45044, International Search Report mailed May 2, 2006", 1 pg.

"International Application Serial No. PCT/US05/45044, Written Opinion mailed May 2, 2006", 3 pgs.

"International Application Serial No. PCT/US08/68618, International Search Report mailed Nov. 26, 2008", 2 pgs.

"International Application Serial No. PCT/US08/68618, Written Opinion mailed Nov. 26, 2008", 6 pgs.

"International Application Serial No. PCT/US08/68627, International Search Report mailed Sep. 10, 2008", 1 pg.

"International Application Serial No. PCT/US08/68627, Written Opinion mailed Sep. 10, 2008", 4 pgs.

"International Application Serial No. PCT/US08/68630, International Search Report mailed Sep. 10, 2008", 1 pg.

"International Application Serial No. PCT/US08/68630, Written Opinion mailed Sep. 10, 2008", 4 pgs.

"International Application Serial No. PCT/US08/68632, International Search Report mailed Sep. 11, 2008", 2 pgs.

"International Application Serial No. PCT/US08/68632, Written Opinion mailed Sep. 11, 2008", 4 pgs.

"International Application Serial No. PCT/US08/68647, International Search Report mailed Sep. 22, 2008", 2 pgs.

"International Application Serial No. PCT/US08/68647, Written Opinion mailed Sep. 22, 2008", 4 pgs.
"International Application Serial No. PCT/US08/68654, International Search Report mailed Sep. 22, 2008", 2 pgs.
"International Application Serial No. PCT/US08/68654, Written Opinion mailed Sep. 22, 2008", 4 pgs.
"International Application Serial No. PCT/US2008/068635, International Search Report mailed Sep. 9, 2008", 3 pgs.
"International Application Serial No. PCT/US2008/068635, Written Opinion mailed Sep. 9, 2008", 4 pgs.
"International Application Serial No. PCT/US2009/060293, International Search Report mailed Mar. 10, 2010", 6 pgs.
"International Application Serial No. PCT/US2009/060293, Invitation to Pay Additional Fee mailed Dec. 18, 2009", 5 pgs.
"International Application Serial No. PCT/US2009/060293, Written Opinion mailed Mar. 10, 2010", 10 pgs.
"Japanese Application Serial No. 2007-548289, Office Action mailed Nov. 24, 2010", (w/ English Translation), 7 pgs.
Alboni, P., "Bundle Branch Blocks Anatomically Located in the His Bundle", Italian Cardiology Journal, 10(12), (w/ English Translation thereof, followed by Italian publication), (1980), 1583-1587.
Barba-Pichardo, Rafael, et al., "Permanent His-Bundle Pacing in Patients With Infra-Hisian Atrioventricular Block", Rev Esp Cardiol. 59(6), (Mar. 9, 2006), 553-558.
Bonanno, C., et al., "Effect on QRS Duration and Feasibility of Septal and Multisite Right Ventricular Pacing", Cardiostimolazione, 14(3), (Abstract Only), (Sep. 1996), p. 195.
Buckingham, Thomas A., et al., "Acute Hemodynamic Effects of Atrioventricular Pacing at Differing Sites in the Right Ventricle Individually and Simultaneously", PACE, 20[Pt. I], (Apr. 1997), 909-915.
Cantu, F., et al., "Validation of Criteria for Selective His Bundle and Para-Hisian Permanent Pacing", PACE, vol. 29, (Dec. 2006), 1326-1333.
Cantu, Francesco, et al., "A Methodical Approach to Validate Selective His Bundle and para-Hisian Permanent Pacing", [abstract] Oasis, (2006), 1 pg.
Catanzariti, Domenico, et al., "Permanent His Bundle Pacing Does Not Induce Ventricular Dyssynchrony. An Echocardiographic Intrapatient Study of Comparison with Conventional Pacing", [abstract] Oasis, (2006), 1 pg.
Chudzik, Michal, "Ventricular Endocardial Right Bifocal Stimulation in Treatment of Severe Dilated Cardiomyopathy Heart Failure in Patients with Unsuccessful Biventricular Pacemaker Implantation", [abstract CP07] Europace Supplements, vol. 7, (May 2005), 1 pg.
Deshmukh, Pramod M., et al., "Direct His-Bundle Pacing: Present and Future", PACE, vol. 27, Part II, (Jun. 2004), 862-870.
El-Sherif, N., et al., "Normalization of Bundle Branch Block Patterns by Distal His Bundle Pacing: Clinical and Experimental Evidence of Longitudinal Dissociation in the Pathologic His Bundle", Circulation, 57(3), (Mar. 1978), 473-483.
Furman, S., et al., "Chapter 5—Permanent Pacemaker Implementation", A Practice of Cardiac Pacing, Futura Publishing Co., Inc. Mount Kisco, NY, (1986), 97-127.
Golia, P., et al., "Multisite Pacing of Right Ventricle in Heart Failure: Echocardiographic Evaluation", [Abstract] Cardiostimolazione, vol. 14, No. 3, (Sep. 1996), 5 pgs.
Grosfeld, M. J.W., et al., "Testing a New Mechanism for Left Interventricular Septal Pacing: The Transseptal Route", Europace, vol. 4, (Oct. 2002), 439-444.
Hummel, J. D., et al., "Augmentation of Cardiac Output by Anodal Pacing", [Abstract] Circulation, 90(No. 4, Part 2), (Oct. 1994), p. I-69.
Kavanagh, K. M., et al., "Monophasic Versus Biphasic Cardiac Stimulation: Mechanism of Decreased Energy Requirements", PACE, vol. 13, No. 10, (Oct. 1990), 10 pgs.
Kutarski, A., et al., "Factors Influencing Differences of RVA & RVOT Pacing Hemodynamic Effects", [abstract CP05] Europace Supplements, vol. 7, (May 2005), p. 288.
Kutarski, A., et al., "Right Ventricular Outflow Tract and Dual Site Right Ventricular Pacing—the Comparison With Apex Pacing", [abstract CP08] Europace Supplements, vol. 7, (May 2005), p. 288.

Lazarus, A., et al., "Reduction in Energy Pacing Thresholds by Overlapping Biphasic Stimulation Versus Conventional Bipolar Pacing", PACE, vol. 21, (Nov. 1998), 6 pgs.
Lupi, G., et al., "Effects of Right Ventricular Pacing on Intra-Left Ventricular Electromechanical Activation in Patients with Native Narrow QRS.", American Journal of Cardiology, vol. 98, (2006), 219-222.
Manolis, Antonis S., "The Deleterious Consequences of Right Ventricular Apical Pacing: Time to Seek Alternate Site Pacing", PACE, vol. 29, (Mar. 2006), 298-315.
Mond, Harry G., et al., "The Right Ventricular Outflow Tract: The Road to Septal Pacing", PACE, vol. 30, (Apr. 2007), 482-491.
Morina-Vazquez, Pablo, et al., "Cardiac Resynchronization Through Selective His Bundle Pacing in a Patient with the So-Called InfraHis Atrioventricular Block", PACE, vol. 28, (Jul. 2005), 726-729.
Narula, O. S., "Longitudinal Dissociation in the His Bundle. Bundle Branch Block Due to Asynchronous Conduction Within the His Bundle in Man", Circulation, 56(6), (Dec. 1977), 996-1006.
Occhetta, E., et al., "Prevention of Ventricular Desynchronization by Permanent Para-Hisian Pacing After Atrioventricular Node Ablation in Chronic Atrial Fibrillation: A Crossover, Blinded, Randomized Study Versus Apical Right Ventricular Pacing", Journal of the American College of Cardiology, 47(10), (May 16, 2006), 1938-1945.
Padeletti, Luigi, et al., "Physiologic Pacing: New Modalities and Pacing Sites", PACE, vol. 29, Supplement 2, (Dec. 2006), S73-S77.
Pastore, G., et al., "Different Degree of Ventricular Dyssyncrony Induced by Right Apical, Hissian and Para Hissian Ventricular Pacing", [abstract] Oasis, (2006), 1 pg.
Pastore, Gianni, et al., "Direct His-Bundle Pacing Preserves the Normal Left Activation Sequence: An Acute Echocardiographic Study", [abstract] Oasis, (2006), 1 pg.
Puech, P., et al., "Narrowing and normalization of QRS stimulation of the His bundle in complete left bundle branch block.", Scholarly Journal of the French Cardiology Society, vol. 72, No. 8, (w/ English Translation thereof, followed by French publication), (Aug. 1979), 815-824.
Ravazzi, A., et al., "Improvement of Interventricular Activation Time Using Biphasic Pacing Pulses at Different Sites on Right Ventricle Septal Wall", Progress in Biomedical Research, 4(3), (Jun. 1999), 248-253.
Reddy, G. S., "Bundle of His Stimulation System", U.S. Appl. No. 61/045,168, filed Apr. 15, 2008, 37 pgs.
Saksena, S., et al., "Chapter 9—Pacemaker Implantation Techniques", Electrical Therapy for Cardiac Arrhythmias, W.B. Saunders Co., Philadelphia, PA, (1990), pp. 173, 181-183.
Scheinman, M. M., et al., "Long-Term His-Bundle Pacing and Cardiac Function", Circulation, 101(8), (2000), 836-837.
Schoenfeld, M. H., "Alternative Site Pacing to Promote Cardiac Synchrony: Has Conventional Pacing Become Unconventional?", Journal of the American College of Cardiology, 47(10), (2006), 1946-1948.
Sotobata, I., et al., "Population distribution of Frank-vectorcardiographic measurements of healthy Japanese men", Japanese Circulation Journal, 39(8), (1975), 895-903.
Sweeney, M. O., et al., "Adverse Effect of Ventricular Pacing on Heart Failure and Atrial Fibrillation Among Patients with Normal Baseline QRS Duration in a Clinical Trial of Pacemaker Therapy for Sinus Node Dysfunction", Circulation, 107(23), (2003), 2932-2937.
Sweeney, M. O., et al., "Heart Failure During Cardiac Pacing", Circulation, 113(17), (2006), 2082-2088.
Tanabe, M., et al., "Biventricular Pacing Worsened Dyssynchrony in Heart Failure Patient with Right-Bundle Branch Block", International Journal of Cardiology, 138(3), (available online Aug. 15, 2008 / epub doi:10.1016/j.ijcard.2008.06.063 ), (2010), e47-e50.
Thakral, A, et al., "Effects of anodal vs. cathodal pacing on the mechanical performance of the isolated rabbit heart", J. Appl Physiol., 89(3), (Sep. 2000), 1159-64.
Tse, Hung-Fat, et al., "Selection of Permanent Ventricular Pacing Site: How Far Should We Go?", Journal of the American College of Cardiology, 48(8), (Sep. 26, 2006), 1649-1651.
Van Gelder, B. M., et al., "Hemodynamic Effect of RV Apex vs RV Septum Pacing in a Monoventricular and Biventricular Configuration in Patients with Heart Failure", [abstract CP06] Europace Supplements, vol. 7, (May 2005), p. 288.

Victor, F., et al., "A Randomized Comparison of Permanent Septal Versus Apical Right Ventricular Pacing: Short-Term Results", Journal of Cardiovascular Electrophysiology, 17(3), (Mar. 2006), 238-242.

Winckels, S. K. G., et al., "High-Septal Pacing Reduces Ventricular Electrical Remodeling and Proarrhythmia in Chronic Atrioventricular Block Dogs", Journal of the American College of Cardiology, 50(9), (Aug. 28, 2007), 906-913.

Zanon, Francesco, et al., "A New Technique for Direct His-Bundle Pacing: Acute and Mid-Term Electrical Data Results", [abstract] Oasis, (2006), 1 pg.

Zanon, Francesco, et al., "Direct His Bundle Pacing Preserves Coronary Perfusion Compared With Right Ventricular Apical Pacing: A Prospective, Cross-Over Mid-Term Study", Europace, vol. 10, (2008), 580-587.

Zhang, Y., et al., "His Electrogram Alternans Reveal Dual-Wavefront Inputs Into and Longitudinal Dissociation Within the Bundle of His", Circulation,104(7), (2001), 832-838.

U.S. Appl. No. 13/223,919, filed Sep. 1, 2011, Systems, Devices and Methods Relating to Endocardial Pacing for Resynchronization.

U.S. Appl. No. 13/217,776, filed Aug. 25, 2011, Systems, Devices and Methods for Monitoring Efficiency of Pacing.

U.S. Appl. No. 13/282,163, filed Oct. 26, 2011, Circuit-Based Devices and Methods for Pulse Control of Endocardial Pacing in Cardiac Rhythm Management.

U.S. Appl. No. 13/216,969, filed Aug. 24, 2011, Endocardial Pacing Relating to Conduction Abnormalities.

U.S. Appl. No. 13/094,416, filed Apr. 26, 2011, His-Bundle Capture Verification and Monitoring.

U.S. Appl. No. 13/139,951, filed Jan. 6, 2012, Devices, Methods, and Systems Including Cardiac Pacing.

"U.S. Appl. No. 12/147,376, Notice of Allowance mailed Dec. 7, 2012", 7 pgs.

"U.S. Appl. No. 12/249,454, Notice of Allowance mailed Dec. 26, 2012", 5 pgs.

"U.S. Appl. No. 12/249,454, Response filed Dec. 4, 2012 to Non Final Office Action mailed Sep. 4, 2012", 12 pgs.

"U.S. Appl. No. 12/249,479, Notice of Allowance mailed Jan. 8, 2013", 5 pgs.

"U.S. Appl. No. 12/249,479, Response filed Dec. 4, 2012 to Non Final Office Action mailed Sep. 4, 2012", 9 pgs.

"U.S. Appl. No. 13/094,416, Non Final Office Action mailed Dec. 14, 2012", 13 pgs.

"U.S. Appl. No. 13/217,776, Non Final Office Action mailed Jan. 15, 2013", 6 pgs.

"European Application Serial No. 05849548.2, Office Action mailed Jan. 16, 2013", 3 pgs.

"International Application Serial No. PCT/US2011/033944, International Preliminary Report on Patentability mailed Nov. 8, 2012", 9 pgs.

"International Application Serial No. PCT/US2012/026571, International Search Report mailed Oct. 18, 2012", 4 pgs.

"International Application Serial No. PCT/US2012/026571, Written Opinion mailed Oct. 18, 2012", 7 pgs.

"Japanese Application Serial No. 2007-548289, Office Action mailed Nov. 6, 2012", With English Translation, 3 pgs.

"Japanese Application Serial No. 2007-548289, Response filed Feb. 4, 2013 to Office Action mailed Nov. 6, 2012", With English Claims, 7 pgs.

"Japanese Application Serial No. 2010-515189, Office Action mailed Feb. 12, 2013", With English Translation, 9 pgs.

"Japanese Application Serial No. 2010-515196, Office Action mailed Jan. 15, 2013", With English Translation, 8 pgs.

"Japanese Application Serial No. 2010-515198, Office Action mailed Feb. 12, 2013", With English Translation, 16 pgs.

"Japanese Application Serial No. 2011-531237, Office Action mailed Jan. 15, 2013", With English Translation, 7 pgs.

"Japanese Application Serial No. 2011-542513, Office Action mailed Jan. 15, 2013", With English translation, 6 pgs.

US 6,875,206, 04/2005, Ponzi (withdrawn)

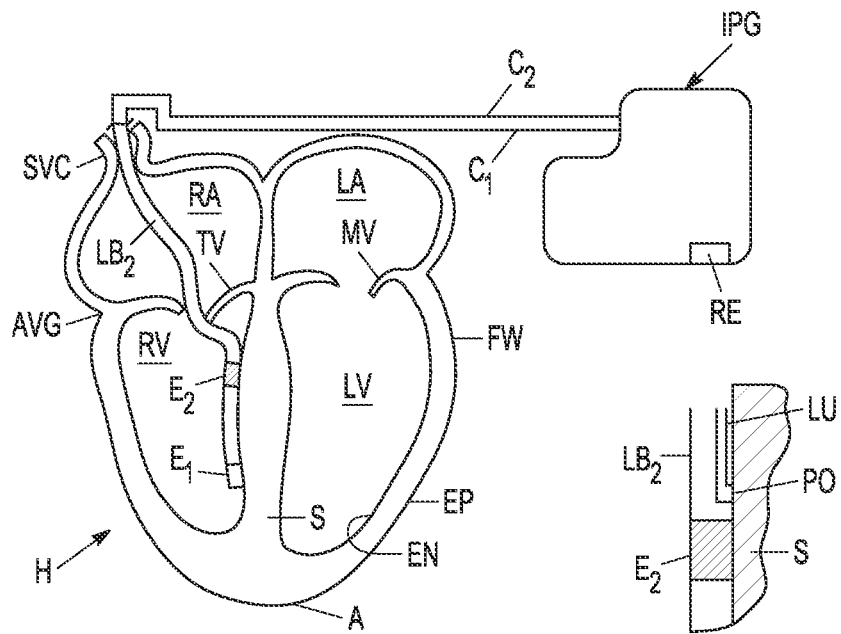
FIG. 2
FIG. 2A
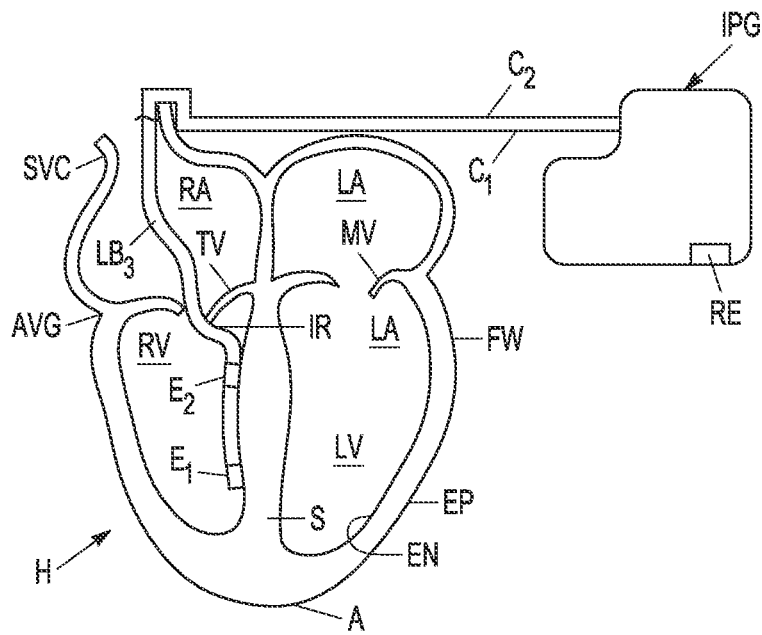
FIG. 3

ENDOCARDIAL PACING DEVICES AND METHODS USEFUL FOR RESYNCHRONIZATION AND DEFIBRILLATION

CLAIM OF PRIORITY

This application is a continuation of and claims the benefit of priority under 35 U.S.C. §120 to Zhu et al., U.S. patent application Ser. No. 12/147,425, entitled "Endocardial Pacing Devices And Methods Useful For Resynchronization And Defibrillation," filed on Jun. 26, 2008, now U.S. Pat. No. 8,005,544, which is hereby incorporated by reference herein in its entirety.

This patent document claims the benefit, under 35 U.S.C. §119(e), of U.S. Provisional Patent Applications concurrently filed on Jun. 29, 2007 and identified by the following Ser. Nos. 60/947,308 (Endocardial Pacing For Resynchronization), and 60/947,336 (Endocardial Pacing For Resynchronization And Defibrillator). This patent document is also a continuation-in-part of and claims priority under 35 U.S.C. §120 both to U.S. patent application Ser. No. 11/300,611, filed Dec. 13, 2005 (Ventricular Pacing) to Daniel Felipe Ortega et al. (AMED.002PA), now U.S. Pat. No. 7,512,440, and to U.S. patent application Ser. No. 11/300,242, filed Dec. 13, 2005 (Pacemaker Which Reestablishes Or Keeps The Physiological Electric Conduction Of The Heart And A Method Of Application) to Daniel Felipe Ortega et al. (AMED.003PA), now U.S. Pat. No. 8,346,358, which in turn claim priority to Argentine Patent Application Ser. No. 20040104782, filed Dec. 20, 2004 (A New Pacemaker Which Reestablishes Or Keeps The Physiological Electric Conduction Of The Heart And A Method Of Application), to Daniel Felipe Ortega et al. Each of these patents documents is incorporated by reference in their entirety.

FIELD OF THE INVENTION

This invention generally relates to systems, devices and methods relating to cardiac monitoring and treatments such as ventricular pacing. More particular aspects of this invention specifically concern use of circuits for achieving mechanically and/or electrically synchronous contractions while pacing of a patient's left and right ventricles by one or more electrodes residing in the patient's right ventricle.

BACKGROUND

Pacemakers are perhaps the most well known devices that provide chronic electrical stimulus, such as cardiac rhythm management. Pacemakers have been implanted for medical therapy. Other examples of cardiac stimulators include implantable cardiac defibrillators (ICDs) and implantable devices capable of performing pacing and defibrillating functions. Such implantable devices provide electrical stimulation to selected portions of the heart in order to treat disorders of cardiac rhythm. An implantable pacemaker paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some pacing devices synchronize pacing pulses delivered to different areas of the heart in order to coordinate the contractions. Coordinated contractions allow the heart to pump efficiently while providing sufficient cardiac output. Clinical data has shown that cardiac resynchronization, achieved through synchronized biventricular pacing, results in a significant improvement in cardiac function. Cardiac resynchronization therapy improves cardiac function in heart failure patients. Heart failure patients have reduced autonomic balance, which is associated with LV (left-ventrical) dysfunction and increased mortality.

Commonly treated conditions relate to the heart beating too fast or too slow. When the heart beats too slow, a condition referred to as bradycardia, pacing can be used to increase the intrinsic heart rate. When the heart beats too fast, a condition referred to as tachycardia, pacing can be used to reduce the intrinsic heart rate by, for example, inhibiting electrical signals used to generate a contraction of the heart.

When pacing for bradycardia, percutaneously placed pacing electrodes are commonly positioned in the right-side chambers (right atrium or right ventricle) of the heart. Access to such chambers is readily available through the superior vena cavity, the right atrium and then into the right ventricle. Electrode placement in the left ventricle is normally avoided, where access is not as direct as in right ventricle placement. Moreover, emboli risk in the left ventricle is greater than in the right ventricle. Emboli which might develop in the left ventricle by reason of the electrode placement have direct access to the brain via the aorta from the left ventricle. This presents a significant risk of stroke. Pacing of both the right atrium and right ventricle was developed. Such dual chamber pacing resulted in better hemodynamic output than right ventricle-only pacing. In addition to treating bradycardia, dual chamber pacing maintained synchrony between the chambers.

Recent clinical evidence suggests that conventional ventricular pacing from the right ventricle creates asynchronous contraction of the left and right ventricles, thereby resulting in inefficient mechanical contraction and reduced hemodynamic performance. Long term right ventricular pacing has even been found to be associated with an increased risk of developing or worsening heart failure.

SUMMARY

The present invention is directed to use of a device and method for overcoming the above-mentioned challenges and others. The present invention is exemplified in a variety of implementations and applications, many of which involve tools and methods helpful, or particularly suited, for certain cardiac conditions advantaged by ventricular pacing, as exemplified by ventricular pacing of the right and left ventricles from a lead in the right ventricle and as may be used, among other applications, to facilitate mechanically and/or electrically synchronous contractions for resynchronization.

According to one aspect, the present invention is directed to various methods and apparatus for modifying cardiac operation, for treating a condition of a patient's heart, and for monitoring cardiac operation. In one approach consistent with certain of these disclosed methods and apparatus, an electrode arrangement (including at least one electrode) is placed in a right ventricle ("RV") of the heart. The electrode arrangement is used to capture the myocardium for re-synchronization of the left and right ventricles by providing first and second signal components having opposite polarity on respective electrodes. The electrode arrangement connected to an implantable CRM device that has the capability of pacing/sensing atrium, pacing/sensing ventricles, and deliver defibrillation therapy from the right side of the heart. The CRM device captures ventricular contractions to treat conduction abnormalities in one or more of the ventricles.

In a specific example embodiment, a myocardium capture is achieved by a circuit arrangement that delivers pacing signals via electrodes to a target region in the right ventricle, near the septum of a heart and distal from an apex of the right ventricle. The circuit arrangement includes: first and second conductors, respectively coupled to the electrodes, for providing pacing signals of opposing polarity to the target region, and a third conductor for providing a defibrillation signal to the right ventricle apex; and a control module for generating the pacing signals, with two pulses occurring sufficiently proximate one another for the myocardium capture near the target region, on the first and second conductors and for generating the defibrillation signal.

Various embodiments involving use of a defibrillation lead may be particularly useful as the lead need not contain pacing/sensing electrodes, thereby eliminating or lessening the pullback of the RV coil, which has been known to lower the defibrillation threshold.

Some aspects of the present invention, presented herein as mere examples and without limitation, are useful for pacing and/or mapping by generating pulses for delivery to a cardiac site to improve heart function. According to certain aspects of the present invention, a pulse generator includes circuitry for generating pacing profiles, with signals of opposite polarities, specifically selected for delivery by one or more electrodes at a site near the septal wall of a right ventricle of the heart.

Certain aspects involve pacing and/or mapping by generating such pulses to a cardiac site useful for improving heart function as measured, e.g., by QRS width, fractionation, late LV activation timing, mechanical synchronicity of free wall and septal wall, effective throughput/pressure, or a combination thereof. In one embodiment, a circuit arrangement includes leads, electrically coupled to the electrodes, for providing pacing signals of opposing polarity to the heart tissue, and a tip and ring control module for generating pulse waveforms of opposing polarities to drive control module leads (connecting to the electrodes) with an electrical pacing signal that includes two pulses occurring sufficiently proximate one another for the myocardium capture near the target region.

In specific applications and embodiments, this heart function is measured by QRS width, fractionation, late LV activation timing, mechanical synchronicity of free wall and septal wall, effective throughput/pressure, and by any combination thereof.

Other specific applications and aspects, which can be implemented alone or in combination, include: determining a pacing (voltage) threshold, beyond the capture threshold, to improve heart function; delivering pulses of opposite polarity to achieve such heart-function improvement; bi-ventricular pacing from a lead in the right ventricle for such improved heart function; delivering pulses of opposite polarity at a site near the His bundle; electrode-based His-pacing, without penetrating the myocardium; generating and/or delivering multiple pacing profiles, e.g., by iterating through different pacing profiles, including a pacing profile that delivers pulses of opposite polarity and another pacing profile; delivering a pacing profile to generate a synchronous contraction of the septal wall and free wall of the LV from a RV (right-ventricle) pacing location; and treating one or more of distal LBBB (left bundle branch block) and/or diffuse LBBB by pacing at a site near the His bundle.

The skilled artisan will appreciate that the His bundle is also known as the atrioventricular (AV) bundle and previously characterized as an area of heart muscle cells that provide electrical conduction for transmitting the electrical impulses from an area near the AV node (located between the atria and the ventricles). In connection with implementations of the present invention, it has been discovered that certain cells in and around the His bundle can be manipulated to respond to certain electrical stimulus in unexpected ways. Some aspects and implementations of the present invention facilitate modulation of the His bundle to improve the heart condition in unexpected ways.

Implementations of the present invention take a wide variety of forms, e.g., ranging from devices, systems, methods of using and manufacturing such devices and systems, to computer-accessible data (computer executable instructions and other input and output data) useful for implementing such methods, devices and systems. Many of these implementations involve such tools and steps relating to the above-listed aspects.

As specific examples of other such implementations, the present invention can be implemented in the form of methods, devices and arrangements of devices for monitoring cardiac operation and modifying cardiac operation, e.g., for cardiac treatment. In one such specific example embodiment, one or more of the above aspects involves use of an implantable pulse generator and placement of an electrode arrangement (including at least one electrode) in a RV of the heart for capturing the myocardium for re-synchronization of the left and right ventricles. This is achieved by providing first and second signal components having opposite polarity, as generated by the implantable pulse generator, on respective electrodes. The contraction of the heart is monitored and used in selecting the waveforms (including for example, waveforms of opposing polarities) and in determining the position of the electrodes. In more specific embodiments, the electrode arrangement is located in the sweet spot (locus) for achieving resynchronization, in the septal part of the RV endocardium. Anodal pacing of one of the electrodes can be used with respect to a reference voltage in the body of the patient to achieve resynchronization or a synchronous contraction during pacing of the heart. Polarities may be switched as appropriate (e.g., once every few hours) to avoid anodal block (the rise of stimulation thresholds that occurs after continuous anodal stimulation at the anodal electrode).

In other specific examples, implementations involve pacing from the right ventricle to treat LBBB, diffuse-distal block characterized by large QRS width (e.g., QRS>120 ms) and fractionated ECG (electrocardiograph or electrocardiogram) signals. Consistent therewith, a specific method involves the use of a pacing profile having opposite-polarity pulses (relative to body common) delivered for a cardiac capture (defined as the presence of contractions in the heart in direct response to electrical stimulation signals from an external source). In various contexts, such a pacing profile is referred to herein as an "Xstim" pacing profile or simply as Xstim.

One such Xstim pacing profile includes the use of two electrodes that are oppositely charged with respect to a reference electrode. In various implementations, the electrodes are spatially disparate. The pulses can be provided, relative to one another, in phase, out of phase, offset and overlapping, offset not overlapping with no delay between pulses, offset not overlapping with a delay between pulses or biphasic with a single electrode near the His bundle.

According to yet other embodiments, the present invention involves pacing at a location that is determined as follows. An intrinsic or baseline ECG reading is taken. A pacing lead is placed in the RV near the bundle of His. A pacing signal is delivered to the pacing lead. In a specific instance, the pacing signal is an Xstim pacing profile. A pacing ECG signal is taken. Comparisons are made between one or more of the QRS width, fractionated QRS and the timing of a late activated region of LV relative to the QRS. The position of the probe is changed and the pacing and comparison steps are repeated as necessary. The lead can then be fixed at the appropriate location.

In other embodiments, the present invention involves selection of a pacing profile and placing a lead in the RV at or near the His bundle to deliver a plurality of pacing profiles. Heart function is recorded (e.g., using an ECG), and a suitable pacing profile is then selected for treatment.

According to another embodiment, pacing devices and methods of using such devices involve a catheter that delivers a lead that has two electrodes. In certain implementations thereof, the catheter is adapted to contact near the His bundle. A pacing profile (with two opposite voltages, referenced to body common) is delivered to the electrodes. The electrodes are individually addressable (i.e., capable of providing distinct signals) and spatially disparate. In a specific instance, one electrode is located at or near the distal tip of the lead and the other is located between the distal tip and the proximal end of the lead. Some embodiments allow for the use of more than two electrodes. Also, one or more electrodes may be used to sense heart function.

According to another embodiment, a catheter is adapted and used to facilitate adjustment of the location along the septal wall of the right ventricle. The catheter is designed for delivering a pacing profile and for subsequent adjustment of a delivery site for the pacing profile. This embodiment can be useful for a pace-sense-adjust procedure which, in some instances, is iterated until a location is determined for achieving the improved heart function.

As previously indicated, the above-discussed aspects and examples and not to be treated as limiting the scope or teachings of the disclosure herein. The skilled artisan would appreciate that, partly based on the various discoveries identified herein, the present invention can be embodied in many ways including but not limited to the above the above-discussed aspects and examples.

BRIEF DESCRIPTION OF THE DRAWINGS

The present invention may be more completely understood in consideration of a detailed discussion of various example embodiments, described in accordance with the present invention, as presented hereinafter in connection with the following figures, each of which is consistent with the present invention:

FIG. 2 is the view of FIG. 1 showing electrodes in contact with a septal wall;

FIG. 2A is a cross-sectional view of an electrode lead showing a mechanism for attachment of an electrode to a septal wall;

FIG. 3 is the view of FIG. 1 showing an electrode lead formed, in part, from shape memory alloys for urging electrodes against a septal wall;

FIGS. 23A, 23B, 23C and 23D depict a graphical representation of pulse to be applied by the electrodes of the various embodiments;

Figure 1:
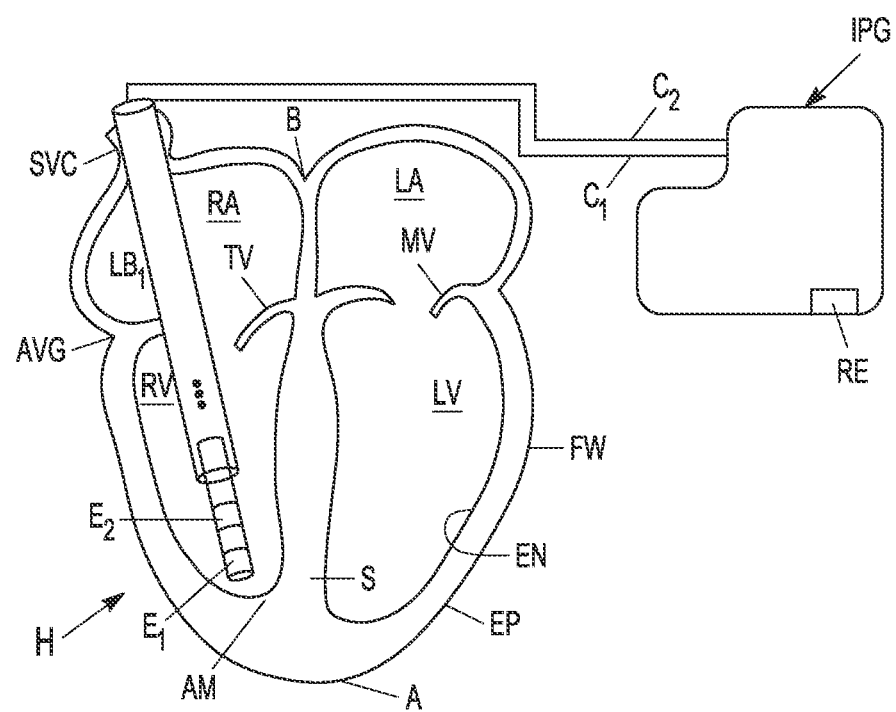
FIG. 1 is a schematic cross-sectional view of the heart showing relevant anatomical features and schematically showing a catheter with pacing electrodes in the right ventricle and a subcutaneously placed implantable pulse generator.

While the invention is amenable to various modifications and alternative forms, various embodiments have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and approaches, and the invention has been found to be particularly suited for approaches to pacing of the right and left ventricles from a lead in the right ventricle. In certain implementations, the invention is used to facilitate mechanically and/or electrically synchronous contractions for resynchronization (possibly due to conduction abnormalities such as LBBB) where the left ventricle has regained its ability to rapidly contract and/or to synchronize contractions of cardiac muscle of the septum and respective free wall(s). While the present invention is not necessarily limited to such applications, various aspects of the invention may be appreciated through a discussion of various examples using this context.

Consistent with specific embodiments and various discoveries realized in connection with the present invention, heart function can be improved by pacing and/or mapping by delivering pulses to a cardiac site, where the heart function is indicated or measured, e.g., by QRS width, fractionation, late LV activation timing, mechanical synchronicity of free wall and septal wall, effective throughput/pressure, and/or by any combination thereof. Certain methods and specific aspects consistent with such embodiments of the present invention concern the generation of selected waveforms for delivering pulses to a cardiac site where the improved heart function involves: determining a pacing (voltage) threshold, beyond the capture threshold, to improve heart function; delivering pulses of opposite polarity to achieve such heart-function improvement; bi-ventricular pacing from a lead in the right ventricle for such improved heart function; delivering pulses of opposite polarity at a site near the His bundle; electrode-based His-pacing, without penetrating the myocardium; generating and/or delivering multiple pacing profiles, e.g., by iterating through different pacing profiles, including a pacing profile that delivers pulses of opposite polarity and another pacing profile; delivering a pacing profile to generate a synchronous contraction of the septal wall and free wall of the LV from a RV (right-ventricle) pacing location; and treating one or more of distal LBBB (left bundle branch block) and/or diffuse LBBB by pacing at a site near the His bundle.

As a specific example of an unexpected result, it has been discovered that His bundle pacing and/or para-Hisian pacing can be used to treat patients exhibiting a variety of cardiac abnormalities previously thought to be unsuitable for His bundle pacing (e.g., large QRS complexes due to distal left bundle blocks or diffuse left bundle blocks). It has also been discovered that implantation complexities (e.g., duration and/or invasiveness) can be beneficially affected by the use of specific devices, systems and placement methods.

According to an example embodiment of the present invention, a specialized stimulation profile is used to capture a synchronous contraction of the left and right ventricles. The stimulation profile is provided to a lead in the right ventricle. The lead placement and stimulation profile are selected in response to sensed heart function during the pacing. In particular, the lead placement and stimulation profile are determined based upon more than whether the placement/profile results in capture (e.g., QRS width or late activation site timing). In certain instances, this can result in pacing voltages/profiles not otherwise believed to be desirable (e.g., voltages derived from criteria other than the capture threshold and/or His bundle pacing without penetrating the surrounding (fibrous) tissue with a pacing lead).

The understanding of various implementations of the present invention can be facilitated with a discussion of existing pacing, implantation and related procedures and devices. While a substantial number of differences exist between various embodiments of the present invention and such existing pacing, the present invention does not exclude implementations that include aspects of existing pacing. Quite to the contrary, aspects of the present invention are particularly useful for implementing in conjunction with existing pacing methods and devices. Accordingly, a number of embodiments of the present invention provide the flexibility to be useful when combined with existing implementations, some of which are discussed hereafter.

Combined pacing of the right ventricle and right atrium has been performed by advancing two electrode leads through the superior vena cava into the right atrium. The first of these terminated at one or more electrodes which were attached to the endocardium of the atrium. The second lead (also having one or more electrodes) was advanced into the right ventricle with the electrode attached to the endocardium of the right ventricle.

Such dual chamber pacing was not without complications. The use of two leads resulted in a doubling of volume of the vasculature (e.g., the superior vena cava and jugular vein) occupied by such leads. Further, attachment of an electrode to the atrial wall was unreliable.

The problems of the dual chamber pacing led to the development of so-called "single pass" leads. Such leads have both the atrial and ventricle electrodes on a common lead.

An example of a single pass lead, for pacing both the right ventricle and right atrium, is taught in U.S. Pat. No. 6,230,061 B1 to Hartung issued May 8, 2001. The lead of the '061 patent is described as a floating lead in that the lead and electrodes are not attached to the walls of the heart. In one embodiment of the '061 patent (FIG. 4A), two electrodes in the right atrium pace the right atrium. In a second embodiment (FIG. 4B), an electrode resides in the right ventricle to add right ventricular pacing. As will be described, the '061 patent describes an oppositely polarized electrode (which may be exposed on a subcutaneously placed implantable pulse generator).

It is believed that the design of the '061 patent has not enjoyed great commercial success. This is believed to be due, at least in part, to the separate development of smaller profile leads and more reliable atrial attachment techniques. Both of these developments address the problems of dual chamber pacing otherwise addressed by the '061 patent.

When treating for tachycardia (fast heart rate), electrical pulses are used to disrupt a contraction of the heart. This may be effective at reducing the heart rate by disrupting the abnormally fast pulses generated by cardiac dysfunction tissue.

Congestive heart failure (CHF) patients suffer from low left ventricular output. CHF is an extremely serious and progressive disease. While drug treatments exist, they may delay but do not stop or reverse the disease.

CHF patients face a progression of a debilitating condition which drastically alters lifestyle and will ultimately be fatal in the absence of heart transplant. Unfortunately, many patients do not qualify for such transplants and the available number of donor hearts is inadequate to treat those who do qualify.

Many CHF patients have low left ventricular output due to a mismatch between contractile forces produced by muscles of the left and right ventricles' free wall (the external wall of the left and right ventricles) and the opposing septum (the wall dividing the right and left ventricles). Ideally, the free wall and septum contract in synchrony during systole to urge blood through the aortic valve. When out of synchrony, the septal wall may be contracting while the free wall is relaxed. Instead of urging blood flow, at least a portion of the contractile energy of the septum is wasted.

The mismatch of free wall and septal contractility is believed to be due to disorders in the electrical conduction systems of the heart. This conduction system includes the A-V node (heart tissue between the atria and the ventricles that conducts contractile impulses from the atria to the ventricles), the bundle of His and the Purkinje fibers.

Located at the upper end of the septum, the sinus node creates the synchronized neurally-mediated signal for cardiac pacing. These signals are conducted by the specialized fibers comprising the A-V node and the bundle of His (extending along the length of the septum) and further conducted to the muscle of the heart through the Purkinje fibers. The Purkinje fibers originate in the septum and extend through the apex of the heart and to the exterior walls of the heart including into and up the free wall of the left and right ventricles.

In a healthy heart, the signal flow from the A-V node to the free wall of the left and right ventricles is rapid to ensure the free wall and septum contract in synchrony. For example, a stimulating signal may flow to the free wall in about 70-90 milliseconds. In patients with conduction abnormalities, this timing may be significantly delayed (to 150 milliseconds or more) resulting in asynchronous contraction.

In some patients, the conduction path through the Purkinje fibers may be blocked. The location of the block may be highly localized (as in the case of so-called "left bundle branch block" or LBBB) or may include an enlarged area of dysfunctional tissue (which can result from infarction). In such cases, all or a portion of the free wall of the left and/or right ventricles is flaccid while the septum is contracting. In addition to contributing to asynchronous contraction, the contraction force of the free wall is weakened.

To address asynchronous contraction, CHF patients can be treated with cardiac pacing of the left ventricle. Such pacing includes applying a stimulus to the septal muscles in synchrony with stimulation applied to the muscles of the free wall of the left ventricle. While infracted tissue will not respond to such stimulus, non-infracted tissue will contract thereby heightening the output of the left ventricle by re-synchronizing the contraction. Accordingly, treatment of CHF is often directed re-synchronization of the myocardium, whereas other ventricular pacing solutions, such as tachycardia and bradycardia, treat heart rate issues.

The prior art has developed various techniques for accomplishing left ventricle stimulation. For various reasons the techniques may not be ideal. For example, such pacing may result in wide QRS complexes or emboli formation. Thus, endocardial-positioned electrodes in the left ventricle are avoided. However, electrodes can be placed on the epicardial surface of the heart through surgical placement. The epicardial electrodes are positioned on the free wall of the left ventricle and are paced in synchrony with electrodes placed near the septum in the right ventricle.

Since epicardial electrodes require a surgical placement, the patient is subjected to two procedures: percutaneous placement of right ventricle electrodes (normally performed in a catheter lab by an electrophysiologist); and surgical placement of epicardial electrodes on the left ventricle (normally placed by a cardiac surgeon in a surgical suite). Such dual procedures are a burden on medical resources.

Percutaneous procedures have been developed for placement of an electrode to stimulate the free wall of the left ventricle. In such a procedure, an electrode lead is advanced through the coronary sinus. Part of the venous system, the coronary sinus extends from the right atrium and wraps around the heart on or near the epicardial surface and partially overlies the left ventricle free wall. In this percutaneous procedure, the electrode remains positioned in the coronary sinus overlying the left ventricle free wall with the lead passing through the coronary sinus and through the right atrium to the implantable pulse generator.

Unfortunately, a coronary sinus electrode is frequently less than optimal. The portion of the free wall most directly influenced by the electrode is the tissue directly underlying the coronary vein at the location of the electrode. For many patients, this may not be the location of the free wall that benefits the most from a stimulating therapy. Accordingly, the resulting therapy is sub-optimal. Also, some patients may have an extremely small-diameter coronary sinus or the coronary sinus may have such a tortuous shape that percutaneous positioning of an electrode within the coronary sinus is impossible or very difficult. Not uncommonly, advancing a lead from the right atrium into the coronary sinus is extremely time-consuming. Even if successful, such a procedure consumes significant health care resources (including precious catheter lab time). Finally, there are now up to three leads passing through and occupying the space of the superior vena cava (i.e., leads for the electrodes in the right ventricle, right atrium and the coronary sinus). U.S. Patent application Publ. No. 2005/0125041 published Jun. 9, 2005 shows (in FIG. 1 thereof) three leads passing through a superior vena cava with one lead residing in the right atrium, one in the right ventricle and one passing through the coronary sinus to the left ventricle.

Attempts at pacing the left ventricle by pacing stimulation in the right ventricle have been suggested. U.S. Pat. No. 6,643,546 B2 to Mathis et al. dated Nov. 4, 2003 describes a lead with an array of electrodes along its length. The lead is placed in the right atrium and extended through the right ventricle, along the septal wall, and into the pulmonary artery. The concept requires that multiple electrodes from the array be pulsed simultaneously at significantly high voltages to produce an adequate electrical field to stimulate the LV septum. The current output from the pulse generator and battery will be very high due to the multiplicity of electrodes and high pacing voltages. Such high output will cause a clinically unacceptable product lifespan and may facilitate electrode corrosion and/or dissolution issues. Since a large number of electrodes and supporting electronics are needed to implement such a therapy delivery mechanism, it is not known yet whether it is practically feasible, not to mention that it is very complicated both in terms of device design/manufacturing as well as clinical practice. No published reports known to this date have demonstrated the functional as well as clinical benefits for this multiple electrode stimulation approach in the right ventricle.

As will be described with reference to one embodiment, the present invention is directed to a left ventricle pacing system and method which does not require epicardial pacing electrodes or pacing electrodes in a coronary sinus or a coronary vein. As will be described, the present invention includes electrodes in the right ventricle near the septal wall. These electrodes create a pulsed electrical field which stimulates both the septum and at least a portion of the free wall of the left and right ventricles. The present invention achieves these objectives without requiring excessive energy demands or power consumption.

Generally, the aspects of the present invention are directed to a method and apparatus for providing right-ventricle stimulation to re-synchronize a contraction of the musculature of the septum and free wall of the left and right ventricles to create coordinated contraction of the septum and free wall. Careful placement of the stimulating electrodes in the right ventricle is used to produce synchronous contractions of the left and right ventricles. In a particular instance, the right ventricle may be captured along with re-synchronization of the left and right ventricles from a single stimulus point or while maintaining the synchrony of the activation and contraction of the left and right ventricles (in the case that the patient required pacing and did not have an asynchronous contraction without pacing). Using various embodiments of the present invention, patients that have an asynchronous contraction of the heart (either the left or the right ventricles or both) can be resynchronized.

In another instance, pacing for patients having bradycardia, tachycardia or other rhythm management, may be improved by improving upon the asynchronous contraction that often occurs due to the electrical impulse artificially introduced that is not propagating through the normal conduction system of the heart (His-Purkinje system).

Consistent with embodiments and applications of the present invention, an electrode is carefully placed at the His bundle site ("His Pacing") by screwing in the electrode to get into or beside the bundle itself or by positioning the electrode at a site where the bundle gets to the endocardial surface (denoted supra as EN). Previous His pacing efforts (to maintain synchronous contractions that would be otherwise lost due to conventional RV pacing for rate support) have been very burdensome largely because finding this very small region in the right ventricle has been very difficult, and the effort is generally time-consuming, expensive and extremely complex even with modern tools and imaging techniques. Further complicating such procedures is the lack of knowledge regarding the long-term stability of placing a lead in this location. Pacing the distal segment of the His bundle has also been shown to remove left bundle block (LBBB) in patients with a proximal lesion of the bundle. His pacing, however, is currently contraindicated in patients with a distal lesion of the His bundle or with an intraventricular conduction defect (IVCD), in patients with diffuse peripheral block (at the distal His or diffuse in the Pukinje fibers), and in patients with advanced HF (NYHA class II to IV) and conduction defects. Accordingly, His pacing is used only in a very small subset (<0.01%) of the patients that require ventricular pacing for either Sick Sinus Syndrome, AV block or other Bradyarrhythmia indications by an extremely small group of physicians.

It has also been discovered that correct placement of the stimulating electrodes along the septum can sometimes allow for re-synchronization of contractions of left-ventricle myocardium using relatively low voltages and may also result in improved QRS width, reduced fractionation, and/or improved timing of a late-activation site in the LV. It has also been discovered that the region in the septum where this effect takes place is larger and easier to find when particular methods are used. One such method includes the use of a waveform herein referred to as a Xstim waveform, where two pulses of opposite polarity are applied. The Xstim waveform, generally speaking, is the application of the two pulses of opposite polarity at the same time, or nearly the same time, such that both pulses are associated with the same capture (beat) of the heart.

In many patients the pacing region is located near the location where the His bundle passes close to the endocardial surface of the right ventricle. But in patients with more diffuse block and heart failure, it may move down in the septum towards the apex of the right ventricle. It has also been discovered that careful selection of the waveform may allow for effective pacing using lower voltages, thereby simplifying the design of the output circuits in the pacemaker and the delivery electrodes. It has further been discovered that the desired pacing effect can also be achieved by a single pulse of sufficient amplitude, usually much higher than the amplitude required by the Xstim waveform, and therefore presenting a much higher risk of diaphragmatic and/or phrenic nerve stimulation. It has further been discovered that the amplitude required to achieve the effect is more often lower when that pulse is of anodal nature versus a negative pulse (referenced to the body).

In one embodiment, each electrode may be selectively and independently used to stimulate a synchronous contraction. The voltages for each electrode are varied to determine the voltage threshold necessary to produce ventricular capture. In various implementations, discussed in more detail hereafter, the voltage threshold can be determined using criteria other than (or in addition to) whether ventricular capture is produced (e.g., improved heart function). Low average stimulation voltage and current may be obtained by selecting the electrode that has the lowest effect threshold (effect refers to resynchronization effect or to maintaining synchrony of the contraction during pacing effect).

In connection with the various drawing figures and relevant discussions, the following disclosures are incorporated herein by reference in their entirety: U.S. Pat. No. 6,230,061 B1 to Hartung issued May 8, 2001, for details of a cardiac pacemaker with localization of the stimulating pulses and U.S. Pat. No. 6,907,285 to Denker, et al., dated Jun. 14, 2004, for details of a wireless defibrillation system; U.S. patent application Publ. No. 2004/0153127 published Aug. 5, 2004 for details related to the use of a microstimulator in the proximity of at least one anatomical structure to produce muscular contractions; U.S. Pat. No. 6,643,546 B2 to Mathis et al. dated Nov. 4, 2003, for details related to the treatment of congestive heart failure.

Given the hemodynamic benefit provided by Xstim pacing as described herein, a dual lead system in the RV, instead of a single lead is beneficial. For many heart failure patients Xstim pacing alone will provide sufficient benefit, making it unnecessary to implant a third lead in the left ventricular free wall. For those that still require an LV lead, the system will provide improvements over a regular BV system, given that XSTIM provides better synchronicity.

Various implementations of the present invention, depending on the patient, provide systems and methods with atrial sensing and pacing, or a simpler single chamber system. For patients that are candidates for BV (CRT), a dual chamber pacing system may be beneficial, unless they have chronic atrial fibrillation, in which case a single chamber system may be the better choice (no atrial sensing or pacing).

Accordingly, the present invention is directed to various embodiments including, for example, a single chamber Xstim pacing ICD with two leads in the right ventricle, one for shocking and another for XSTIM delivery and sensing. According to another embodiment, dual chamber XSTIM ICD with two leads in the right ventricle is implemented. Atrial pacing and sensing is added via one lead that is used for shocking, while the other is used for XSTIM delivery and sensing. Yet another embodiment involves, single chamber XSTIM ICD with two leads in the right ventricle. One lead is used for shocking, while the other is used for XSTIM delivery and sensing. Another embodiment involves a dual chamber (adding atrial pacing and sensing) XSTIM ICD with two leads in the right ventricle, one for shocking another for XSTIM delivery and sensing. A lead on the left ventricle may be provided for an improved (e.g., due to XSTIM) BV pacer with defibrillation backup implementation.

Each of these embodiments may be implemented using a variety of pacing (XSTIM) waveforms and pulse polarities. For instance, the XSTIM pulse may be implemented by periodic reversal of the pulse polarities. The periodicity of the reversals may be modified to reverse every beat, once ever N beats or may follow other, more complicated, timings. Other variations to the pulses may include the use of multiple discharge capacitors and various voltage regulation circuits to produce a desired waveform.

As mentioned above, aspects of the present invention are directed to improving heart function as indicated by one or more of several measurable characteristics. The discussion and illustrations presented in connection with FIGS. 1-32 provide examples and related results for one or more of these and other aspects of the present invention. These aspects can be implemented in various combinations. To fully appreciate some of these aspects and the related discoveries, the following discussion of FIGS. 1-32 presents related discussion as well as various features that are optional to other embodiments, such as those illustrated and discussed in connection with FIGS. 1-32.

The present invention may be practiced with currently commercially available electrode leads and can also be enhanced with specially designed leads. FIG. 1 illustrates the invention in practice with one such lead. As is the conventional usage for referencing relative direction, the terms "left" and "right" are used herein with reference to the patient's perspective. The terms "upper" and "lower" and similar terms such as "up" or "down" are used with reference to the base B of the heart being high and the apex A of the heart H being a lower end.

In connection with various embodiment of the present invention, FIG. 1 illustrates approaches for pacing of the right and left ventricles from a lead in the right ventricle in a manner consistent with the above discussed aspects. With pacing profiles (waveforms including but not limited to Xstim pacing signals) being generated by an implantable pulse generator (or IPG) and being delivered on electrodes $E_1$ and $E_2$, heart function can be improved by pacing and/or mapping to delivering such pulses to a cardiac site. Such pacing/mapping can also be used to determine a pacing (voltage) threshold, beyond the capture threshold, to improve the heart's function. Such an approach can also be used to provide bi-ventricular pacing from a lead in the right ventricle for such improved heart function. The term "implantable pulse generator" is intended to include pacemakers, implantable converter defibrillators (ICD) and cardiac resynchronization therapies (CRT), all known in the art. As discussed herein, the pulsing waveforms generated by such an IPG are designed such that a tip and ring control module within the IPG generates pulse waveforms of opposing polarities for an electrical pacing signal that includes two pulses occurring sufficiently proximate one another for the myocardium capture near the target region; these pulse waveforms can include Xstim pacing signals.

In FIG. 1, a patient's heart H is schematically shown in cross-section. The heart H includes the upper chambers of the right atrium RA and left atrium LA. The lower chambers are the right ventricle RV and left ventricle LV. Of the various venous vessels opening into the right atrium RA, only the superior vena cava SVC is shown. Also, of the various heart valves, only the mitral valve MV (separating the left atrium LA from the left ventricle LV) and the tricuspid valve TV (separating the right atrium RA from the right ventricle RV) are shown. The septum S separates the right and left ventricles RV, LV and the free wall FW of the left ventricle LV is separately labeled. The surface of the heart wall tissue opposing the chambers is the endocardium and is labeled as EN. The exterior surface of the heart is the epicardium and is labeled EP. Not shown are coronary vessels of the heart or the pericardium surrounding the heart H.

As a specific embodiment, FIG. 1 includes an electrode lead in an embodiment where signals are delivered via a dual (inner and outer) sheath catheter and shown as having a lead body $LB_1$ and exposed electrodes $E_1$ and $E_2$. The first electrode $E_1$ is positioned near the distal tip of the lead body $LB_1$. The second electrode $E_2$ is positioned more proximally on the lead body $LB_1$. At the distal end, an attachment mechanism AM (such as a passive fixation design with tines or an active fixation design with a metallic helix) is shown for securing the first electrode $E_1$ to the musculature of the heart H. The spacing of electrodes $E_1$, $E_2$ could be greater or smaller than that of convention pacing electrodes permitting positioning of the first electrode $E_1$ at the apex of the right ventricle RV and the second electrode $E_2$ in the right ventricle RV near the tricuspid valve TV. It is noted that conventional leads with convention spacing have been used with the first or distal electrode attached to the septum (e.g., by a helix attachment HA as shown in FIG. 7A).

According to various embodiments of the present invention, the position of electrodes $E_1$ and $E_2$ is determined by monitoring and analyzing the effectiveness of the pacing. In one example, an electrocardiogram (ECG) is used to monitor the cardiac waveform. The electrode position may be incrementally adjusted and the feedback from the ECG can be compared for each position. In a specific example, the QRS width is used in such a comparison. Another parameter that may be considered includes the angle of the vectocardiogram. For example, the analysis of the vectocardiogram may be viewed in terms of normalization of the vectocardiogram. For further information on vectocardiographic measurements and normalization, reference can be made to, Sotobata I, Okumura M, Ishikawa H, Yamauchi K.; *Population distribution of Frank-vectorcardiographic measurements of healthy Japanese men*. Jpn Circ J. 1975 August; 39(8):895-903, which is fully incorporated herein by reference. In another example, the efficiency of the contraction can be ascertained by monitoring the synchrony of the contraction using two-dimensional echocardiography. In still another example, the efficiency of the contraction can be ascertained by monitoring the coronary sinus electrogram to determine the time delay that the activation wave front has between the pacing stimuli (or the resulting QRS complex) until a left ventricular activation is detected at the coronary sinus or any other (late activation) structure of the left ventricle. This may be accomplished using an electrophysiology-style catheter or any other catheter with one or more electrodes close to its tip. In one instance, the goal is to minimize the time delay.

In one embodiment, the lead body $LB_1$ is flexible and includes a bio-compatible, electrically insulating coating surrounding first and second conductors $C_1$, $C_2$ separately connected to the first and second electrodes $E_1$, $E_2$. In the various Figures, the lead bodies are broken at a line at the SVC to reveal the internal conductors $C_1$, $C_2$ extending to an implantable pulse generator IPG. In fact, the conductors $C_1$, $C_2$ are contained within the material of the lead body $LB_1$ along their length.

The proximal end of the lead body terminates at a pin connector (not shown) as is customary. The pin connector has exposed electrical contacts uniquely connected to each of the conductors $C_1$, $C_2$. The pin connector may be connected to the pulse generator IPG so as to be releasable and with the exposed contacts making electrical connection with unique contacts of the circuitry of the pulse generator IPG.

It will be appreciated that the prior art contains numerous examples of cardiac leads for placement in a chamber of the heart where the leads have, as described above, two or more electrodes spaced along a length of the lead, attachment mechanisms such as passive or active fixation and conductors and connector pins as described. The current invention is not limited to pacing leads only, but rather is equally deployable with prior art ICD leads where it is customary to contain at least two electrodes in the RV. Such leads are selected of biocompatible material and treated (such as sterilized) for chronic placement in the patient.

The implantable pulse generator IPG is a small metallic container sealed for implantation in the patient and protecting internal circuitry. Commonly, such pulse generators are placed subcutaneously (e.g., in a dissected space between the skin and muscle layers of the patient). For cardiac pacing, such pulse generators are positioned in the upper chest on either the left or right front side of the patient near a shoulder. However, placement need not be so restricted and such pulse generators could be placed in any convenient location selected by the physician.

Pulse generators contain internal circuitry for creating electrical impulses which are applied to the electrodes after the lead is connected to the pulse generator. Also, such circuitry may include sensing and amplification circuitry so that electrodes $E_1$, $E_2$ may be used as sensing electrodes to sense and have the IPG report on the patient's electrophysiology.

The lead may be introduced to the vasculature through a small incision and advanced through the vasculature and into the right atrium RA and right ventricle to the position shown in FIG. 1. Such advancement typically occurs in an electrophysiology lab where the advancement of the lead can be visualized through fluoroscopy.

The pulse generator contains a battery as a power supply. With subcutaneous placement, replacement of a battery is possible. However, improvements in battery designs have resulted in longer-lasting batteries with the benefit of reducing the frequency of battery replacement. Alternatively, such batteries may be rechargeable in situ.

The pulse generator circuitry controls the parameters of the signals coupled to the electrodes $E_1$, $E_2$. These parameters can include pulse amplitude, timing, and pulse duration by way of example. The internal circuitry further includes circuit logic permitting reprogramming of the pulse generator to permit a physician to alter pacing parameters to suit the need of a particular patient. Such programming can be affected by inputting programming instructions to the pulse generator via wireless transmission from an external programmer. Pulse generators commonly include an exposed contact on the exterior of the generator housing. Such pulse generators may also be partially covered with an insulator, such as silicone, with a window formed in the insulator to expose a portion of the metallic housing which functions as a return electrode in so-called unipolar pacing. In bipolar pacing, the window is not necessary. Most commonly, the electrode is connected by the circuitry of the housing to an electrical ground.

While an implantable pulse generator is described in one embodiment, the pulse generator may be external and coupled to the electrodes by percutaneous leads or wireless transmission. For example, a control of an implanted electrode is known for phrenic nerve stimulation and is described more fully in a product brochure, "ATROSTIM PHRENIC NERVE STIMULATOR", AtroTech Oy, P.O. Box 28, FIN-33721, Tampere, Finland (June 2004). The Atrostim device sends signals from an external controller to an implanted antenna.

External pacing devices are typically used for providing temporary pacing therapy. Aspects of the current invention are also believed to have advantages for this application as critically-ill patients requiring emergency, temporary pacing may also suffer further from asynchronous cardiac contraction associated with conventional RV pacing. If desired, an external unit can be used to test a patient's suitability for the treatment. Patients who benefit from the therapy can then receive an implantable pulse generator for longer-term use.

FIG. 2 illustrates a lead body $LB_2$ in the right ventricle RV with the electrodes $E_1$, $E_2$ directly placed on the septal wall S and held in place against the septal wall through any suitable means. For example, FIG. 2A illustrates one embodiment for attachment of an electrode against the septal wall. The lead body $LB_2$ is shown as having an internal lumen LU with a port PO near an electrode (e.g., electrode $E_2$). Any suitable attachment mechanism (such as a pigtail guide wire or an injected bio-adhesive) can be passed through the lumen LU and port PO to fix the electrode $E_2$ in abutment against the septal wall S. Further, a guide catheter could also be used in moving the implantable lead to assist in the mapping of the optimal location of the septum.

FIG. 3 illustrates the electrodes $E_1$, $E_2$ against the septal wall S but without requiring an attachment mechanism. Instead, an intermediate region (IR) of the lead body $LB_3$ is formed of shaped memory material (such as nitinol) to assume an S-shaped configuration and urge the electrodes $E_1$, $E_2$ against the septal wall S.

Figure 4:
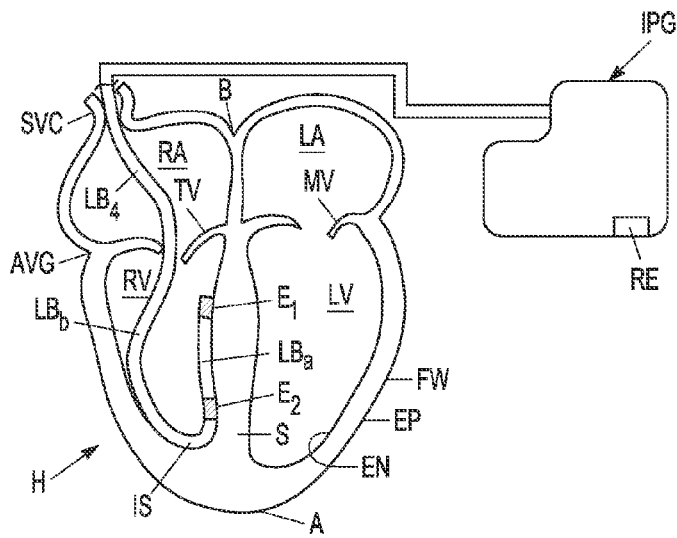
FIG. 4 is the view of FIG. 1 showing a further embodiment of an electrode lead for urging electrodes against a septal wall.

In FIG. 4, the lead body $LB_4$ has two components $LB_a$, $LB_b$ joined by an intermediate section IS which may be formed of any elastomeric material (such as a shaped memory material). The intermediate section (IS) is biased to urge the two components $LB_a$, $LB_b$ into collinear alignment. With the intermediate section IS placed against the apex of the right ventricle (RV), the bias of the intermediate section IS urges the electrodes $E_1$, $E_2$ against the septal wall S.

Figure 5:
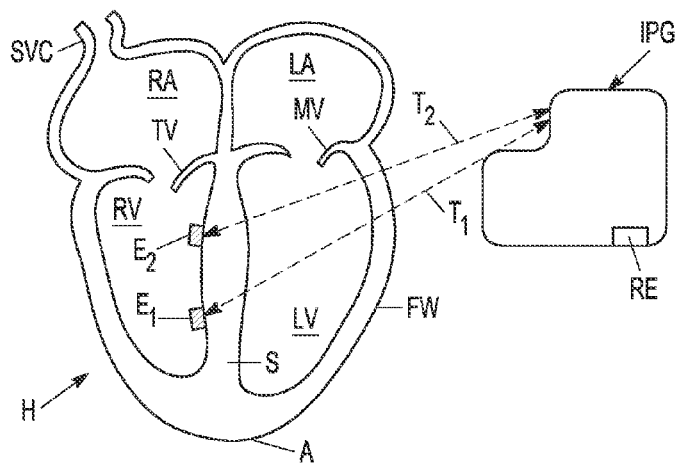
FIG. 5 is the view of FIG. 1 showing electrodes on a septal wall and energized by wireless transmission.
Figure 6:
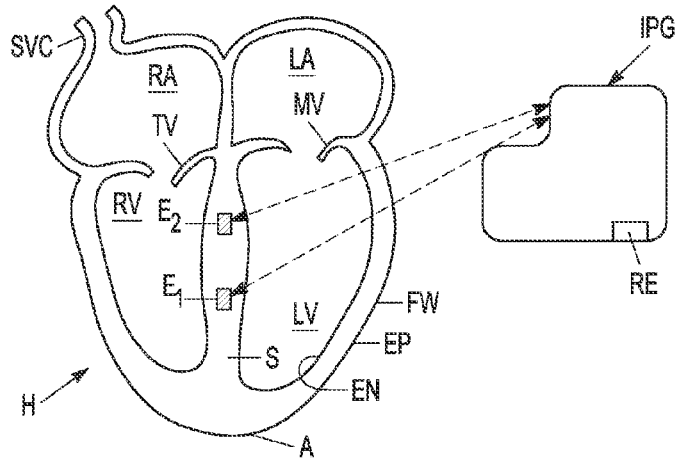
FIG. 6 is the view of FIG. 5 showing electrodes embedded within the septal wall.

FIG. 5 illustrates the electrodes $E_1$, $E_2$ individually placed on the septal wall S and not retained on a lead body. In such an embodiment, the electrodes $E_1$, $E_2$ may be energized in a pacing waveform by wireless transmission signals $T_1$, $T_2$ from the implantable pulse generator (IPG). Wireless transmission from a controller to an electrode is shown in U.S. Pat. No. 6,907,285 to Denker, et al., dated Jun. 14, 2004. Alternatively, the electrodes $E_1$, $E_2$ may be directly imbedded as microstimulators into the tissue of the septal wall S as illustrated in FIG. 6. Microstimulators for implantation into human tissue are shown in U.S. patent application Publ. No. 2004/0153127 published Aug. 5, 2004.

In a context similar to that discussed above, FIGS. 1-20 illustrate aspects of the present invention similar to that discussed above in connection with FIG. 1 where certain of these figures show common characteristics. FIGS. 1, 7B and 8 illustrate example leads and the associated electrical fields with both electrodes residing within the right ventricle with the distal electrode secured to the apex of the right ventricle, with FIG. 8 showing the ventricles RV, LV and a portion of the lead body $LB_1$. While such bipolar leads are acceptable for use with the present invention, a wider spacing between electrodes $E_1$, $E_2$ can increase the field but can sacrifice some sensing capability. This trade-off can be mitigated by use of a three-electrode lead in the right ventricle RV. Such a lead would have a tip electrode and two ring electrodes, one located near the tip in the RV apex and one in the high part of the atrium, near the tricuspid valve. The sensing is performed between the tip and closer electrode. This will provide good so-called "near field" sensing and avoid so-called "far field" sensing of the atrium or skeletal muscles activity. The pacing could be between the ring electrodes to the return electrode located distally to the heart (as will be described). One could also combine the tip and nearest ring as one electrode to the return electrode and the other ring electrode to the return electrode at the opposite polarity. In a particular embodiment, a ring with a width of 4 mm is separated by a distance of 4 mm from a tip with a width of 4 mm.

Figure 18:
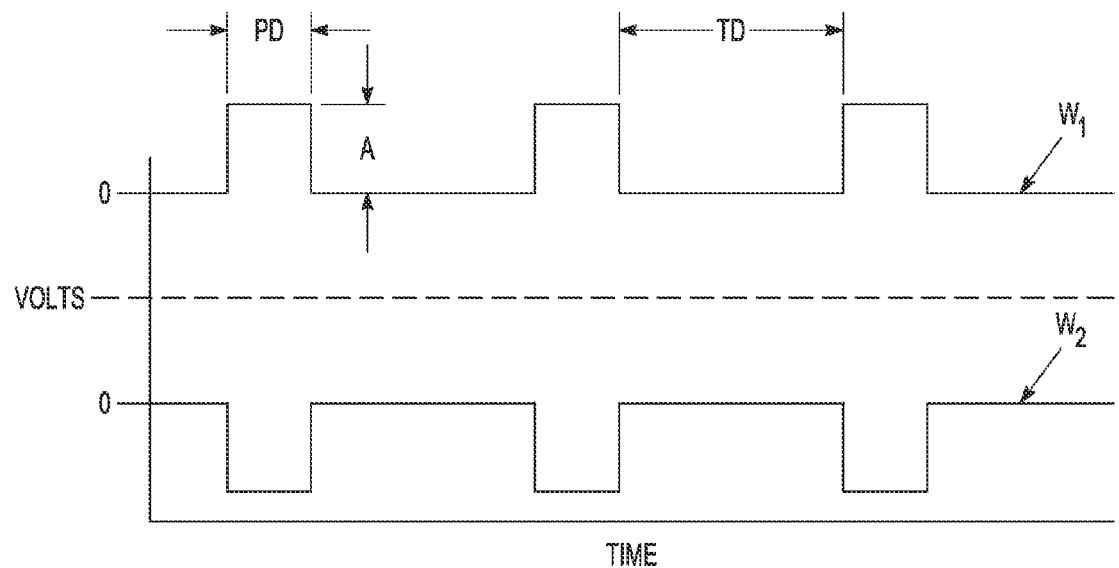
FIG. 18 is a graphical representation of pulsed waveforms to be applied by first and second electrodes of the various embodiments.

Another characteristic is the pulse generator IPG which is common to FIGS. 1-7b. The pulse generator IPG generates a first and a second pulsed waveform $W_1$, $W_2$ applied, respectively, to the first and second electrodes $E_1$, $E_2$. FIG. 18 shows such waveforms $W_1$, $W_2$ of depicting signals generated by this illustrated IPG. By way of example, and not intended to be limiting, the pulse duration (PD) is between about 0.1 to 2.0 milliseconds, the amplitude A may be 0.1 Volts to 10 or 20 Volts and the time delay TD between pulses is a targeting heart rate (e.g., 50 to 200 beats per minute).

The arrangements shown in FIGS. 1-18B show examples of electrode placements (e.g., electrode $E_1$) at various positions along or near the septal wall. In FIG. 7A, for example, the first electrode $E_1$ is attached to the mid- or upper-septum.

The reference electrode RE, used in some but not all such embodiments of the present invention, is on the housing of the IPG and positioned subcutaneously near the right or left shoulder. The re-direction of the field may also be useful in decreasing defibrillation thresholds for arrangement similar to that shown in FIG. 7B. In FIG. 7B large segmented (for flexibility) electrodes $E_2$, $E_3$ are shown in the superior vena cava SVC near the atrium RA and in the right ventricle to serve as shocking electrodes to defibrillate a patient.

Figure 8:
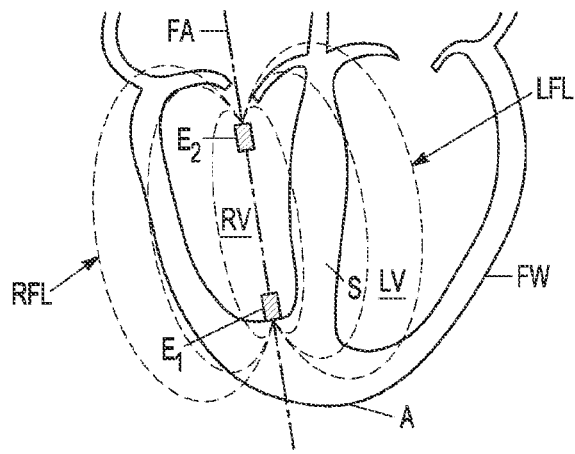
FIG. 8 is a view, taken in cross-section, of right and left ventricles of a heart showing the electrodes of FIG. 1 (without showing the lead body) energized to create electromagnetic fields.
Figure 9:
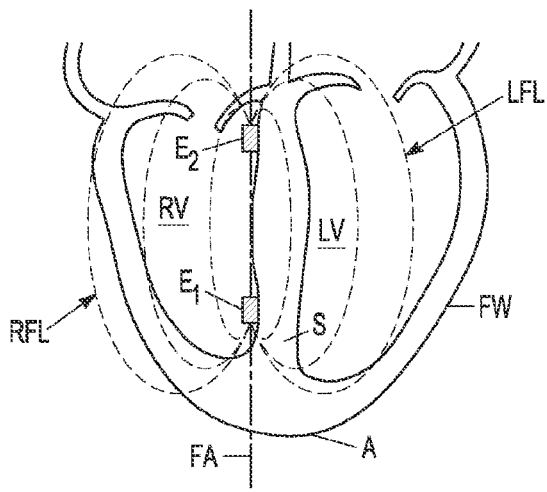
FIG. 9 is the view of FIG. 8 showing the field shifted toward the left ventricle in response to repositioning of leads.

Another characteristic relating to the above-discussed aspects for improved heart function concerns placement of the electrodes to effectively stimulate the septal wall. As an illustrated example of such placement, FIG. 9 shows field lines useful for such stimulation and resulting from movement of the electrodes $E_1$, $E_2$ from the interior of the right ventricle RV (FIGS. 1 and 8) to the septal wall S. Such movement shifts the field lines toward both the septal wall S and the free wall FW of the left ventricle LV.

Certain of the embodiments that use a reference electrode RE in combination with the electrodes $E_1$, $E_2$ in the right ventricle, provide effective pacing of the left and right ventricles LV. Although the physics and physiology of the mechanism of action are not fully understood, it may be that the reference electrode RE distorts the electromagnetic field otherwise created between the right ventricle electrodes $E_1$, $E_2$ to urge an intensity of the electromagnetic field deeper into the septal wall S of the left ventricle LV. This may be due to creation of a third high current density spot (or spots) away from the two electrodes in the wall and towards the reference electrode at the point where the current flows between the electrode $E_1$ and the reference electrode RE and between the electrode $E_2$ and the reference electrode RE while coinciding in space and time. This is illustrated, for example, in FIG. 10. Assuming such a phenomenon occurs, it may facilitate the activation of the surviving conduction fibers in the Left Bundle Branch and Right Bundle Branch of His and Purkinje fibers and create a more rapid and uniform activation of the left and right ventricles that follows a similar pattern to the normal activation present in patients without conduction defects.

The reference electrode may be physically attached to the housing of the implantable pulse generator IPG (and thereby having a neutral charge). Such an electrode RE is shown in FIGS. 1-7B. It will be appreciated that the reference electrode RE can be connected to the implantable pulse generator IPG by a conductor. The reference electrode could be another common electrode that exists in the conventional pacing or ICD system, such as an electrode in the atrium or a defibrillation coil electrode situated in the SVC, RA or RV.

Figure 10:
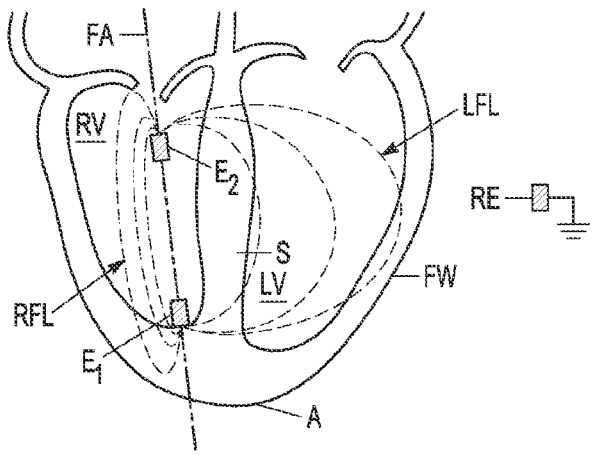
FIG. 10 is the view of FIG. 8 showing the field distorted toward a free wall of the left ventricle by influence of an external reference electrode.
Figure 11:
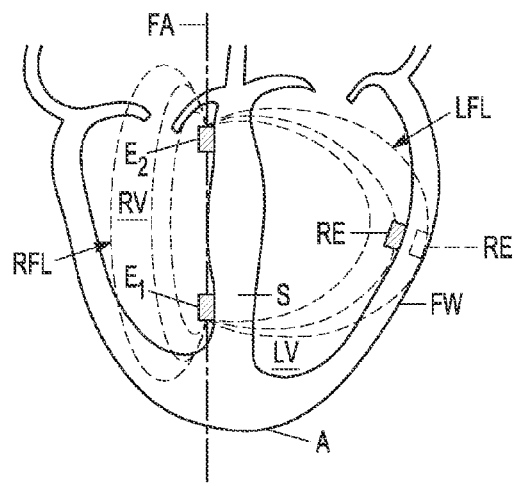
FIG. 11 is the view of FIG. 9 with a reference electrode placed within the left ventricle.
Figure 12:
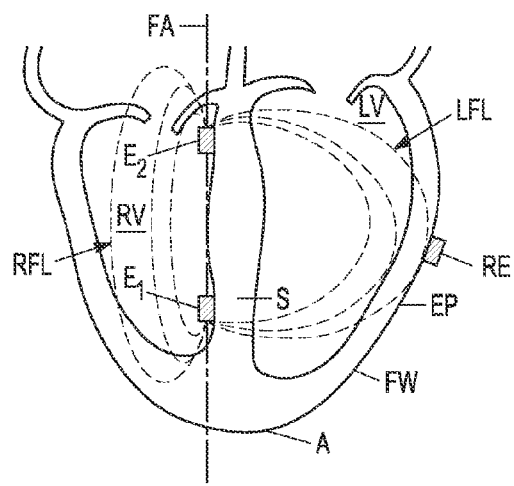
FIG. 12 is the view of FIG. 14 with an external electrode placed on the epicardial surface of the heart.

As shown in FIG. 10, the consequence of the reference electrode RE may have a deforming effect on the electromagnetic field generated between the first and second electrodes $E_1$, $E_2$. This is illustrated in FIG. 10 by distorting the left field lines LFL toward the septal wall S and free wall FW of the left ventricle LV. Also, the right field lined (RFL) are compressed toward the axis FA to alter the field from the symmetric presentation of FIGS. 8 and 9 to the asymmetric presentation of FIG. 10 with the field biased toward the septal wall S and the free wall FW of the left ventricle LV.

It has also been found that within energy levels associated with available implantable pulse generators (in some instances up to 10 or 20 volts), effective activation of the left and right ventricles LV can be achieved with appropriate placement of the pacing leads.

Chronic pacing with an anodal electrode is believed to create an exit (anodal) block, meaning that the capture thresholds of the cardiac tissue may go beyond the voltage range of the pulse generator. When this happens the beneficial effect of the stimulation is lost. Since capture is often lost, the patient's life may be placed at risk by such an event.

According to one embodiment of the present invention, the polarity of the charged pulses seen at electrodes $E_1$ and $E_2$ may be alternated. This can be particularly useful for avoidance of anodal blocking (gradual rising of the threshold voltage necessary to capture and re-synchronize the myocardium). Such polarity swapping may be implemented using a suitable periodicity. In a particular example, the polarity of the electrodes is switched after several hours of operation. In another example, this polarity is alternated beat by beat, so that the net charge delivered to the tissue over two beats would be zero. The frequency of alternation could be varied in a very wide range and still accomplish the goal of balancing the charge delivered, to allow for the net charge delivered on average to be near zero. This can be useful for avoiding the issue of anodal block and minimizing the risk of electrode dissolution and/or corrosion.

It has been discovered that in some instances proper placement of the lead along the septum produces unexpectedly small QRS widths. Moreover, proper placement may also result in lower voltage thresholds. The optimal lead location can be determined with the assistance of the surface ECG parameters (e.g., QRS width and/or activation vectors).

Figure 13:
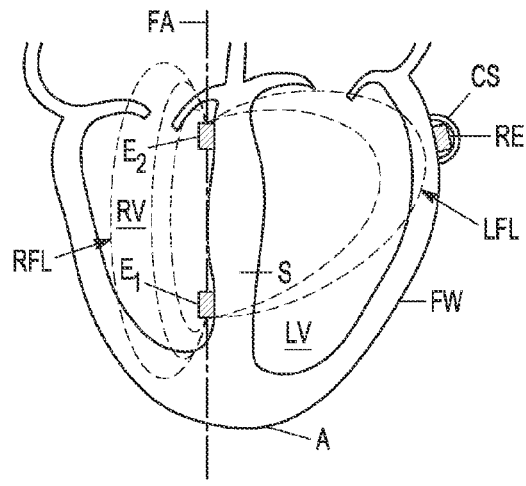
FIG. 13 is a view with an external electrode placed within a coronary sinus.

The positioning of the reference electrode RE may be directly on the housing of the implantable pulse generator IPG or may be separate from the internal pulse generator as previously mentioned. In one instance, the reference electrode RE can be placed in the left ventricle (FIG. 11) (or in the tissue of the free wall FW as shown in phantom lines in FIG. 11), on the epicardial surface EP (FIG. 12) or in the coronary sinus CS (FIG. 13).

Positioning the reference electrode RE relative to the heart can affect the distortion of the field in the area of the left ventricle free wall FW subject to pacing. Particularly for a subcutaneously placed reference electrode (which is preferred to minimize the invasive nature of the procedure), the electrical conduction path from the right ventricle RV to the reference electrode will vary considerably between patients.

Figure 15:
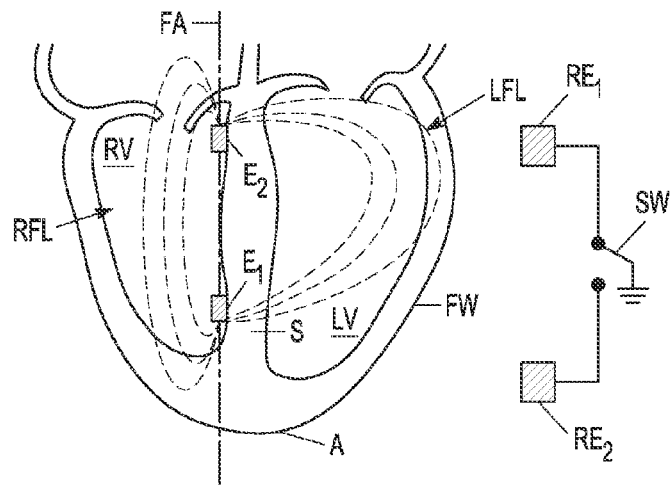
FIG. 15 shows a field distorted towards an upper end of the free wall in response to a reference electrode in a first position.
Figure 16:
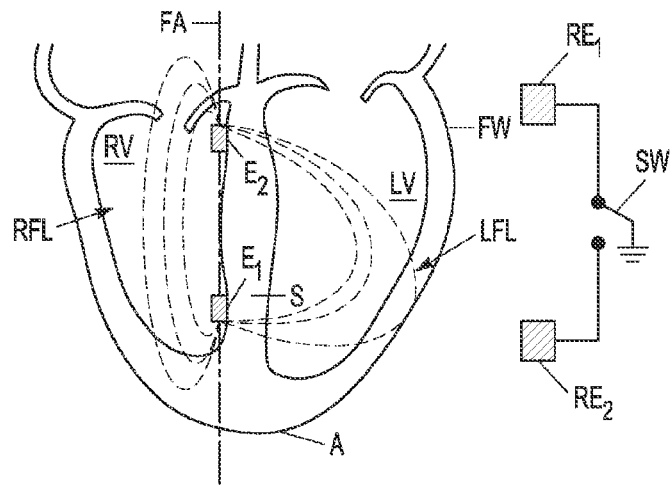
FIG. 16 is the view of FIG. 15 with a reference electrode switched to a second position.

Also, the direction of field distortion may alter the region of the left ventricle LV subject to pacing. For example, FIG. 15 illustrates the reference electrode $RE_1$ placed high relative to the heart, resulting in a distortion of the field toward the upper end of the left ventricle septum and free wall FW. FIG. 16 illustrates placement of a reference electrode $RE_2$ lower relative to the heart and to deflect the intensity of the field toward the lower end of the left ventricle septum and free wall FW.

While the reference electrode could be a single electrode, multiple electrodes could be provided for subcutaneous placement and each connected by a switch circuitry SW of the implantable pulse generator as illustrated in FIGS. 15 and 16. The patient's response can be noted with each of the several reference electrodes $RE_1$, $RE_2$ separately connected to the ground or housing of the implantable pulse generator. The patient can then be treated with the electrode showing the most effectiveness for the particular patient. Further, over time, a patient's response may change and the implantable pulse generator can be reprogrammed to select any one of the other reference electrodes as the switched electrode.

Figure 7:
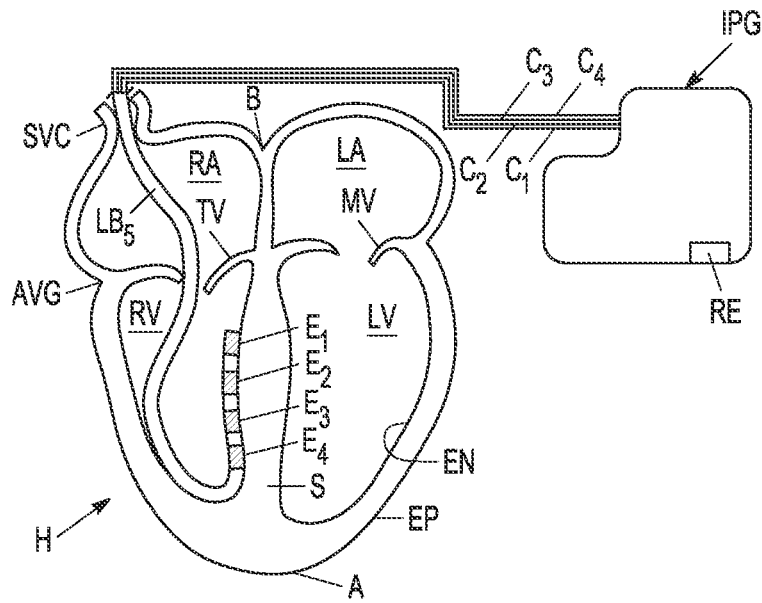
FIG. 7 is the view of FIG. 4 showing the lead of FIG. 4 with multiple electrodes urged against the septal wall.
Figure 7A:
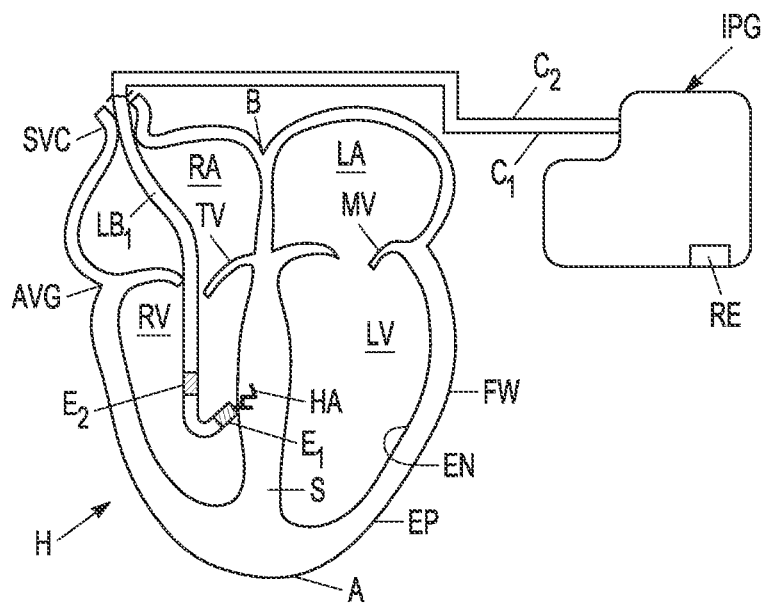
FIG. 7A is the view of FIG. 1 showing a conventional active fixation lead with a helix for attachment of the tip electrode to a septal wall.
Figure 7B:
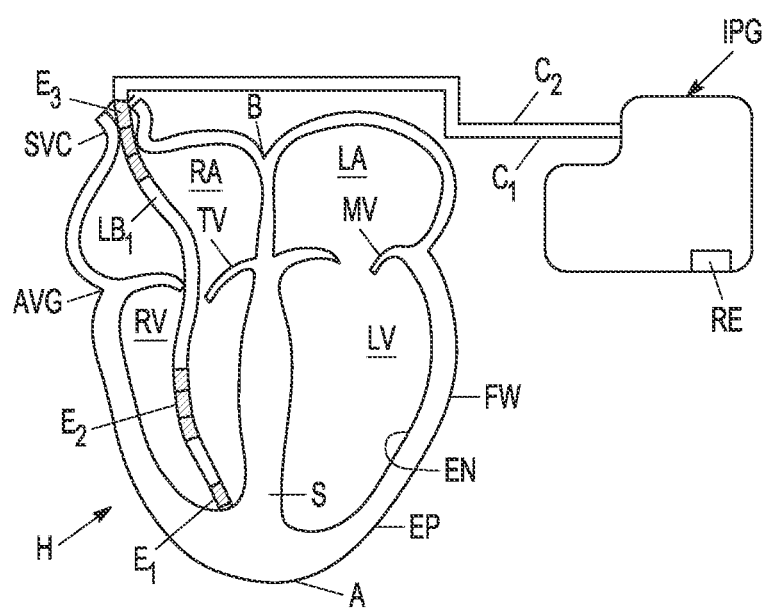
FIG. 7B is the view of FIG. 1 showing a shocking electrode.

In addition, the catheter $LB_5$ within the right ventricle can have multiple electrodes along its length (as shown in FIG. 7). Individual pairs of these electrodes $E_1$-$E_4$ can be switched on or off over time so that the appropriate pair of electrodes within the right ventricle is selected for optimized left ventricular pacing.

Figure 14:
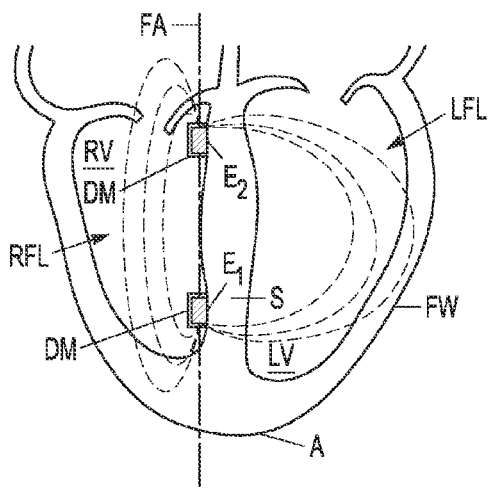
FIG. 14 is the view of FIG. 9 with fields distorted to be biased toward the left ventricle by the addition of dielectric material on a side of the electrodes of FIG. 9.

FIG. 14 illustrates how the field can also be distorted by dielectric material DM placed on a side of the electrodes $E_1$, $E_2$ opposite the septal wall S. The dielectric material DM result in a distortion of the electrical field biasing the left field lines LFL toward the septal wall S and the free wall FW. Of course, this configuration will work even better with a reference electrode which will enhance the benefit.

While positioning of the electrodes $E_1$, $E_2$ within the volume of the right ventricle RV is effective in combination with a reference electrode RE (FIG. 10), movement of the electrodes $E_1$, $E_2$ directly against the septal wall S may further enhance the therapeutic benefit of the present invention for reasons described above. Various techniques for movement of the electrodes $E_1$, $E_2$ against the septal wall S are disclosed.

Figure 17:
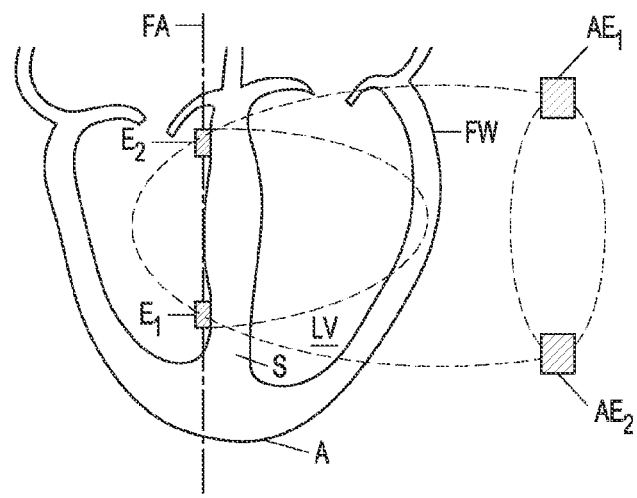
FIG. 17 is the view of FIG. 15 with a reference electrode replaced by two polarized electrodes.

In various embodiments, the reference electrode is grounded to the housing of the implantable pulse generator. FIG. 17 illustrates an alternative embodiment where the reference electrode includes two active electrodes $AE_1$, $AE_2$ external to the heart. The active electrodes $AE_1$, $AE_2$ are paced with pulsed waveforms which are polar opposites of the waveforms on electrodes $E_1$, $E_2$. This creates dual unipolar field in addition to the left field lines LFL previously described.

Figure 19:
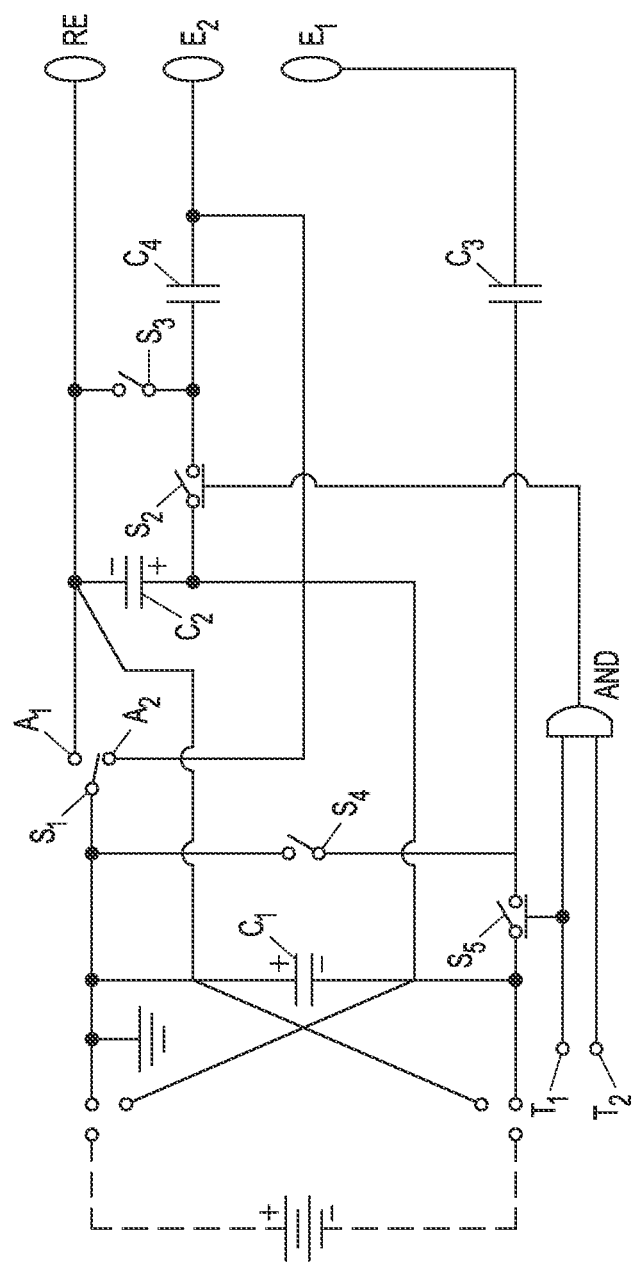
FIG. 19 is an electrical schematic for a portion of a pacing output desired in a pulse generator with programmable pacing configurations.

In the Figure, the amplitude of the waveforms from FIG. 18 (or other waveforms as described) is shown in phantom lines as the battery voltage applied to the four poles on the left of FIG. 19 to charge the two pacing capacitors $C_1$ and $C_2$. Details of the charging circuitry as well as other controlling circuitry for pacing and sensing are omitted for ease of illustration. In one instance only capacitor $C_1$ is charged for the pacing output, whereas $C_2$ is not charged. Capacitor $C_3$ and $C_4$ are optionally implemented for coupling the pacing output to the patient. For ease of illustration and explanation, the output waveform from FIG. 18 with the same amplitude and simultaneous timing is assumed for the design schematic in FIG. 19. A switch $S_1$ permits selection between unipolar pacing and pacing Xstim or similar pacing (by contact with switch pole $A_1$) or bi-polar pacing (by contact with switch pole $A_2$). Selection between bi-polar pacing or Xstim pacing is made by applying a digital signal with the timing information as shown in FIG. 18 to either $T_1$ or $T_1$ and $T_2$, namely to either toggle the switch $S_5$ or $S_2$ and $S_5$ simultaneously. An AND gate is used to allow the close of the switch $S_2$ only for pacing according to Xstim. Switches $S_3$ and $S_4$ permit re-neutralization of the pacing charges at the patient-electrode interface.

As is customary with implantable pulse generators, the device may be programmable to achieve either conventional bipolar or unipolar stimulation or to achieve the Xstim stimulation through an external programmer or controlled automatically by the device. The selection can be based on user preference or be driven by physiological factors such as widths of the patient's QRS complex or the conduction interval between the stimulus to a far away region in the heart. In addition, switching between the Xstim pacing and other pacing can also be determined by the percentage of pacing with a preference for a higher percentage with the pacing of the present invention. Further, the switching from a first type of pacing to the Xstim pacing can be used when there exists an exit block or the pacing electrode is located in infracted myocardium when first type pacing does not capture (effect the depolarization of) the myocardium at the high output level. The automatic determination can be effected through the deployment of any automatic capture detection technology including, but not limited to, electrical sensing of the heart. Additionally, wireless network-enabled switching function for therapy optimization can also be implemented with the present invention. In such cases, certain patient physiologic data are gathered by the implantable device and sent to a remote server/monitor through a wireless communication network.

In connection with other embodiments and related to the waveforms shown in FIG. 18, the stimulus voltage is consistent with discharge of an RC circuit as shown by FIG. 23A. This may be accomplished by connecting the electrode(s) to the anode (and/or cathode) of a charged capacitor.

According to another embodiment of the present invention, the stimulus voltage is consistent with the discharge of two sets of two capacitors in succession, as shown by FIG. 23B. This may be accomplished by connecting the electrode(s) to the anode (and/or cathode) of a first charged capacitor and then to a second charged capacitor. This embodiment may be useful for reducing the voltage swing of the pulse, thereby altering the delivery of energy during the active stimulation period and potentially minimizing the voltage required to achieve the desired effect. In a particular instance, a first set of capacitors could be connected to electrode $E_1$ and a second set could be connected to electrode $E_2$. The voltages provided to the electrodes could be of opposite polarity as in the standard Xstim waveform or could be alternated as described above to make the net charge delivered to the electrodes equal to zero.

Figure 23D:
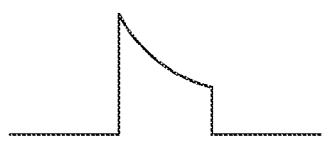
Figure 23D:
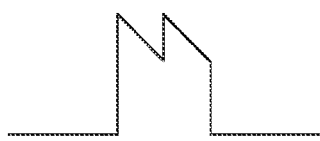
Figure 23D:
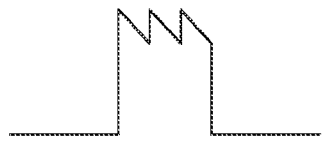
Figure 23D:
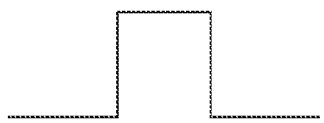

Other embodiments may allow for the use of two sets of three or more capacitors as shown by FIG. 23C. Moreover, various voltage-regulation techniques may be used to provide a constant voltage, or square waveform, as shown by FIG. 23D. This may be useful to provide a more constant delivery of voltage during the active stimulation period. In some instances, such waveforms may allow the reduction of voltage thresholds required to achieve the desired effect. According to one embodiment of the invention, one of these groups of three or more capacitors could be connected to electrode $E_1$ and the other group of three capacitors could be connected to electrode $E_2$. The two groups may be charged to opposite polarities, as in the standard Xstim waveform. Alternatively, the groups may alternate between electrodes $E_1$ and $E_2$, as described above, resulting in the net charge delivered to the stimulus point by the electrodes equal to zero.

Furthermore, in a less expensive device, using a single capacitor element (or multiple capacitors arranged in parallel), a single set of two capacitors independently addressable or set of three or more capacitors each independently addressable, the same effect could be achieved by using an anodal pulse delivered through the capacitive discharge of one, two or three or more capacitors to one of the electrodes with a larger amplitude voltage. This anodal pulse will be alternatively connected to one of the stimulating electrodes in one beat and to the next electrode on the next beat. In still another device the alternating frequency could be lower. For example, the anodal capacitive discharge could be alternatively connected to electrode $E_1$ and then to $E_2$ every 2 to 10,000 beats. If the alternating charges are equally distributed, the net charge delivered may be kept very close to zero. During the implantation of such a device the physician may place an intraventricular pacing lead in a preferred location (locus) that maintains the effect (using one of the previously-described methods, making each electrode alternatively the anode) when either of the electrodes is the anodal electrode.

The pulse width of the various embodiments may be varied according to the desired treatment and/or in accordance with the response of the particular patient. Example pulse widths may range from 0.05 ms to 5.0 ms.

According to certain example embodiments of the present invention, resynchronization is achieved by presenting a pulsing signal (waveform) to a sweet spot (e.g., locus in the septal part of the RV endocardium) and, every so often, modulating the signal such as by changing its polarity. In such embodiments where both an anode and cathode are used to present the pulsing signal, one manner of modulating the signal is by reversing the polarities of the signal relative to the anode and cathode. Where the pulsing signal is presented by an electrode and a reference voltage (e.g., a node at the can and/or at the body under treatment), the signal can be modulated in a similar manner by adding and/or skipping pulses.

As discussed infra, the power consumption of the pacing device can be an important consideration. While not bounded by theory, it is believed that different pacing profiles can be particularly advantageous to controlling pacing power. For example, during times that the pulses applied to each electrode overlap, the effective voltage seen between the electrodes is believed to be equal to that sum of their amplitudes.

Figure 22:
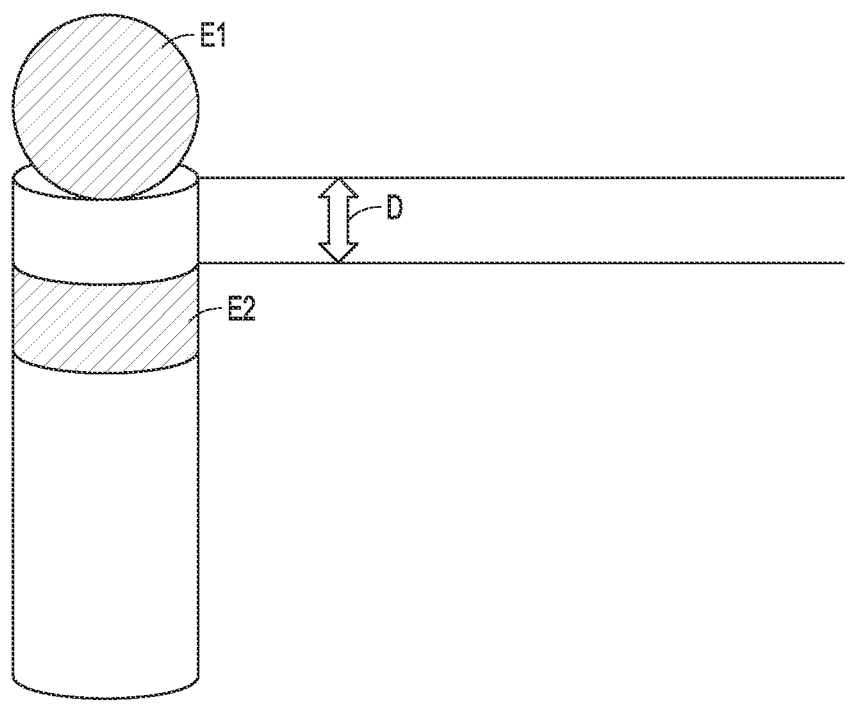
FIG. 22 is a view showing the spacing of two electrodes.

In another embodiment, the pulses shown by the figures are applied to the ring and tip electrodes, such as those illustrated in FIG. 22. The polarity of the voltages, as relative to each other and/or a reference voltage, may be alternated periodically (e.g., beat by beat or every N pulses). As discussed above, such alternating may be particularly useful for mitigating anodal blocking Moreover, alternating of pulses may also mitigate corrosion of the electrodes.

Referring back to FIG. 18, such pulses are shown as square waveforms but, in practice, can be any of various geometries. With reference to FIG. 18 and the earlier figures, the first electrode $E_1$ has positively charged pulses only. The second electrode $E_2$ has negatively charged pulses timed to coincide with the positively charged pulses of the positive electrode $E_1$.

While direct current (DC) pulses are preferred, the electrodes $E_1$, $E_2$ could be energized with alternating current pulses with the signals to the electrodes $E_1$, $E_2$ out of phase such that the positive pulses on the first electrode $E_1$ coincide with negative pulses on the second electrode $E_2$ and negative pulses on the first electrode $E_1$ coincide with positive pulses on the second electrode $E_2$.

With the electrodes $E_1$, $E_2$ charged with opposite pulses, it is Applicants' current understanding that an electrical field is created between the electrodes $E_1$, $E_2$ with a field axis FA (FIG. 8) extending in a line between the electrodes $E_1$, $E_2$. In the absence of distorting influences (such as external magnetic fields, external electrodes or nonhomogonous conductivity due to variances in conductivity of blood, tissue bone, etc.), the field is symmetrical about the field axis FA and is represented by field lines illustrated in the drawings as left field lines LFL to the left of the axis FA (with left being from the patient's perspective) and right field lines RFL. The field lines represent the intensity of the electrical field. The intensity diminishes rapidly as a function of the distance from the field axis FA.

As discussed above in connection with various embodiments including the electrodes $E_1$, $E_2$, in order for the fields generated by the electrodes $E_1$, $E_2$ to have a significant influence on both the septal walls and the free wall FW of the left ventricle LV, a voltage potential across the electrodes is set at a substantially high level. However, such high voltages are not practical in a pacing electrode and are more normally associated with defibrillating treatments. Also, such voltages may cause phrenic nerve and/or diaphragmatic stimulation and may also cause a significant drain on a battery that would require impractical frequency of battery replacement.

Figure 18A:
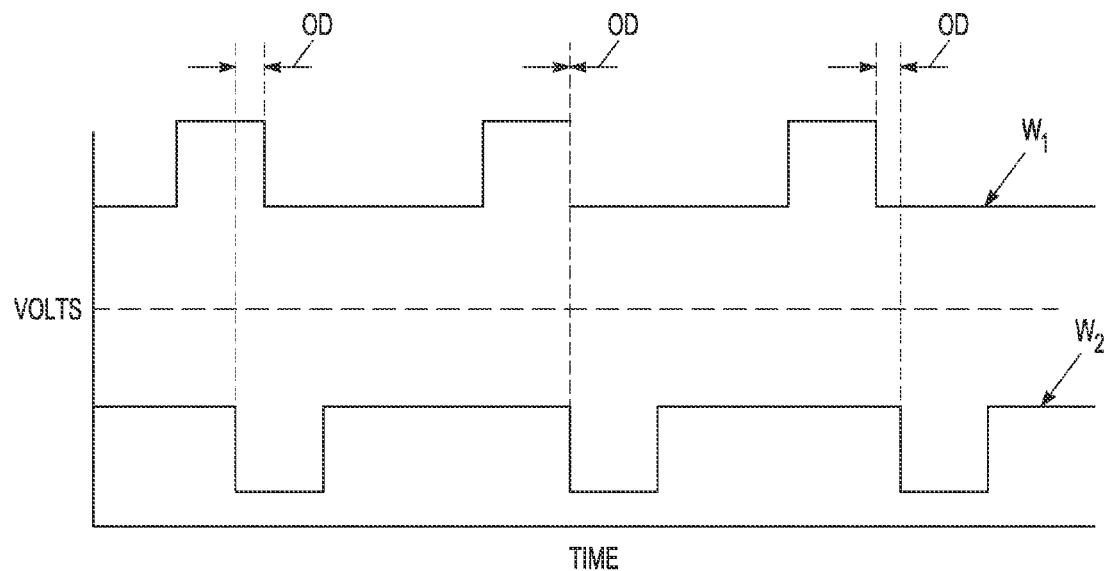
FIG. 18A is a view similar to that of FIG. 18 showing alternative waveforms.
Figure 18B:
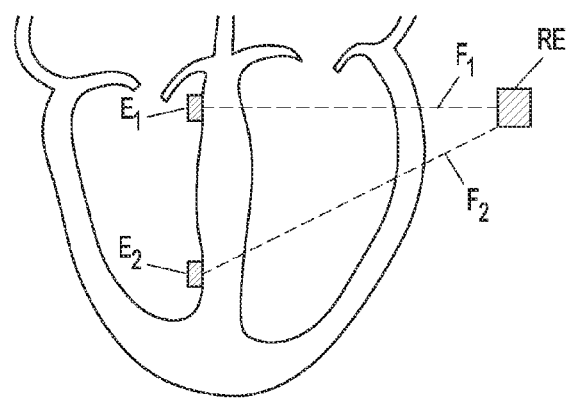
FIG. 18B is a view similar to that of FIG. 18 and showing two electrodes creating two separate fields to a reference electrode.

FIG. 18 illustrates an example waveform with electrodes $E_1$, $E_2$ being simultaneously pulsed with opposite polarity. FIG. 18A illustrates waveforms $W_1'$, $W_2'$ of similar structure to the waveforms of FIG. 18 but out of phase. The first set of pulse illustrated in waveforms $W_1'$, $W_2'$ present a partial overlap duration OD (OD is a positive value). The second set of pulses are further out of phase such that the beginning of one pulse coincides with the end of another pulse (OD=0). The third set of pulses includes pulses that are out of phase such that the leading edge of one pulse occurs after the end of the first pulse of the set (OD has a negative value). With FIG. 18A at least a portion of time includes a monopolar pacing from individual ones of the electrodes $E_1$, $E_2$ to the reference electrode RE. This pacing creates out of phase monopolar fields $F_1$, $F_2$ as illustrated in FIG. 18B. Values of OD can range from the entire pulse length (e.g., around two milliseconds) to a negative value of several milliseconds (e.g., around negative two milliseconds). Although not explicitly shown in FIG. 18A, either of the negative or positive pulses can lead the other pulse, respectively. Also, while the amplitudes of the two waveforms are shown to be equal, they need not be equal in practice nor do they necessary need be implemented as strict square waves. For non-square wave pulses or pulses with relatively slow fall or rise times, the OD can be calculated accordingly. In one example, the OD may be calculated from beginning or end of the rise/fall of each pulse, respectively. In another example, the OD may be calculated from when each pulse reaches a certain voltage level, respectively, or once the pulse has maintained a certain voltage level for a period of time.

FIG. 19 illustrates a representative circuit in schematic format for a portion of a cardiac stimulation pulse generator that is capable of providing pacing output for either the conventional waveforms or Xstim waveforms as herein. The circuit of FIG. 19 could be for an implantable pacemaker or any external stimulation system for diagnostic or therapeutic use.

The stimulation device has three output terminals that are connected to three electrodes $E_1$, $E_2$, RE in the body. Electrodes $E_1$, $E_2$ are positioned in the right ventricle RV with it being preferred that at least one of these electrodes be in direct contact with the septum S.

The reference electrode RE is an indifferent electrode which can be connected electronically to the housing of the implantable pulse generator IPG. The reference electrode RE may be an electrode directly on the implantable pulse generator or any other electrode for placement inside or outside of the heart as described above.

The present invention can also be extended to the defibrillation therapy where high-energy pulses with various waveforms are delivered through electrode systems to treat tachycardia and fibrillation (both atrium and ventricle). The present invention is believed to be able to achieve a lower defibrillation threshold due to better distribution of the electrical field, causing higher voltage gradient at least in certain parts of the heart compared to that by the conventional defibrillation configuration as seen in FIG. 7B. Additionally, the present invention can be used to perform anti-tachy pacing where faster than conventional pacing pulse sequences are used to stop certain tachyarrhythmia. Aspects consistent with present invention are believed to provide wider coverage of the electrical field and the capability of capturing special conduction systems in the heart (both atrium and ventricle).

In a particular embodiment, the electrodes $E_1$ and $E_2$ are positioned proximate to one another as shown in FIG. 22. This can be particularly useful for localizing the region in which the electrical stimulus (using one of the configurations described before) can achieve the desired synchronization or resynchronization effect. For example, the electrodes may have a width of around 4 mm and may be positioned within a distance D of about 5 mm from one another. In another example, the electrodes may be positioned within a distance D of about 2 mm or less.

The selective placement may be modified for a particular dysfunction and/or for a particular patient. For instance, the electrodes may be positioned near the His bundle. Locating the electrodes near the His bundle may advantageously allow for capture of both the right and left ventricle. Moreover, resynchronization of the left (or right) ventricle may be possible even for cases of LBBB (or RBBB).

Figure 20:
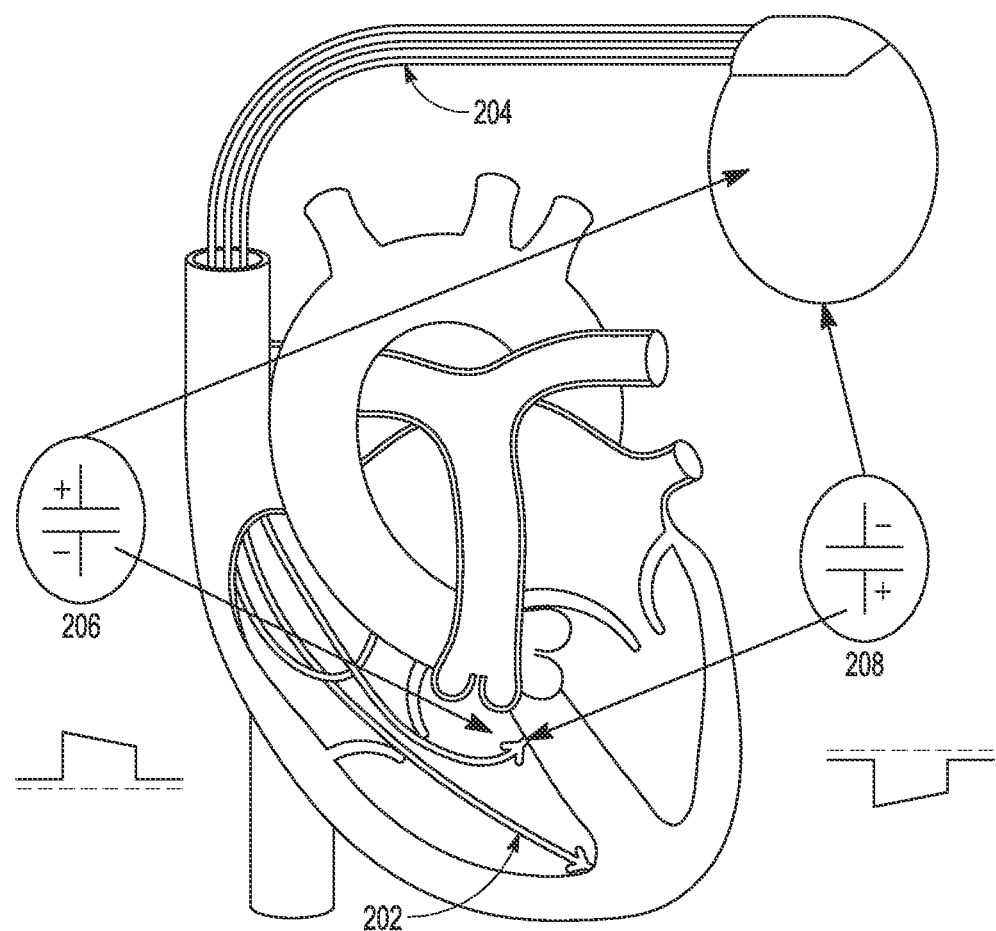
FIG. 20 is cross-sectional view of a patient's heart with circuitry shown for desynchronizing a contraction of the ventricles.

FIG. 20 shows an arrangement for desynchronizing a contraction of the ventricles. The defibrillation lead 202 may have as few as only one or two (coil) electrodes at the right ventricle apex for specific use in defibrillation therapy. This may be particularly useful as the lead need not contain pacing/sensing electrodes, thereby eliminating or lessening the pullback of the RV coil, which has been known to lower the defibrillation threshold. Ventricular pacing lead 204 connects to the ventricular pacing electrodes, depicted as 206 and 208. This ventricular lead is bipolar and with active fixation. This allows for bipolar pacing at a preferred location. For example, the ventricular pacing output employs in phase pulses of opposite in polarity such as used with Xstim pacing as described supra. These pulses of opposite polarity pulses are applied to the tip and the ring electrodes of the ventricular pacing lead 204.

In a specific embodiment (not shown), the implantable pulse generator can also be programmed to function as a cardiac resynchronization device with defibrillation capability. In this configuration, the defibrillation (ICD) lead includes pacing/sensing electrode(s) incorporated into the same lead body. The ventricular pacing lead will be positioned on the left ventricle via the coronary sinus or epicardially. Inside the pulse generator, one pulse will connected to the RV pacing/sensing electrode(s) and the other pulse will be connected to the LV pacing/sensing electrode. In a specific instance, both pulses may be negative in polarity.

Figure 21:
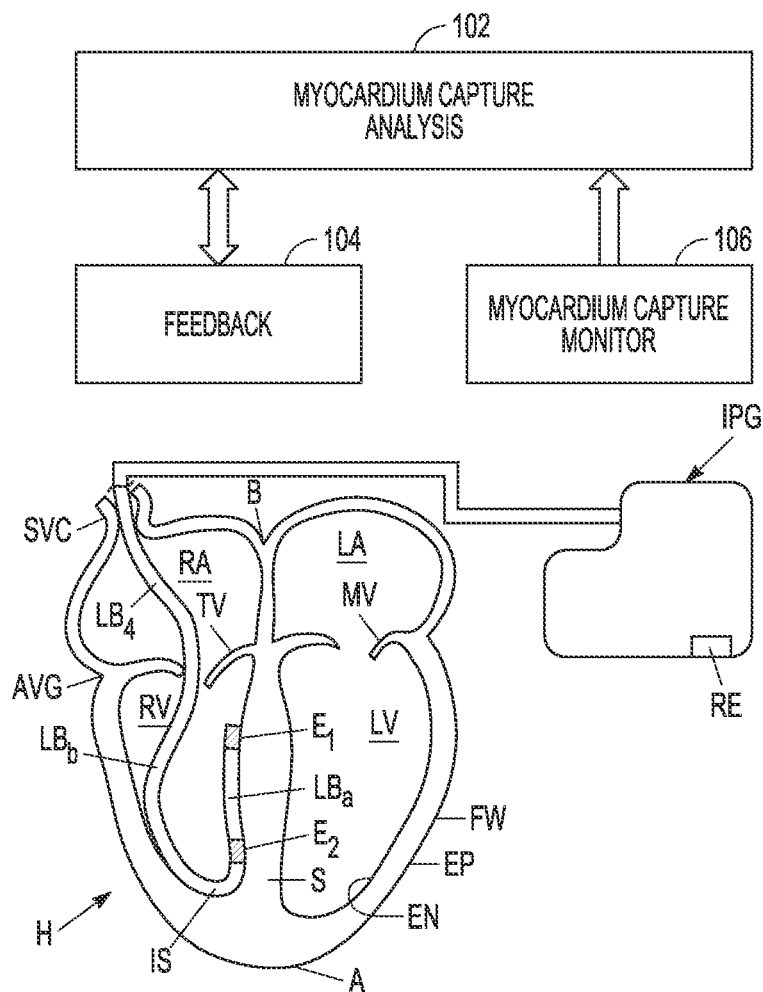
FIG. 21 is a system for determining optimal placement of the electrodes.

FIG. 21 shows a system for selectively placing the electrodes. In a specific embodiment the lead discussed in connection with FIG. 22 may be used. The lead position is adjusted through various methods via conceptual block 104. If desired, the lead position may be monitored and location information may be provided to myocardium capture analysis block 102. Myocardium capture monitor block 106 monitors the effectiveness of the current lead position in capturing and re-synchronizing a contraction of the myocardium of the left and right ventricles. The monitor information is provided to myocardium capture analysis block 102, which processes the received information for the purposes of positioning the electrodes.

In a specific example, monitor block 106 uses ECG measurements to monitor myocardium capture and re-synchronization. Analysis block 102 may analyze various factors of the far field measurements including, but not limited to, the QRS width (e.g., determined from a vectocardiogram). The ECG measurements may be supplied from a number of different inputs including, but not limited to, defibrillation coils, the can of the implantable device, an electrode of a pacing or sensing lead or an external ECG (or similar) device.

In another example, monitor block 106 may measure the amount of blood flow resulting from a contraction of the myocardium.

The system of FIG. 21 may also be used to adjust other re-synchronization parameters. For instance, the voltage levels and waveforms may be adjusted according to feedback from monitor block 106 and analysis from analysis block 102. In particular it has been discovered that careful placement may allow for low voltages to be applied to the electrodes. In one embodiment, the pacing impedance of the lead and electrodes is low to allow for effective delivery of the pacing voltage. This may be useful for reducing the power consumption of the device and for reducing the voltages necessary to deliver the stimulus. By proceeding in this manner, (e.g., using low impedance and maintaining low voltage), phrenic nerve stimulation or diaphragmatic stimulation, both highly undesirable side effects of high pacing, may be avoided.

In a particular embodiment, the lead has a screw with a short screw relative to screws used to reach the left ventricle or the His bundle. This allows for fixation of the lead until encapsulation and helps reduce mechanical problems associated with such attachments. In one instance, the screw may be made from a non-conductive material, thereby electrically isolating the attachment point. In another instance, the screw may be otherwise electrically isolated from the electrodes for delivering the pacing voltage even where the screw is made from a conductive material.

In another embodiment, a hook is used as the attachment mechanism. Yet another embodiment includes the use of a T-bar as the attachment mechanism.

Due to these and other aspects, one of skill in the art would recognize that the use of the reference electrode, as discussed herein, may be optionally implemented to provide effective re-synchronization. In one such instance, the reference electrode is used to provide a reference voltage derived from the in vivo voltage at a particular location. This reference may be used to reference the voltage provided at the stimulus location to the particular location. For example, the reference location may be taken at the can location or from a reference electrode located near the stimulus location. In another instance, no reference electrode is used.

It has been discovered that selective placement of the electrodes may provide a number of unexpected advantages. More specifically, selective placement of the electrodes along the septum appears to provide re-synchronization of the left and right ventricles even for cases of LBBB where the lesion of the bundle would not be considered proximal. Furthermore, in many instances a large improvement has been seen in the level of synchrony in patients with LBBB and also in patients with moderate or advance HF and conductions defects including LBBB, RBBB and IVCD. For instance, locating the electrodes near an optimal location on the septum has been shown to produce smaller than expected QRS widths. Moreover, the threshold voltages necessary to capture the myocardium of the left and right ventricles or to produce the smaller than expected QRS widths (or indications of improved heart function) may be relatively small.

Figure 24:
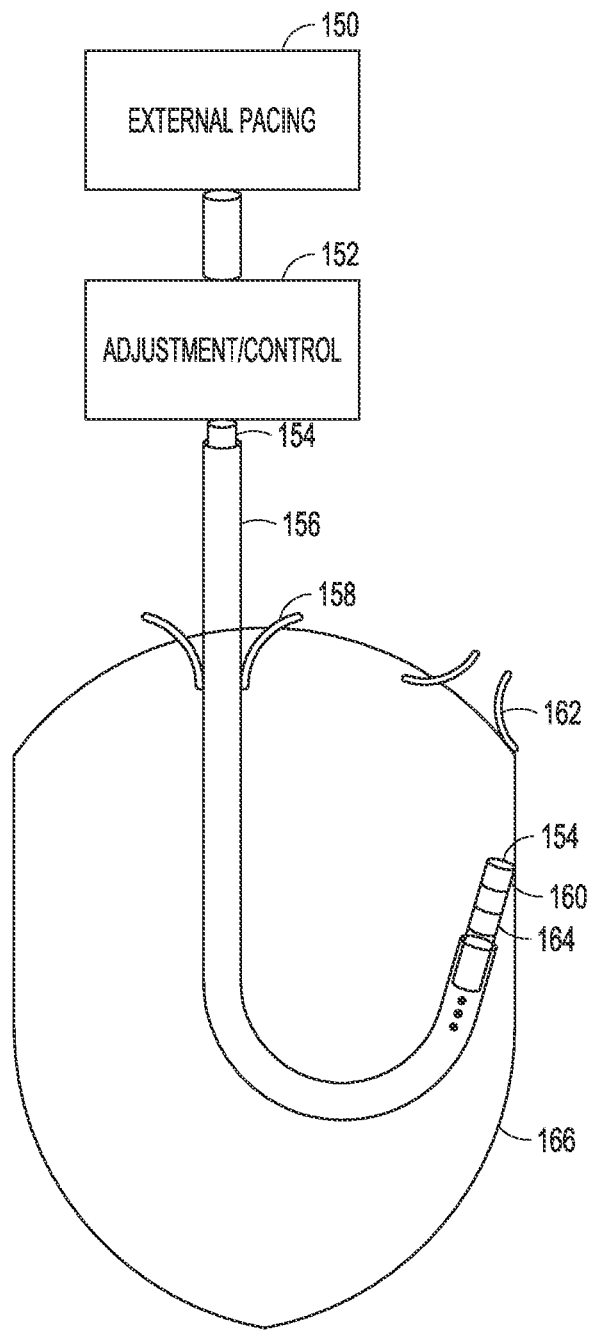
FIG. 24 is diagram of a directable/adjustable catheter-type device useful for delivering certain pulsed waveforms.

FIG. 24 shows an example of a sheath for use within the right ventricle 166 of the heart. The outer sheath 156 is designed to be inserted through the mitral valve 158 and into ventricle 166. Outer sheath 156 may include a J-type bend as shown in the figure. In various applications, this advantageously facilitates the placement of electrodes 160, 164 near the septum and/or the tricuspid valve 162. In one embodiment, one or more of the outer and an inner sheath 154 may arranged to allow directional control of the sheath position (e.g., by allowing for the adjustment of their curvature).

In a specific embodiment, inner sheath 154 is located within outer sheath 156. Inner sheath 154 may be adjusted, relative to outer sheath 156, using adjustment mechanism 152. In one instance, the adjustment mechanism 152 includes an adjustable track wheel or another similar mechanism. Additionally, inner sheath 154 may contain a pacing lead and/or a guide wire for additional stability. The adjustment of inner sheath 154 may be accomplished through a number of different techniques. According to one such technique, the inner sheath is allowed freedom to advance through the outer sheath and to move along the septum. In another example technique, the inner sheath may be arranged to direct the lead placement (e.g., by allowing for the adjustment of its curvature). The inner sheath and/or the outer sheath may have an electrode at their tip to use for pace mapping the locus for Xstim (following procedures discussed herein). Thus, facilitating the insertion of the chronic pacing lead. The inner and out sheaths may be peelable so that the pacemaker lead is kept in place while the sheaths are removed.

External pacing device 150 provides electrical pulses to the electrodes 160, 164. The positioning of the electrodes 160, 164 may be adjusted and the effectiveness of each position may be monitored. Various examples of suitable monitoring techniques are discussed in more detail herein. In some variations, the adjustment mechanism includes a number of fixed settings that can be reproduced. This allows for easily retrievable positioning of the electrodes 160, 164 as correlated to the effectiveness of each position. For example, the inner sheath may be advanced along positional settings 1 through 10 and corresponding monitoring input may be used to determine which setting is preferred. The inner sheath may then be set to the preferred setting after a comparison between the results corresponding to each of the tested settings.

In one embodiment, each electrode may be selectively and independently used to stimulate a synchronous contraction. The voltages for each electrode are varied to determine voltage threshold necessary to produce ventricular capture or to produce improved heart function. Low average stimulation voltage and current may be obtained by selecting the electrode that has the lowest effect threshold (effect refers to resynchronization effect or to maintaining synchrony of the contraction during pacing effect).

In one embodiment, the outer and inner sheaths may then be removed. A number of techniques may be used for such a removal. Using one such technique a guide wire is advanced through the sheaths and is used to hold the pacing lead in place while the sheaths are removed. In another technique, the sheaths are constructed with a slit that allows for their removal from the pacing lead without significant force being applied to the pacing lead.

In one embodiment, the inner sheath may function as a temporary pacing device connected to an external pacing source. The external pacing source may advantageously be equipped with additional processing and display capabilities (relative to an implantable device, which is often limited due to battery life and physical size constraints) to assist in locating the proper placement location. The inner and outer sheaths may be removed once the pacing lead is attached. The pacing lead may also be connected to an implantable device.

In a specific instance, the external device operates to provide a variety of different voltage waveforms and/or stimulus timings to the stimulus location. Feedback from an ECG or other device may be used to identify the preferred waveforms. The implantable device may then be uploaded with corresponding information for use in providing stimulus. In one such instance, the pacemaker may include a wireless port that allows an external interface to monitor and/or adjust the pacing functions. In this manner, the external device need not provide the stimulus through the external sheath. Instead, the implantable device may deliver the same set of stimulus using the wireless interface.

In another instance, the outer sheath may be designed with a removable interface that is compatible with both the external pacing device and the implantable pacing device. This allows for the use of the external pacing device during placement of the electrode(s) and use of the same outer sheath with the implantable pacing. This may be particularly useful for reducing the size of the sheath, the cost of the device or for simplifying the procedure by avoiding the step of removing the outer sheath.

In connection with the various drawing figures and relevant discussions, the following disclosures are incorporated herein by reference in their entirety: U.S. Pat. No. 6,230,061 B1 to Hartung issued May 8, 2001, for details of a cardiac pacemaker with localization of the stimulating pulses and U.S. Pat. No. 6,907,285 to Denker, et al., dated Jun. 14, 2004, for details of a wireless defibrillation system; U.S. patent application Publ. No. 2004/0153127 published Aug. 5, 2004 for details related to the use of a microstimulator in the proximity of at least one anatomical structure to produce muscular contractions; U.S. Pat. No. 6,643,546 B2 to Mathis et al. dated Nov. 4, 2003, for details related to the treatment of congestive heart failure.

Figure 24A:
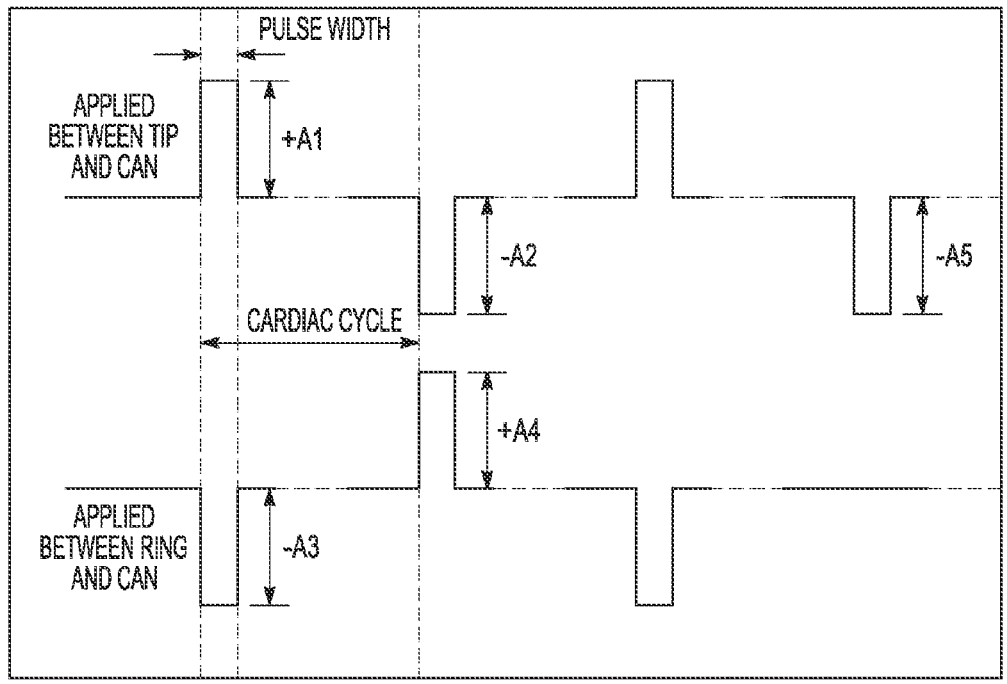
FIGS. 24A, 24B, 24C and 24D depict a graphical representation of pulsed waveforms to be applied by the electrodes of the various embodiments.
Figure 24B:
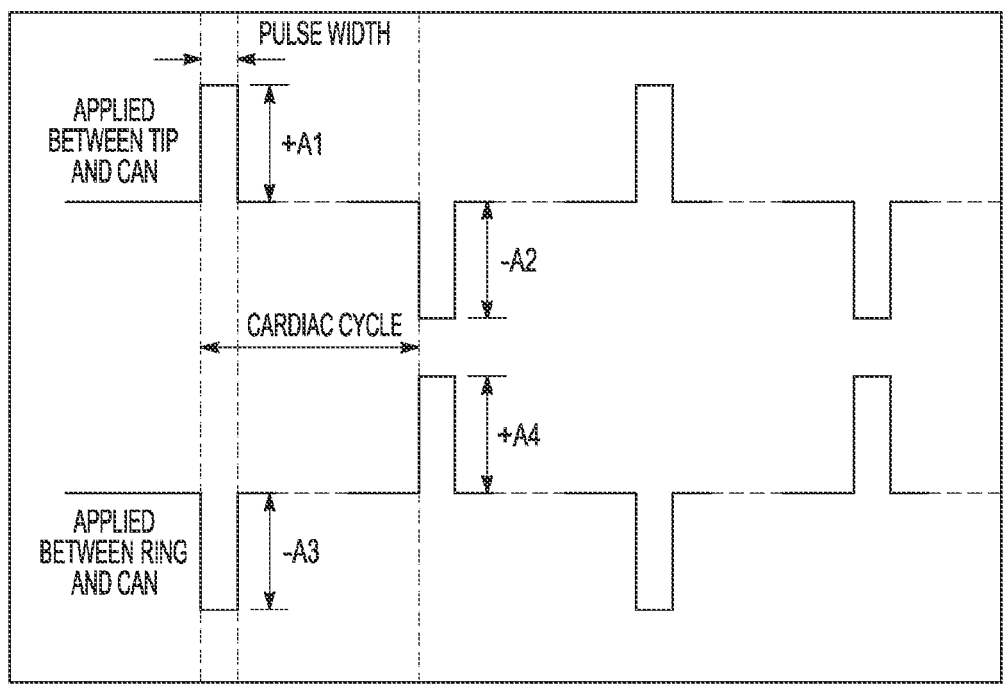
Figure 24C:
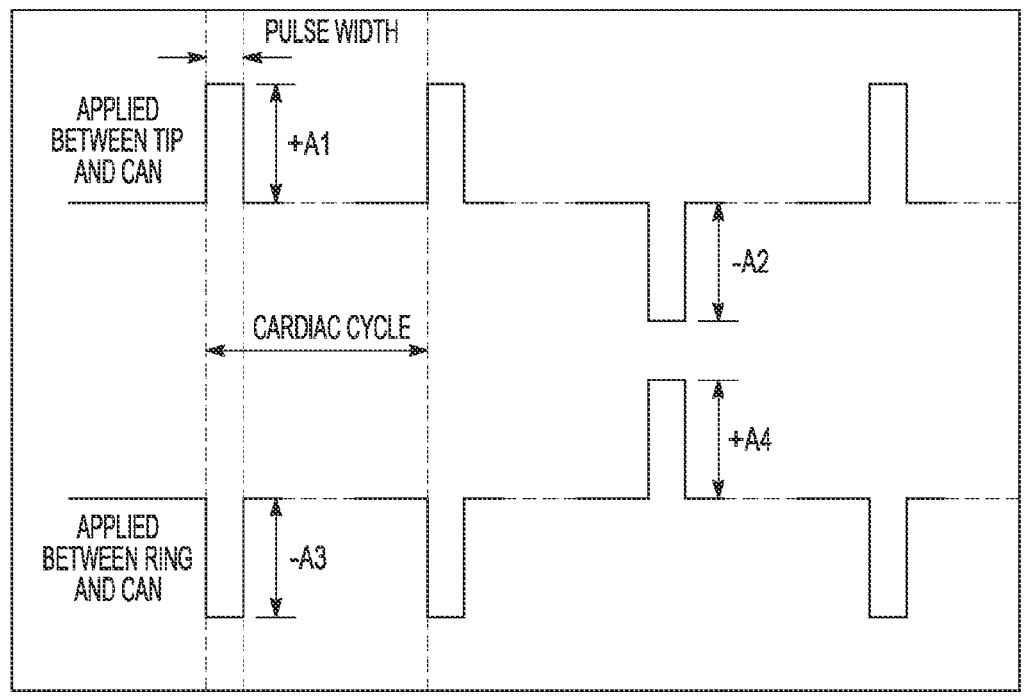
Figure 24D:
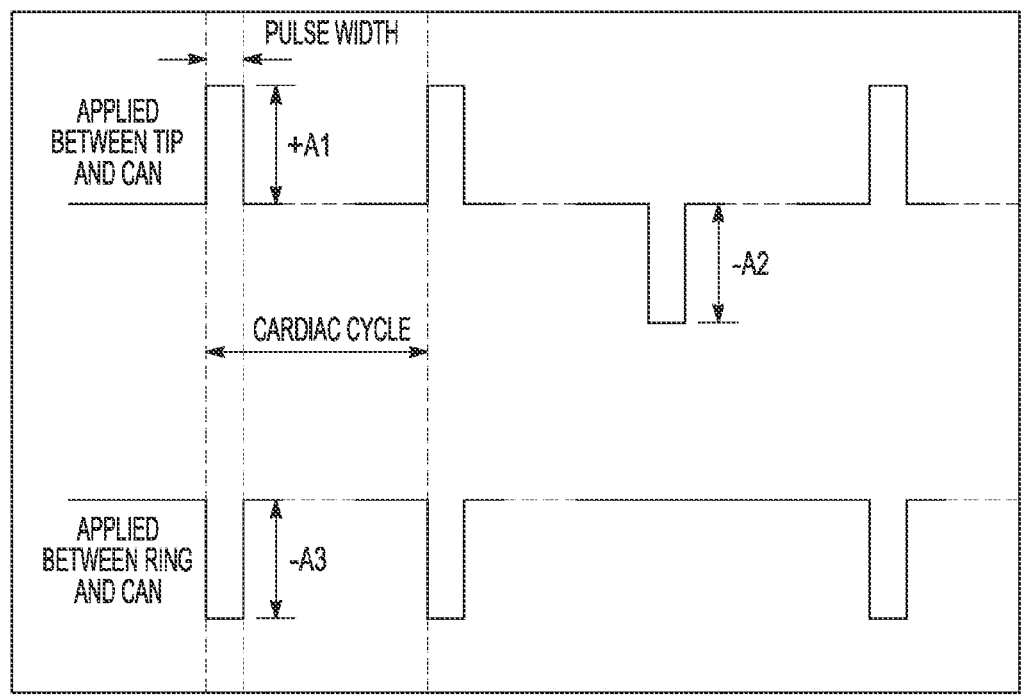

Consistent with these and other example embodiments of the present invention, FIGS. 24A-D depict additional waveform patterns that may be provided by an electronic circuit. For example, FIG. 24A shows pulses A1, A2 and A5, which represent voltages applied to a first electrode (e.g., the voltage differential between the tip and the can), while pulses A3 and A4 represent voltages applied to a second electrode (e.g., the voltage differential between the ring and the can). Control logic in the pacemaker device allows for the individual adjustment of the voltage amplitude of the various pulses and for the adjustment of the pulse width or duration. The specific parameters may be implemented by iteratively changing the waveforms and monitoring the effectiveness of the pulse. For instance, the selection of the ideal waveform may be made by selecting the waveform that produces the smallest QRS width as measured by an ECG. While FIG. 24A depicts the pulse polarity as alternating each beat, it should be apparent from the discussion herein and from FIGS. 24B-C that this is merely one example of a possible pulse modulation scheme.

In a particular embodiment, one or more pulses may be withheld as shown by the lack of a pulse on the ring electrode that corresponds to pulse A5 on the tip. In this sense the ring electrode pulse has effectively been withheld or skipped. In certain embodiments, either or both of the pulses may be withheld. Such withholding of pulses may be periodically implemented (e.g., once per every N pulses, or once every 20 minutes per 24 hours to allow heart to be conditioned by its own intrinsic contraction if the intrinsic heart rate is above a certain acceptable rate, such as 50 beats/minute). In another instance, the withholding may be responsive to feedback from a sensing electrode or ECG input.

It has been reported in literature that a small percentage of conventional RV apical pacing, which has been shown to be detrimental to the cardiac function, provided benefits to the overall patient wellbeing due to the healthy sympathetic and parasympathetic exercises introduced by the sporadic cardiac stress associated with RV pacing. As the pacing disclosed herein (including Xstim pacing) has been shown to resynchronize the LV ventricle, reducing the stress level of the diseased hearts, the withholding of (Xstim) pacing signals periodically or sporadically is useful to improve the overall patient wellbeing.

As discussed herein in connection with various aspects of the methodology useful for implementing the present invention, an example procedure for determining placement of a lead for pacing involves at least one repetition of pacing, sensing and repositioning using at least one lead adapted to deliver a pacing profile. While, not all of the data shown in the various figures was implemented as part of the experimental tests discussed herein, it is believed that the data shown is accurate. In a specific implementation of this procedure, pacing of the heart is accomplished using a lead placed in the right ventricle and near the His bundle. For example, the lead can include two electrodes (and in some instances one) to deliver oppositely charged pulses. Heart functionality associated with the pacing then is monitored. The monitoring can include one or more of the following examples, ECG readings (e.g., QRS width or fractionation), electrical activity of a late activation site in the left ventricle, mechanical contraction of the heart or measurement of the blood flow (e.g., the rate of change in pressure). The lead is repositioned and pacing and monitoring can be repeated.

Once a desired lead placement has been selected, pacing can be implemented in various ways. For instance, DDD (dual chamber) pacing can be implemented with or without a low atrial rate (e.g., around 50 beats per minute) and an AV delay of around one-half of the baseline or intrinsic AV interval. The DDD pacing can also be modified to use a variety of different Xstim pacing profiles, non-Xstim pacing profiles and combinations thereof.

Also according to an embodiment of the present invention, a way to assess improved heart function involves determining placement of a lead for sensing a late activation site in the left ventricle. The lead, which is capable of sensing electrical activity in nearby heart tissue, is advanced through the CS (coronary sinus) until monitoring results from the lead represent activation of a late activating region. The lead can be continuously advanced until activation of a distal electrode on the lead no longer occurs before any other electrode(s) on the lead. At this point, the current lead position can either be maintained or the lead can be slightly retracted.

While not bounded by theory, experimental data provides strong support that the beneficial effects on cardiac function provided by aspects of the present invention are due, at least in part, to His bundle stimulation. The data further supports that, unexpectedly, the His bundle may react more like a nerve than a myocyte with respect to responsiveness to electrical stimulation. This may be due in part to fibrotic encapsulation of the His bundle.

It is possible that the success of Xstim pacing can be attributed in part to the phenomena of anodal break stimulation in tissues with high directional anisotropy. It is also possible the success of Xstim pacing can be attributed in part to a phenomenon sometimes referred to as accommodation. Accommodation is an increase in voltage threshold necessary to produce depolarization of a nerve cell that occurs when the nerve is exposed to a non-zero voltage that is below the threshold voltage.

Figure 25A:
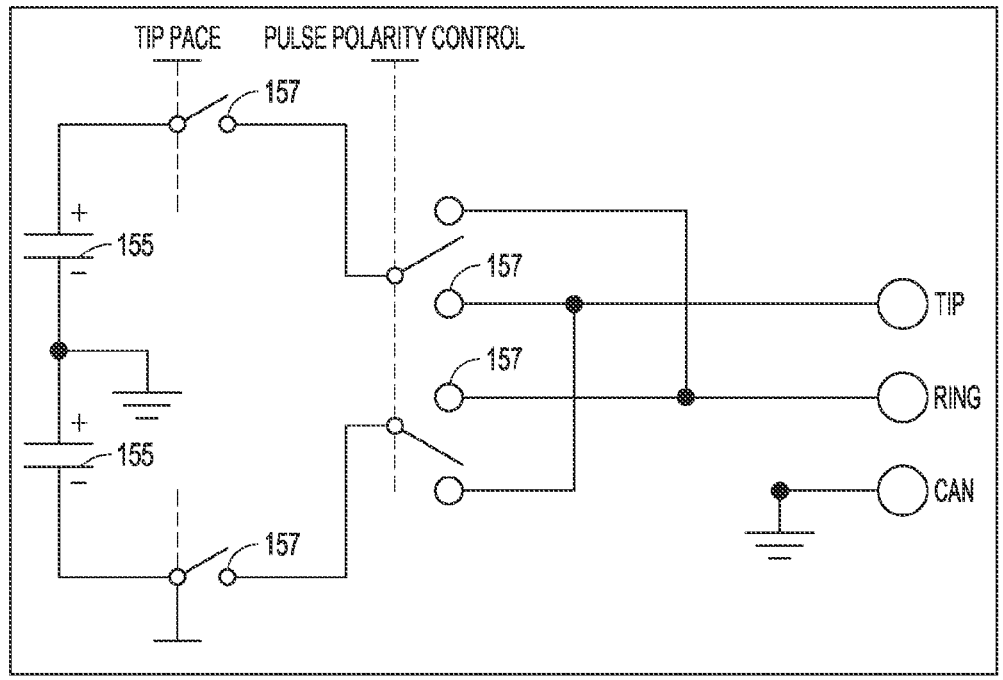
FIGS. 25A and 25B illustrate examples of electronic circuits (the latter including capacitive isolation) for applying pulse patterns for application by the electrodes as useful with the various embodiments discussed herein.
Figure 25B:
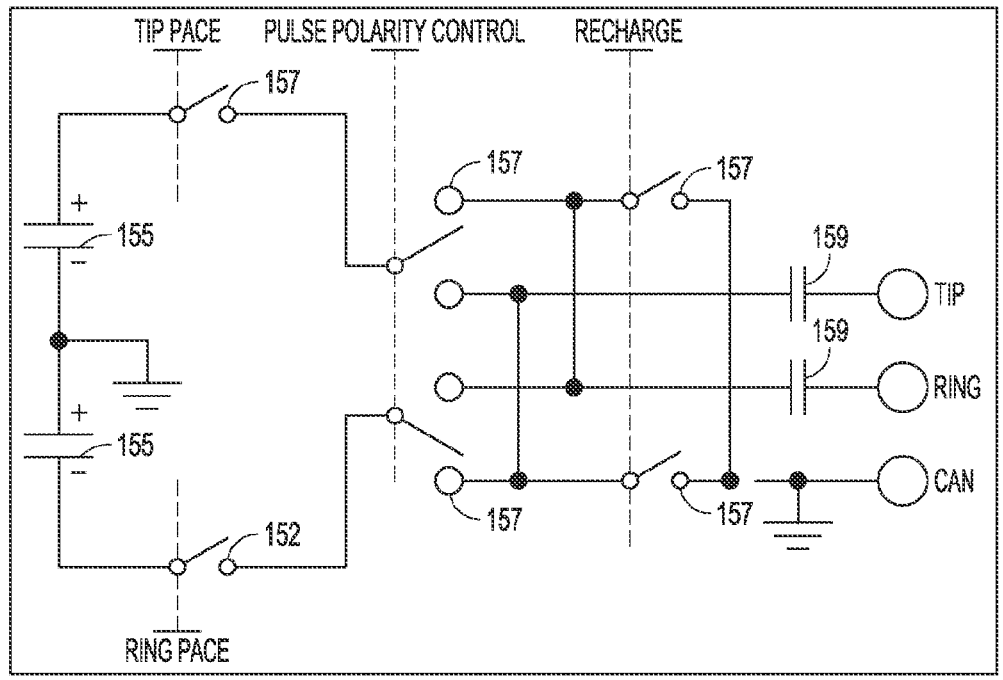

As example ways for generating signals to provide Xstim pacing, FIGS. 25A and 25B are illustrative. As discussed above, specific parameters may be implemented for generating the waveforms, including but not limited to Xstim pacing signals, and monitoring the effectiveness of the pulses for selecting the appropriate response/treatment. Each of FIGS. 25A and 25B depicts an electronic circuit for applying pulse patterns for application by the electrodes. While there are various ways to implement the pacing outputs outlined above. The circuits shown in FIGS. 25A and 25B are specific examples and are not meant to be exclusive of other possible designs, as many other (hardware- and/or software-based) signal-generation arrangements are feasible.

In accordance with FIG. 25A, the pacemaker has two pacing output capacitors 155 each of which is capable of being charged opposite from the other. In one instance, the amplitudes of the voltage on each capacitor can be varied independently. Each of the capacitors can be connected to Tip or Ring electrode via controlled switches 157. In one embodiment, the switches 157 allow for the output capacitors 155 to discharge (pacing) via the Tip and Ring electrode on a beat-by-beat basis.

In another embodiment shown by FIG. 25B, isolation capacitors 159 are contained in the circuitry. The output capacitor may alternate their discharge (pacing) in any combination of the polarity assignment. The isolation capacitors 159 are used for the charge neutralization at the tissue electrode interface.

In a particular instance, isolation capacitors 159 provide AC (capacitive) coupling between the tip/ring electrodes and the pulse source (capacitors 155). As such, the isolation capacitors 159 may provide a number of additional benefits. For example, by decoupling the DC signal components of the tip/ring electrodes from the pulse source, the DC reference component present on each side of the isolation capacitors need not be the same. For example, the DC component of the reference voltage at the can need not be the same as the DC component of the voltage at the tip/ring electrodes.

Additional switches may be used to connect the source side of isolation capacitors 159 to source ground. This may be useful for ensuring that the application of the pulse from the capacitors 155 produces the desired voltage spike, thereby producing the desired AC component (voltage change) across isolation capacitors 159. Moreover, AC coupling may be subject to DC drift where the AC components are not balanced. Such drift may sometimes be avoided by applying a balanced signaling component (i.e., equal negative and positive pulses applied to the capacitors). The use of a reference ground may also be used to remove DC drift components.

It is noted that in various implementations and patient-specific applications, the common signal ("CAN" ground of FIGS. 25A and 25B) may not be important.

Figure 26A:
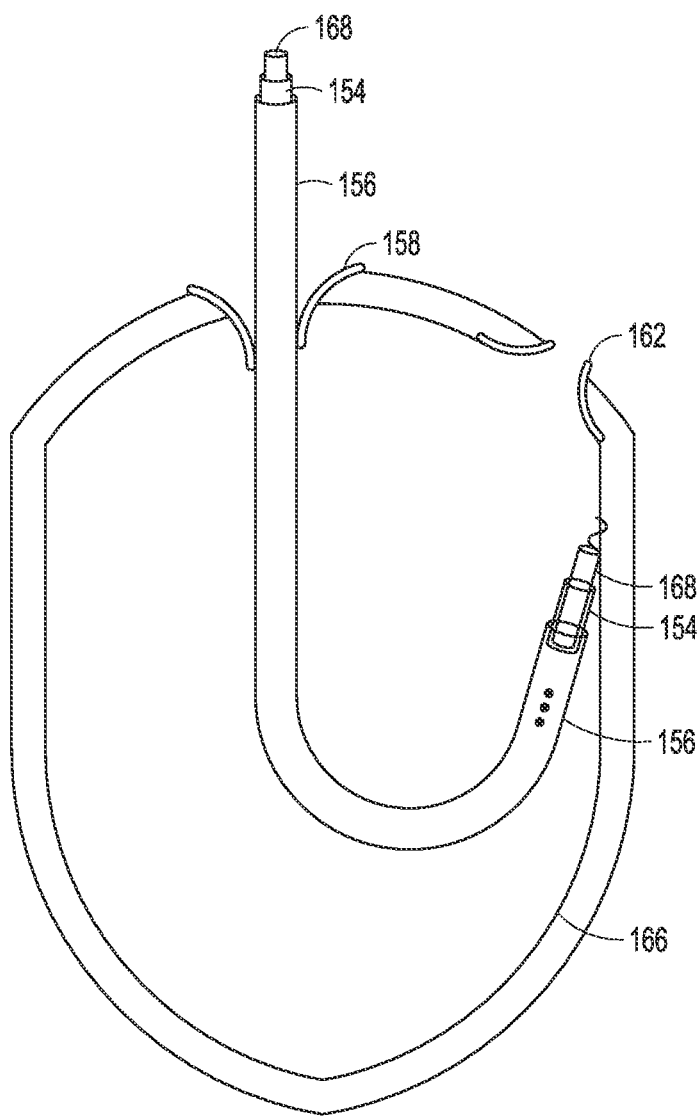
FIGS. 26A and 26B illustrate catheter arrangements useful with the various embodiments discussed herein.
Figure 26B:
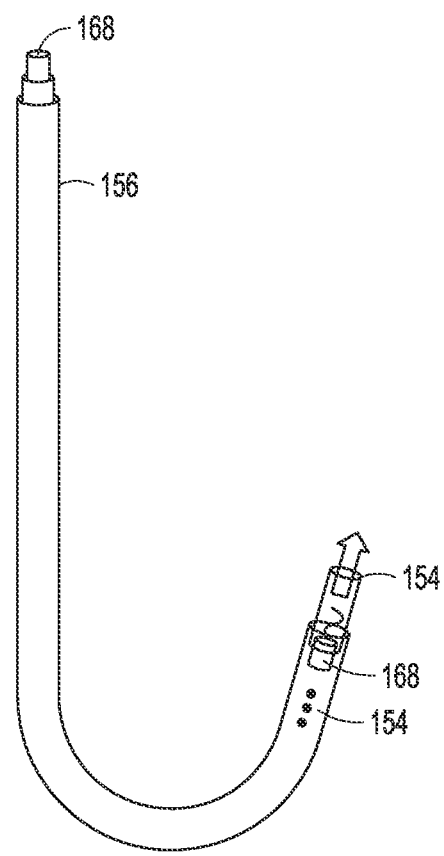

FIGS. 26A and 26B show an example of a pacing lead 168 that includes a fixation mechanism and that is located within the inner sheath 154. In one embodiment, such a catheter arrangement uses a screw attachment as a fixation mechanism to attach the catheter arrangement to heart tissue, and individually-addressable electrodes (such as $E_1$ and $E_2$ illustrated supra) for providing pacing signals to the heart tissue, and an elongated structure that supports the fixation mechanism and the electrodes. The elongated structure is used to direct an end thereof to the target region in the right ventricle, and deliver pacing signal (e.g., Xstim) to different portions within the target region of the heart when the fixation mechanism is operative to attach to heart tissue and also when the fixation mechanism is not attaching the catheter arrangement to heart tissue.

As shown in the specific embodiment of FIG. 26A, the pacing lead 168 may be attached to the septum once the proper placement location has been determined. The pacing lead 168 may be attached using a screw, tines or other suitable attachment mechanisms.

As shown in FIG. 26B, the inner sheath 154 may be moveable with respect to the outer sheath 156. In particular, FIG. 26B shows the inner sheath 154 being extended from the end of outer sheath 156. Moreover, pacing lead 168 may be moveable with respect to inner sheath 154. In FIG. 26B, pacing lead 168 is shown without the attachment mechanism protruding from the outer sheath 156. According to one embodiment, the pacing lead 168 may be maintained in such a position until the proper placement location is determined. The pacing lead 168 may then be advanced and attached to the location using attachment mechanism as shown by FIG. 26A.

In one embodiment, the outer and inner sheaths may then be removed. A number of techniques may be used for such a removal. Using one such technique a guide wire is advanced through the sheaths and is used to hold the pacing lead in place while the sheaths are removed. In another technique, the sheaths are constructed with a slit that allows for their removal from the pacing lead without significant force being applied to the pacing lead.

In one embodiment, the inner sheath may function as a temporary pacing device connected to an external pacing source. The external pacing source may advantageously be equipped with additional processing and display capabilities (relative to an implantable device, which is often limited due to battery life and physical size constraints) to assist in locating the proper placement location. The inner and outer sheaths may be removed once the pacing lead is attached. The pacing lead may also be connected to an implantable device.

In a specific instance, the external device operates to provide a variety of different voltage waveforms and/or stimulus timings to the stimulus location. Feedback from an ECG or other device may be used to identify the preferred waveforms. The implantable device may then be uploaded with corresponding information for use in providing stimulus. In one such instance, the pacemaker may include a wireless port that allows an external interface to monitor and/or adjust the pacing functions. In this manner, the external device need not provide the stimulus through the external sheath. Instead, the implantable device may deliver the same set of stimulus using the wireless interface.

In another instance, the outer sheath may be designed with a removable interface that is compatible with both the external pacing device and the implantable pacing device. This allows for the use of the external pacing device during placement of the electrode(s) and use of the same outer sheath with the implantable pacing. This may be particularly useful for reducing the size of the sheath, the cost of the device or for simplifying the procedure by avoiding the step of removing the outer sheath.

In one embodiment, the inner sheath may have an electrode in its tip to function as a temporary pacing device connected to an external pacing source. The external pacing source may advantageously be equipped with additional processing and display capabilities (relative to an implantable device, which is often limited due to battery life and physical size constraints) to assist in locating the proper placement location. The inner and outer sheaths may be removed once the pacing lead is attached. The pacing lead may also be connected to an implantable device. In another embodiment this electrode may be placed on the outer sheath, with the inner sheath not utilized at all. In still another embodiment a fixed shaped sheath with an electrode in the tip for pace mapping may be used, the fixed shape is selected from a catalog of shapes to mimic the particular patient's shape of the access trajectory from the superior vena cava, to the region of the His bundle, rather than being a steerable sheath.

Embodiments of the present invention are directed to stimulation catheters, systems and methods that employ two or three electrodes and that can be used in connection with the various methods and systems discussed herein. In specific embodiments of the present invention, the most distal two electrodes are located at the tip of the catheter. An optional third electrode can be located in a number of places, such as on the lead body some distance from the first pair or even located between the pairs. The distance from the third electrode and the distal pair ranges from a few millimeters to a few centimeters. The catheter can have a helical fixation structure which can be either a passive (non-electrical) or active (serving as one of the tip electrodes). The catheter can be transvenously placed within the heart. The catheter is arranged such that once affixed to the heart tissue, the two pacing electrodes are in direct electrical contact with the cardiac tissue once. Experimental data suggests that such features can be useful for providing low and stable thresholds during standard pacing. It has also been observed that two pacing electrodes in contact with the wall can be useful in finding a stimulation region in the right ventricle that depolarizes the heart in a manner very similar to the normal activation sequence created by the normal intrinsic (originating in the sinus node) activation propagating through the His-Purkinje system.

Various embodiments can be implemented where the two stimulating electrodes are in direct contact with the heart tissue. For instance, one or more small porous conducting dots may be attached to the ring electrodes to increase the microscopic surface area (effective surface at the reactant level of physical interaction), and the helix electrode may be coated with material(s) to also increase the microscopic surface area. In various implementations, porous and raised portions of the electrode take the form of any number of shapes (e.g., lines, circles, squares or zig-zags). One implementation involves scoring the electrode (e.g., using a laser or etching). Other implementations can include nanostructures (e.g., nanowires and/or nanotubes) that are located on the contact surface of the electrodes. Such nanostructures can provide significant increase in contact surface area. Additionally, certain anti-inflammatory agents (e.g., a steroid) can be administered with the active fixation pacing catheter can be implemented.

One configuration is implemented in connection with methods and devices so as to provide sufficient contact surface area between the cardiac tissue and the electrode(s). Resistance between the electrode and the cardiac tissue can affect signals (e.g., pacing or sensing signals) transmitted between the heart tissue (including the conduction system of the heart) and the electrode. Generally speaking, the resistance of a conductor is inversely proportional to the cross-sectional area of the conductor with respect to the direction of current flow (e.g., R=resistivity*length/cross-sectional area). Increasing the surface area of the electrode(s) that contacts the heart tissue can be particularly useful for detection of intrinsic cardiac depolarization signals.

One implementation involving the use a circuit is as follows. In a detection mode, the two electrodes are connected to one input of a sensing amplifier through a sensing switch that will be open during simulation to avoid short circuit but closed whenever sensing is needed. The other input of amplifier will be either connected to the stimulator CASE for commonly referred as the unipolar sensing or to the optional electrode (if available) for commonly referred as bipolar sensing.

In a pacing mode, stimulation waveform(s), will be applied to the first two electrodes. In one application these waveforms are similar to those used with conventional catheters. Other applications employ stimulation waveforms including, but not limited to, an Xstim waveform and/or two simultaneous opposite polarity stimulation pulses with reference to either the case or the third electrode (if available).

Figure 27A:
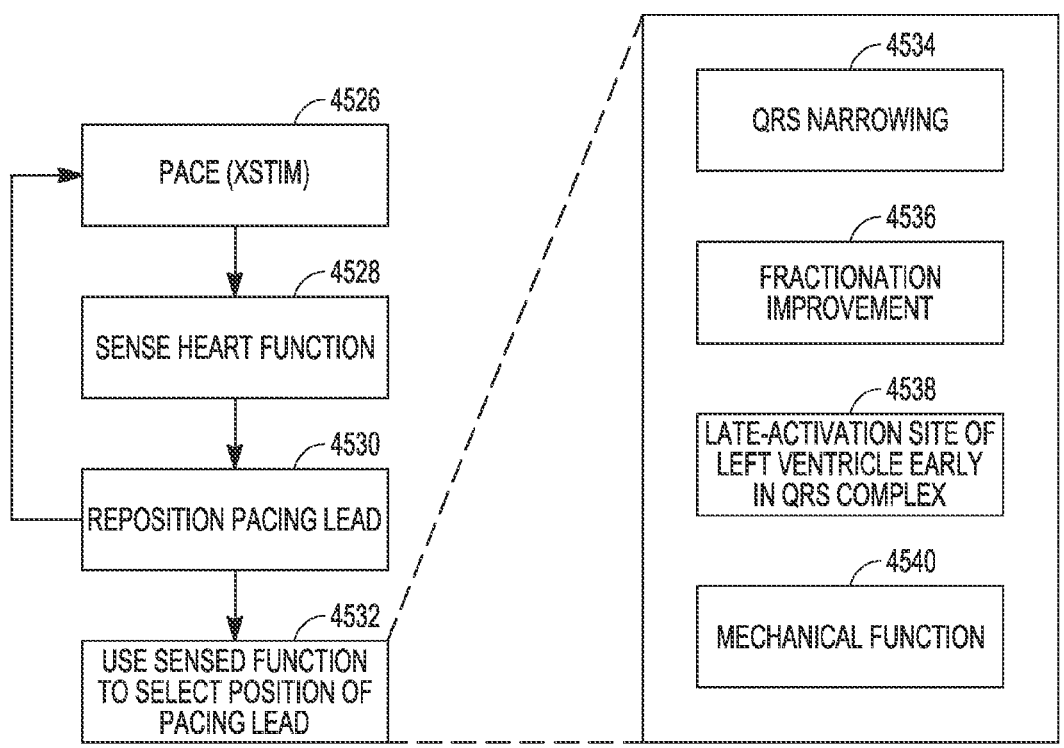
FIGS. 27A, 27B, 27C and 27D illustrate example procedures for determining pacing-lead placement.

FIG. 27A shows an example procedure for determining placement of a lead for pacing according to an embodiment of the present invention. This procedure was implemented to place the pacing lead in connection with the experimental results provided hereafter.

At step 4526, pacing of the heart is accomplished using a lead placed in the right ventricle and near the His bundle. In a specific instance, the lead includes two electrodes used to deliver oppositely charged pulses, such as with Xstim pacing. At step 4528, heart functionality associated with the pacing is monitored. The monitoring can include one or more of the following non-limiting examples, ECG readings (e.g., QRS width or fractionation), electrical activity of a late activation site in the left ventricle, mechanical contraction of the heart or measurement of the blood flow (e.g., the maximum rate of change in left ventricular pressure). In one implementation, the improved heart function can be based upon a comparison of heart function without any pacing. As discussed above, it has been discovered that voltages sufficiently above the capture threshold can lead to improved heart function relative to voltages near the capture threshold. Accordingly, one implementation of pacing uses relatively high voltages (e.g., +/−5V) when pacing to determine lead location. This can be useful to ensure that the improved heart function is seen. When the lead is not yet properly placed, pacing capture can sometimes still be obtained without exhibiting significant improvement in heart function. Thus, the improved heart function can sometimes be an improvement over heart function resulting from use of the pacing lead and pacing profile rather than (or in addition to) the baseline and/or un-paced heart function.

At step 4530, the lead is repositioned and pacing and monitoring steps 4526 and 4528 can be repeated as desired. The results of the monitoring step can be saved and correlated to the corresponding lead positions. At step 4532, the results of the monitoring step 4528 are used to determine the proper placement for the lead. A few examples of the results of the monitoring step are shown by 4534 (QRS narrowing), 4536 (fractionation improvement), 4538 (late activation site earlier) and 4540 (mechanical function improved). The lead can then be moved (back) to the lead position that is selected as a function of the monitoring results.

In another implementation, the steps 4530 and 4532 can be switched so that repositioning of the lead is done after evaluating the results of the monitoring step 4528. In this manner, the lead can be repositioned until satisfactory results are detected. This can be particularly useful for not having to record and recreate lead positions previously paced. Instead, once satisfactory monitor results are found, the current lead placement can be used.

Figure 27B:
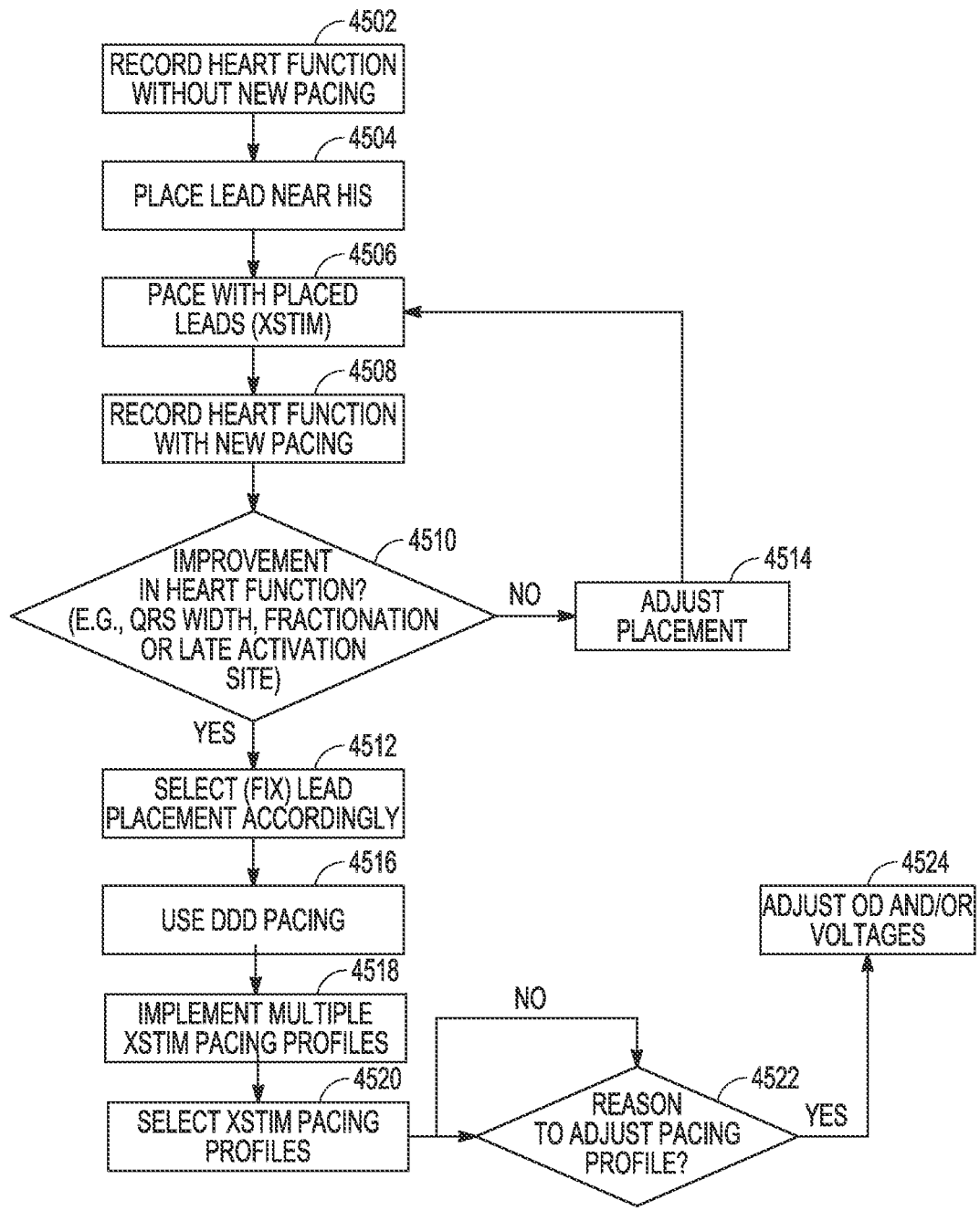

FIG. 27B shows an example procedure for determining placement of a lead for pacing according to an embodiment of the present invention. At step 4502 baseline heart function is recorded (e.g., without Xstim pacing). At step 4504 a lead capable of delivering Xstim pacing is placed near the His bundle (i.e., near the root of the septal leaflet of the tricuspid valve in the right ventricle). At step 4506 Xstim pacing is delivered to the placed lead. In a particular embodiment the Xstim pacing is consistent with the waveforms depicted by and discussed in connection with FIG. 18. At step 4508 the heart function associated with the Xstim pacing is recorded. If it is determined, at step 4510, that Xstim pacing improves heart function (e.g., narrowing of the QRS, less fractionated QRS, improving timing of a late activation site, improved mechanical function or improved pressure function), the placement of the lead can be selected (and fixed) at step 4512. Otherwise, the position of the placed lead can be adjusted at step 4514 and steps 4506-4510 can be repeated as necessary.

In a specific embodiment, the determination step 4510 can implemented using multi-lead ECG readings and a probe placed at a late activation site of the left ventricle (e.g., placing a lead near the posterior lateral wall of the left ventricle via a catheter inserted through the Coronary Sinus).

Once a desired lead placement has been selected, DDD pacing can be implemented as shown in step 4516. In a specific implementation, the DDD pacing is implemented with a low atrial rate (e.g., around 50 beats per minute) and an AV delay of around one-half of the baseline or intrinsic AV interval (to allow for full capture and atrial tracking and ventricular pacing). In an effort to find an acceptable (or optimize) pacing approach, the DDD pacing is modified to use a variety of different Xstim pacing profiles as shown in step 4518. As exemplified at step 4520, one or more of these profiles can be selected from the following non-limiting examples (discussed in terms of a lead with tip and ring electrodes for simplicity), in-phase pulses with positive voltage applied to the tip and negative voltage applied to the ring, in-phase pulses with negative voltage applied to the tip and positive voltage applied to the ring, out-of-phase pulses with opposite polarities applied to respective tip and ring electrodes.

In some instances it may be beneficial to adjust the pacing profile as shown by the determination step 4522. If so determined, the pacing profile can be adjusted in step 4524. For example, pocket stimulation effects, dry pocket or other effects due to chronic stimulation can result in the threshold voltage increasing. It has been discovered that shifting the overlap duration of the pulses (OD) can help compensate for such problems. In another example, the OD can be shifted to allow for lower pacing voltages, even where no dry pocket or other causes are present.

Figure 27C:
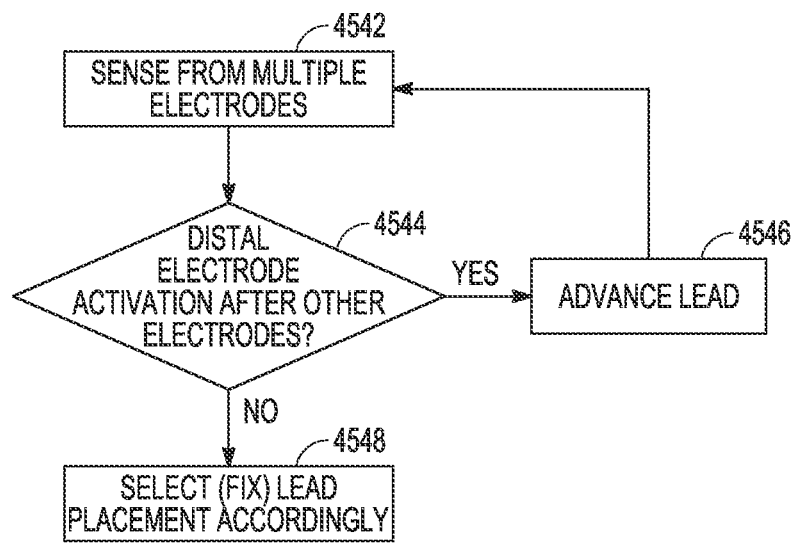

FIG. 27C shows an example procedure for determining placement of a lead for sensing a late activation site in the left ventricle, according to an embodiment of the present invention. As discussed herein, the monitoring of a late activation site of the left ventricle can be useful for placement of pacing lead(s) and/or assessment of pacing effectiveness. The method involves the use of a lead that is capable of sensing electrical activity in nearby heart tissue. The lead is advanced through the coronary sinus until monitoring results from the lead represent activation of a late activating region. In one embodiment, the lead can be advanced to a desired spatial position within the coronary sinus. The lead placement can be determined using a number of different mechanisms, such as fluoroscopy or physical measurements of distance of lead advancements. Each patient, however, may exhibit different morphology and/or electrical conduction/activation. Patients who have conduction abnormalities may exhibit late activation at sites different from patients with normal conduction. Thus, the method depicted by FIG. 27C uses electrical measurements taken from the advancing lead to determine the desired sensing position.

Figure 27D:
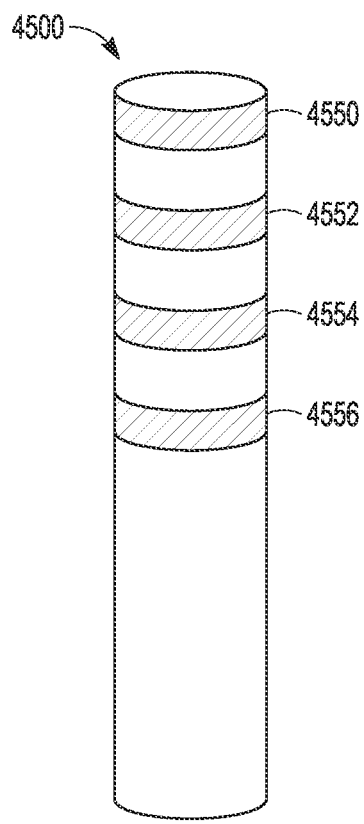

Step 4542 shows that the lead includes multiple sensing electrodes. These sensing electrodes are spatially disparate along the length of the lead. In this manner the most distal electrode represents the electrode that has been advanced the furthest. The remaining electrodes follow. In FIG. 27D, a simplified version of an example lead is shown by lead 4500. The distal sensing electrode 4550 is followed by sensing electrodes 4552, 4554 and 4556.

Once sensing readings are taken from step 4542, a determination is made at step 4544 as to the relationship between the activation times sensed at the sensing electrodes. In particular, if activation of the distal electrode 4550 occurs after activation of the other electrodes, the lead can be advanced further as shown by step 4546. The lead can be continuously advanced until activation of distal electrode 4550 no longer occurs before all of the other electrodes. At this point, the current lead position can either be maintained or the lead can be slightly retracted, as shown by step 4548.

Other implementations are possible, such as using a large number of different sensors. The lead can be advanced a significant distance into the coronary sinus and a particular sensor can be selected (e.g., by selecting a sensor that shows a late activation relative to the other sensors).

In a specific embodiment of the present invention, the absolute amplitude of the voltage presented to one of the electrodes can be less than the absolute amplitude of the voltage presented to the other electrode. This 'unbalanced' pacing profile may provide adequate pacing, while helping to control pacing power.

The power consumption of the pacing device can be an important consideration. While not bounded by theory, it is believed that different pacing profiles can be particularly advantageous to controlling pacing power. For example, during times that the pulses applied to each electrode overlap, the effective voltage seen between the electrodes is believed to be equal to that sum of their amplitudes. During times that the pulses do not overlap, the effective voltage is believed to be about equal to the amplitude of the active electrode. Assuming the voltages of the opposite polarity pulses have equal absolute magnitudes (A), the instantaneous power draw for overlapping pulses is proportional to $4A_2$. The instantaneous power draw for non-overlapping pulses is proportional to $A_2$. For completely overlapping pulses, each having duration T (and thus a total duration of T), the power drawn is then proportional to $4TA_2$. For completely non-overlapping pulses, each having duration T (and thus a total duration of 2T), the power drawn is proportional to $2TA_2$. While it has been observed that non-overlapping pacing profiles may exhibit pacing thresholds that are around 0.5 volts higher than those of overlapping pacing profiles, power savings are still believed to be possible using non-overlapping pulses in place of overlapping pulses.

Figure 28:
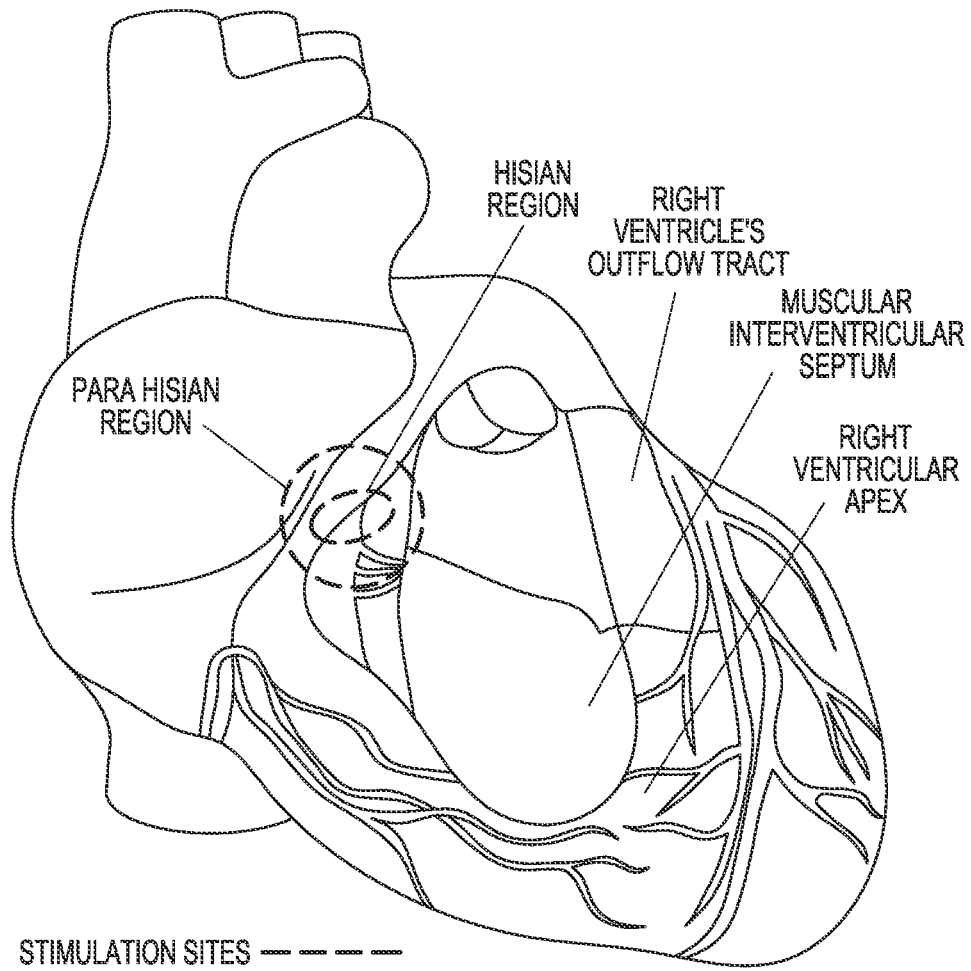
FIG. 28 shows a cross-sectional view of a heart and the Hisian and para-Hisian regions, consistent with an embodiment of the present invention.

FIG. 28 shows a cross-sectional view of a heart and the Hisian and para-Hisian regions. In particular, FIG. 28 is a view of the right side of the heart, with the Hisian and para-Hisian pacing areas shown by the dotted lines. These regions represent the general area in which the pacing sites for the experimental data were collected.

Figure 29:
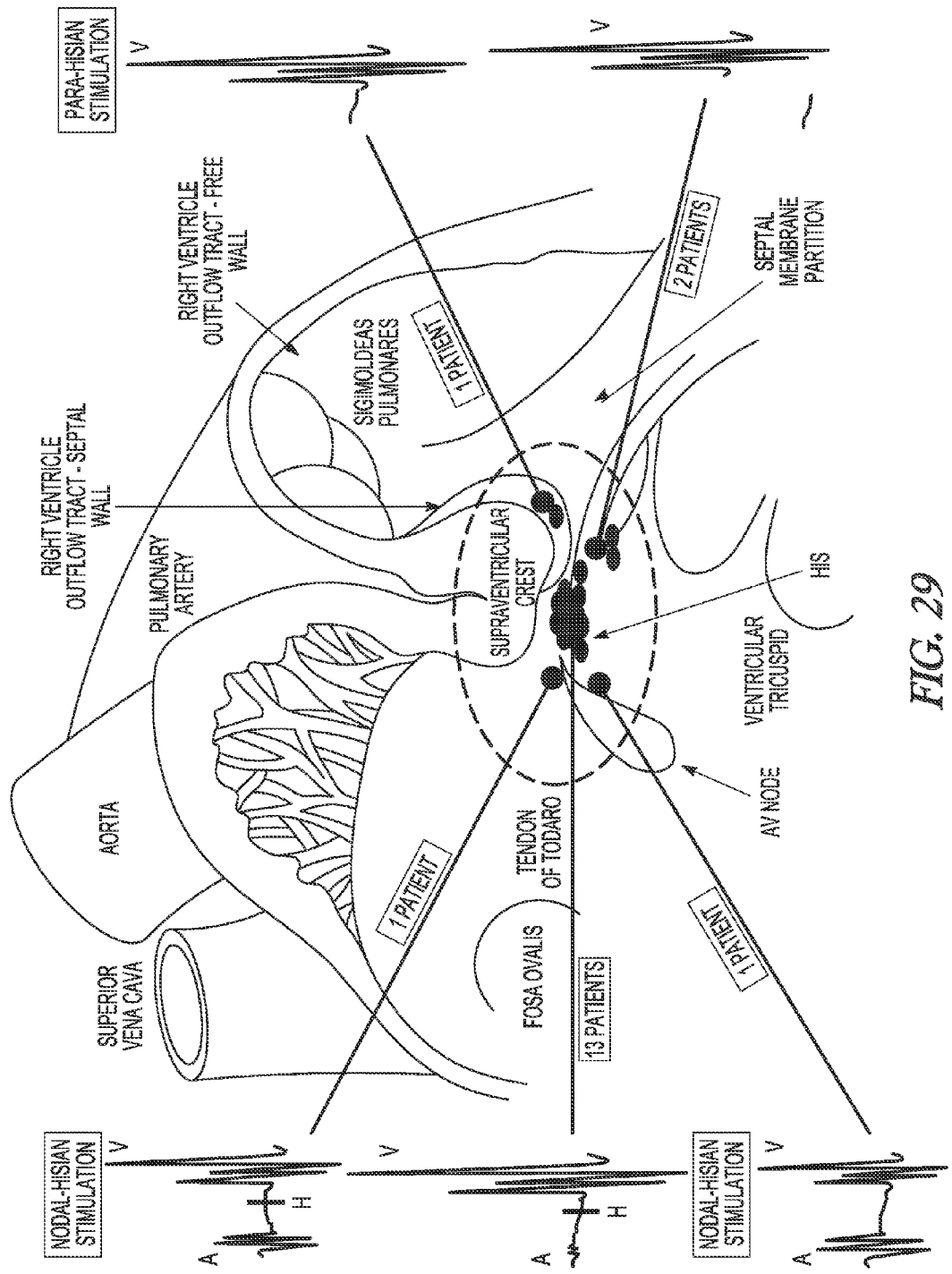
FIG. 29 shows a cross-sectional view of the heart marked with pacing sites.

FIG. 29 shows a cross-sectional view of the heart marked with pacing sites, according to an example embodiment of the present invention. Representative waveforms for different pacing areas are shown along the sides of the figure. The top left waveform represents a pacing site for a single patient and shows significant atrial (A), Hisian and ventricular (V) signals. The middle left waveform represents a pacing site for 13 patients and shows minor atrial signals with relatively strong Hisian and ventricular signals. The bottom left waveform represents a single patient and shows relatively strong atrial and ventricular signals with little Hisian signal. The right two waveforms represent a single patient and two patients, respectively, each with primarily only a ventricular signal.

Figure 30:
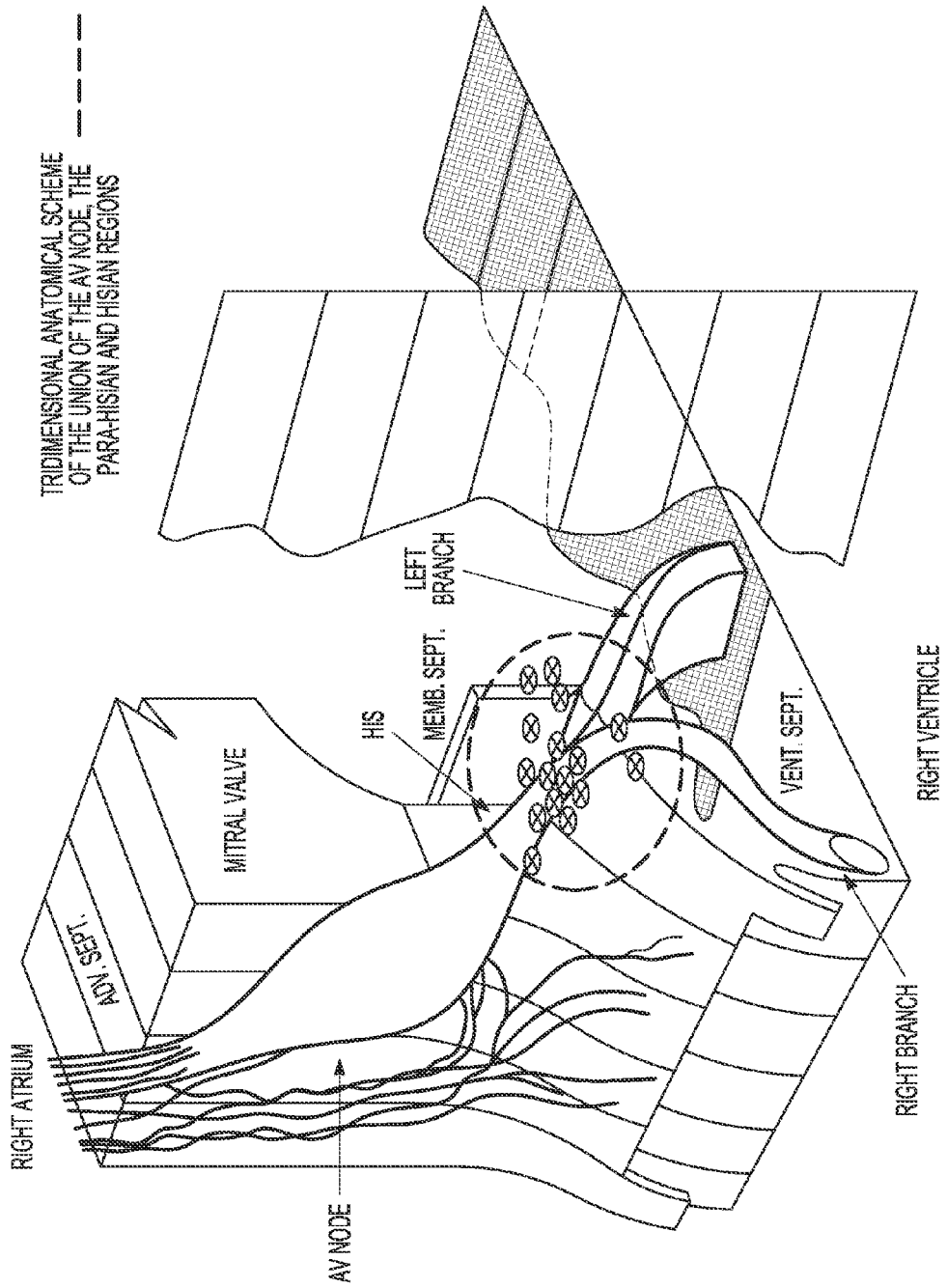
FIG. 30 shows pacing site locations on a 3-D depiction of the union of the AV node, the para-Hisian and Hisian regions.

FIG. 30 shows the location of pacing sites on a three-dimensional depiction of the union of the AV node, the para-Hisian and Hisian regions.

Figure 31:
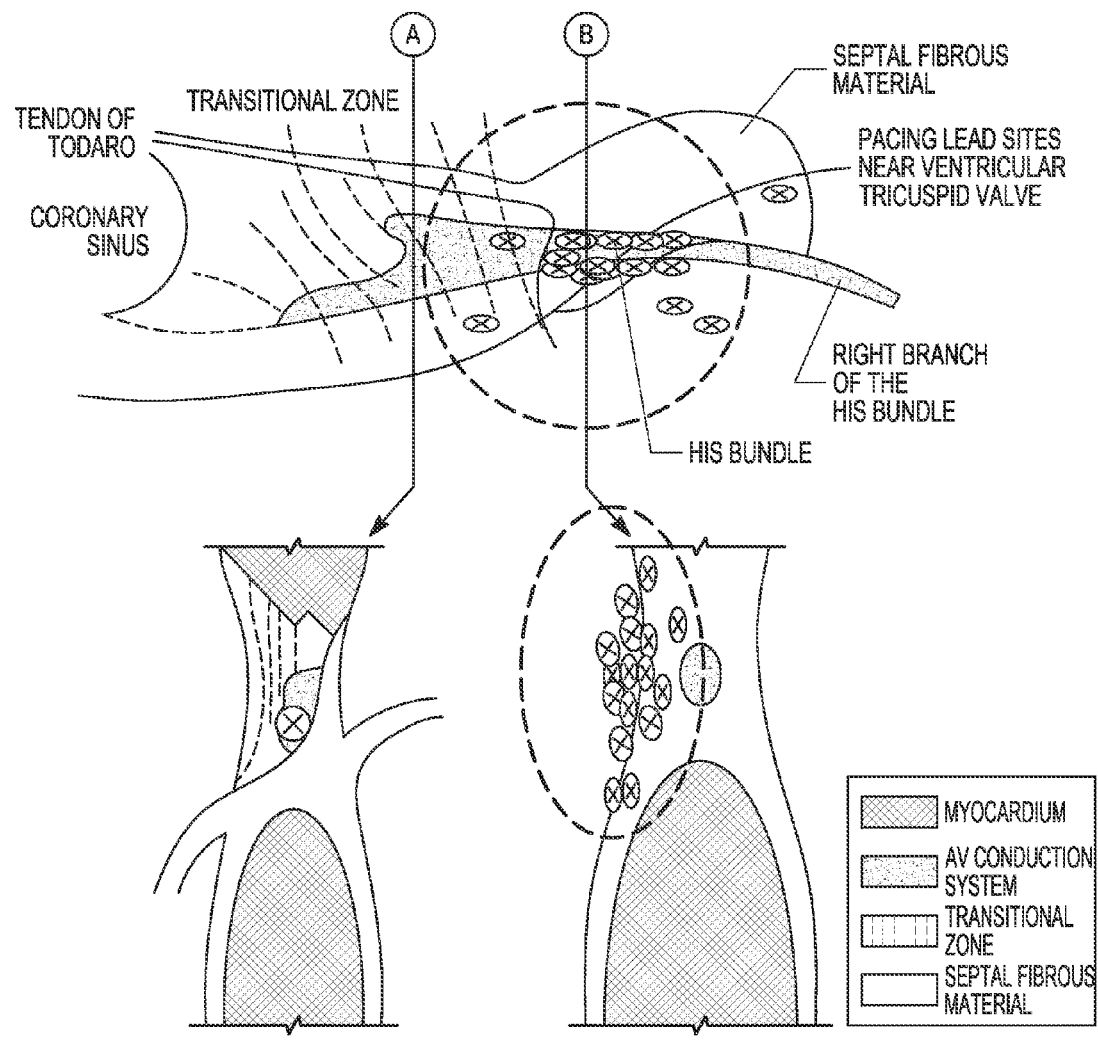
FIG. 31 shows pacing site locations on cross-sectional views of the heart.

FIG. 31 shows the location of pacing sites on several cross-sectional views of the heart. The upper view is a sectional view that includes part of the conduction system that includes the AV node, the His bundle and the right bundle branch. The lower two views show respective perpendicular views taken at respective portions of the conduction system of the upper view.

Figure 32:
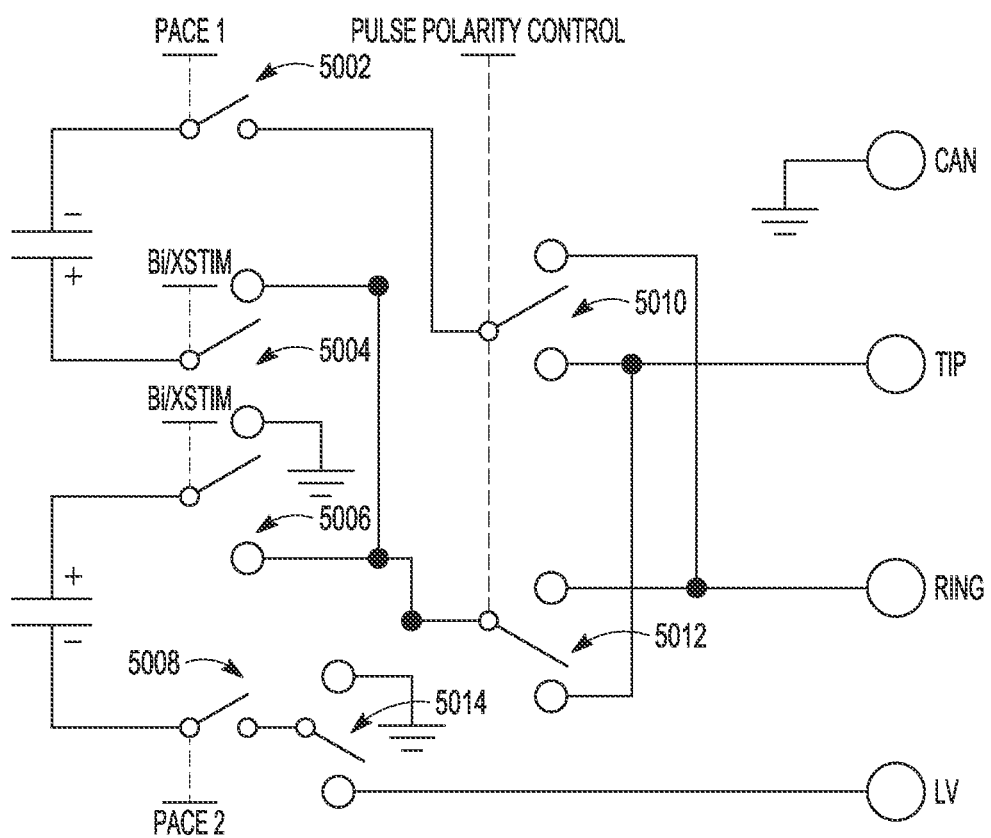
FIG. 32 shows an example circuit for providing various stimulation profiles.

FIG. 32 shows an example circuit for providing various stimulation profiles, according to an example embodiment of the present invention. Switches 5002 and 5008 are enabled to produce a pacing event. Switches 5004, 5006, 5010, 5012 and 5014 are set to provide a variety of pacing profiles. Switches 5004, 5006 and 5014 provide the ability to switch between bi-ventricular pacing and single-ventricle pacing (e.g., Xstim). Switches 5010 and 5012 provide the ability to modify the polarity of the pulses applied to the various electrodes.

In a first configuration, switches 5004, 5006 and 5014 are set for Xstim pacing. Switches 5004 and 5014 are connected to the ground (e.g., to the can or reference electrode). Switch 5006 is connected to switch 5012. In this manner both positive and negative voltages are delivered to the ring and tip electrodes as determined by switches 5010 and 5012. While the term ring and tip are used in connection with the circuit of FIG. 32, the electrodes need not be so limited. For instance, while the tip electrode is closer to the distal end of the lead, the tip electrode need not be located on the distal tip. Moreover, the ring electrode could be something other than ring as various other electrode configurations are possible.

In a second configuration, switches 5104, 5106 and 5114 are set for bi-ventricular pacing. Switch 5104 is connected to switch 5112. Switch 5106 is connected to ground. Switch 5114 is connected the left ventricle lead. In this manner, pacing can be delivered to leads located at both ventricles.

In another configuration, not shown with a figure, a three output channel arrangement to facilitate a BiV pacing profile where the LV is paced with a conventional negative pulse and RV paced with Xstim.

Switches 5110 and 5112 provide the ability to modify the polarity of the voltages seen between the ring and tip electrodes of the right ventricle pacing lead.

As should be apparent from the various discussions herein, the pacing profile can include, for example, variations in voltage levels, pulse durations and phase differences between pulses.

The variations in pacing profiles allow for a number of different applications to be implemented. In one such application, the results of pacing (e.g., QRS width, pressure measurements, synchronicity of contracts and the like) are compared between the different profiles. These results can then be used to select the pacing profile (e.g., Xstim or bi-ventricular) that is to be used for the patient.

In another application, the device includes a sensing function to detect the function of the left ventricle. The sensed function can be used to determine whether the current pacing profile is adequate and/or capturing a contraction of the left ventricle. In a specific instance, Xstim pacing is used while sensing heart function in the left ventricle. When the sensed function shows a potential problem (e.g., no capture, wide QRS or other problems) the pacing profile can be adjusted accordingly. Adjustment of the pacing profile can involve adjustment of the voltage. For instance, when partial or complete lack of capture is detected, the pacing voltage could be increased. Other example variations include a change in the polarity of the ring and tip electrodes or an adjustment of the phase of the applied voltages. In a specific example, when inadequate left ventricular function is detected, the device can be changed to a bi-ventricular pacing profile. In some instances, the device can periodically attempt to implement an Xstim pacing profile. If, during the attempt, adequate left ventricular function is detected, Xstim pacing can be resumed. Otherwise, biventricular pacing can continue to be implemented.

In yet another application, the device senses atrium function. This sensed function can be used, for example, to determine the timing for the ventricular pacing profile. The atrium function can be sensed using an electrode in the atrium, or using sensing near the His bundle (e.g., the Xstim pacing lead). When sensing near the His bundle, the sensed function can be detected using the ring lead, the tip lead and/or a dedicated sensing electrode. In a particular instance, the lead includes a sensing electrode that is closer to the distal end of the lead than the ring and tip electrodes. Generally speaking, such placement would allow the sensing electrode to be located such that the sensed atrium signal would be expected to be stronger (e.g., due to placement closer to the atrium).

Cardiac applications represent a specific embodiment of the invention; however, the present invention is also applicable to other therapies, such as those where high current density spot(s) away from the electrodes are beneficial for stimulating the target including, but not limited to, nerves, muscle, gastric and intestine system, and cortex. For example, U.S. Pat. No. 5,299,569 to Wernicke et al. issued Apr. 5, 1994 (and incorporated herein by reference) is one of a number of patents assigned to Cyberonics, Inc. describing pacing the vagus nerve to treat a wide variety of disorders. Pacing electrodes are applied directly to the vagus nerve in, for example, the neck. Application of an electrode directly to the vagus nerve creates risk of mechanical injury (e.g., pressure necrosis) to the nerve. One use of the present invention in such application involve electrodes (such as previously illustrated $E_1$, $E_2$) placed subcutaneously near (transcutaneously or transvenously coupled) but not on the vagus nerve (VN) in the neck. A reference electrode RE can be placed subcutaneously (transcutaneously or transvenously coupled) on an opposite side of the nerve VN. In such embodiments, the electrodes are connected to a pulse generator IPG. With signals as described above, the resulting field captures the vagus nerve. The signals may be selected to have amplitude, frequency and other parameters as more fully described in the '569 (Wernicke et al.) patent. It will be appreciated that other alternative examples of using the present invention to pace an organ or the nerve will occur to one of ordinary skill in the art with the benefit of the teachings of the present invention.

The skilled artisan will recognize that the various aspects discussed in connection with the present invention can be implemented in a variety of combinations and manners. Moreover, aspects discussed in connection with the various references disclosed and incorporated herein, including those references indicated at the beginning of this document, can be used in combination with aspects of the present invention. In particular to the extent that the references indicated at the beginning of this document include a number of similar figures and related discussions, the skilled artisan would appreciate the interoperability of aspects disclosed therein even for figures not common between documents. These documents provide substantial disclosures throughout which teach aspects that can be used in combination with embodiments of the present invention and these documents are thus incorporated by reference in their entirety. For instance, the U.S. Provisional Patent Application identified by Ser. No. 61/020,511 includes an appendix with figures depicting various pacing electrodes and associated circuitry, and such embodiment(s) can be used in combination with aspects of the present invention.

The various embodiments described above are provided by way of illustration only and should not be construed to limit the invention. Based on the above discussion and illustrations, those skilled in the art will readily recognize that various modifications and changes may be made without strictly following the exemplary embodiments and applications illustrated and described herein. Such modifications and changes do not depart from the true spirit and scope of the present invention.

What is claimed is:

1. An implantable medical device comprising:
an electrostimulation circuit configured to:
generate at least partially concurrent electrostimulation pulses of opposing polarity to be delivered via electrodes positioned at a target region at or near a bundle of His in a right ventricle of a heart, the electrostimulation pulses including at least two pulses occurring sufficiently proximate one another in at least one of time or distance to elicit myocardium capture near the target region at or near the bundle of His; and
generate a defibrillation signal.

2. The implantable medical device of claim 1, further comprising an implantable lead assembly including a first electrode and a second electrode; and
wherein the electrostimulation circuit is configured to generate two electrostimulation pulses including a first pulse configured to be delivered via the first electrode and a second pulse configured to be delivered via the second electrode.

3. The implantable medical device of claim 2, comprising a third electrode configured to be positioned in the right ventricle, and wherein the electrostimulation circuit is configured to deliver the defibrillation signal via the third electrode.

4. The implantable medical device of claim 2, wherein the first pulse and the second pulse include respective portions that are at least partially concurrent in time.

5. The implantable medical device of claim 4, wherein one or more of the first pulse or the second pulse includes a biphasic waveform.

6. The implantable medical device of claim 5, wherein the electrostimulation circuit is configured to generate an electrostimulation pulse including a reversed pulse polarity once every N beats.

7. The implantable medical device of claim 1, wherein the electrostimulation circuit is configured to generate the defibrillation signal in response to obtained information indicative of a tachyarrhythmia, the information obtained via an electrode positioned in the right ventricle of the heart.

8. A method comprising:
generating at least partially concurrent electrostimulation pulses of opposing polarity to be delivered via electrodes positioned at a target region at or near the bundle of His in a right ventricle of a heart, the electrostimulation pulses including at least two pulses occurring sufficiently proximate one another in at least one of time or distance to elicit myocardium capture near the target region at or near the bundle of His; and
generating a defibrillation signal in response to a sensed signal indicating the heart is in a defibrillation.

9. The method of claim 8, wherein generating the two pulses includes generating a first pulse configured to be delivered via a first electrode and a second pulse configured to be delivered via a second electrode.

10. The method of claim 9, comprising delivering the defibrillation signal to a third electrode positioned in the right ventricle.

11. The method of claim 9, wherein the first pulse and the second pulse include respective portions that are at least partially concurrent in time.

12. The method of claim 11, wherein one or more of the first pulse or the second pulse includes a biphasic waveform.

13. The method of claim 12, wherein generating the pulses includes generating an electrostimulation pulse including a reversed pulse polarity once every N beats.

14. The method of claim 8, comprising obtaining information indicative of a tachyarrhythmia via an electrode positioned in the right ventricle of the heart; and
wherein generating the defibrillation signal includes generating the defibrillation signal in response to the obtained information indicative of the tachyarrhythmia.

15. A processor-readable medium, including instructions that, when performed by a processor, cause the processor to:
generate at least partially concurrent electrostimulation pulses of opposing polarity to be delivered via electrodes positioned at a target region at or near the bundle of His in a right ventricle of a heart, the electrostimulation pulses including at least two pulses occurring sufficiently proximate one another in at least one of time or distance to elicit myocardium capture near the target region at or near the bundle of His; and
generate a defibrillation signal in response to a sensed signal indicating the heart is in a defibrillation.

16. The processor-readable medium of claim 15, wherein the instructions that cause the processor to generate the electrostimulation pulses include instructions to generate a first pulse configured to be delivered via a first electrode and a second pulse configured to be delivered via a second electrode.

17. The processor-readable medium of claim 16, wherein the instructions that cause the processor to generate the defibrillation signal include instructions to generate a defibrillation signal to be delivered via a third electrode positioned in the right ventricle.

18. The processor-readable medium of claim 16, wherein the first pulse and the second pulse include respective portions that are at least partially concurrent in time.

19. The processor-readable medium of claim 18, wherein one or more of the first pulse or the second pulse includes a biphasic waveform.

20. The processor-readable medium of claim 19, wherein the instructions that cause the processor to generate the electrostimulation pulses include instructions to generate an electrostimulation pulse including a reversed pulse polarity once every N beats.

21. The processor-readable medium of claim 15, wherein the instructions that cause the processor to generate the defibrillation signal include instructions to generate the defibrillation signal in response to obtained information indicative of a tachyarrhythmia, the information obtained via an electrode positioned in the right ventricle of the heart.

* * * * *